United States Patent
Covel et al.

(10) Patent No.: US 9,365,511 B2
(45) Date of Patent: Jun. 14, 2016

(54) BIPHENYL-ETHYL-PYRROLIDINE DERIVATIVES AS HISTAMINE H3 RECEPTOR MODULATORS FOR THE TREATMENT OF COGNITIVE DISORDERS

(71) Applicant: Arena Pharmaceuticals, Inc., San Diego, CA (US)

(72) Inventors: Jonathan A. Covel, San Diego, CA (US); Albert S. Ren, San Diego, CA (US); Graeme Semple, San Diego, CA (US); Thuy-Anh Tran, San Diego, CA (US); Zheng Wei, San Diego, CA (US); Yifeng Xiong, San Diego, CA (US)

(73) Assignee: ARENA PHARMACEUTICALS, INC., San Diego, CA (US)

( * ) Notice: Subject to any disclaimer, the term of this patent is extended or adjusted under 35 U.S.C. 154(b) by 0 days.

(21) Appl. No.: 14/760,022

(22) PCT Filed: Jan. 8, 2014

(86) PCT No.: PCT/US2014/010632
§ 371 (c)(1),
(2) Date: Jul. 9, 2015

(87) PCT Pub. No.: WO2014/110103
PCT Pub. Date: Jul. 17, 2014

(65) Prior Publication Data
US 2015/0353488 A1    Dec. 10, 2015

Related U.S. Application Data

(60) Provisional application No. 61/750,475, filed on Jan. 9, 2013.

(51) Int. Cl.
| | |
|---|---|
| *C07D 207/06* | (2006.01) |
| *C07D 401/10* | (2006.01) |
| *C07D 403/10* | (2006.01) |
| *C07D 257/04* | (2006.01) |
| *C07D 295/14* | (2006.01) |

(52) U.S. Cl.
CPC ............ *C07D 207/06* (2013.01); *C07D 257/04* (2013.01); *C07D 295/14* (2013.01); *C07D 401/10* (2013.01); *C07D 403/10* (2013.01)

(58) Field of Classification Search
None
See application file for complete search history.

(56) References Cited

FOREIGN PATENT DOCUMENTS

WO   WO2009058300   *   5/2009

OTHER PUBLICATIONS

Vohora et al., Histamine H3 receptor antagonists/inverse agonists on cognitive and motor processes: relevance to Alzheimer's disease, ADHD, schizophrenia, and drug abuse. 2012, 6, 1-10.*
Bhowmik et al., Histamine H3 receptor antagonist in relation to epilepsy and neurodegeneration: a systemic consideration of recent progress and perspective. British Journal of Pharmacology. 2012, 167, 1398-1414.*
Yan et al., Histamine H3 receptors aggravate cerebral ischaemic injury by histamine-independent mechanisms. Nature Communications. 2014, 1-12.*
Femenia et al., Hippocampal-Dependent Antidepressant Action of the H3 Receptor Antagonist Clobenpropit in a Rat Model of Depression. International Journal of Neuropsychopharmacology. 2014, 1-11.*
Shafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*

* cited by examiner

*Primary Examiner* — Rebecca Anderson
*Assistant Examiner* — Po-Chih Chen
(74) *Attorney, Agent, or Firm* — Lewis Roca Rothgerber Christie LLP

(57) ABSTRACT

The present invention relates to compounds of Formula (Ia) and pharmaceutically acceptable salts, solvates, and hydrates thereof, that modulate the activity of the histamine H3 receptor (Ia). Compounds of the present invention and pharmaceutical compositions thereof are directed to methods useful in the treatment of histamine H3-associated disorders.

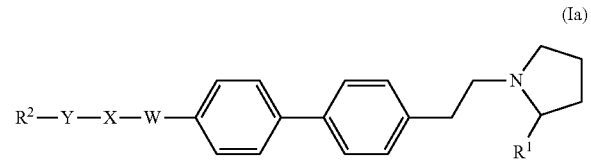

28 Claims, 6 Drawing Sheets

BIPHENYL-ETHYL-PYRROLIDINE DERIVATIVES AS HISTAMINE H3 RECEPTOR MODULATORS FOR THE TREATMENT OF COGNITIVE DISORDERS

This application is a §371 National Stage Application of PCT/US2014/010632, filed Jan. 8, 2014, which claims the benefit of priority of U.S. Provisional Application 61/750,475, filed Jan. 9, 2013.

FIELD OF THE INVENTION

The present invention relates to compounds of Formula (Ia) and pharmaceutical compositions thereof that modulate the activity of the histamine H3 receptor (H3R) and are useful in methods for the treatment of H3 receptor-associated disorders, such as, cognitive disorders, epilepsy, brain trauma, depression, obesity, disorders of sleep and wakefulness such as excessive daytime sleepiness, narcolepsy, shift-work sleep disorder, drowsiness as a side effect from a medication, maintenance of vigilance to aid in the completion of tasks and the like, cataplexy, hypersomnia, somnolence syndrome, jet lag, sleep apnea and the like, attention deficit hyperactivity disorder (ADHD), schizophrenia, allergies, allergic responses in the upper airway, allergic rhinitis, nasal congestion, dementia, Alzheimer's disease, pain, pruritus, and the like.

SUMMARY OF THE INVENTION

One aspect of the present invention encompasses, inter alia, certain biphenyl derivatives selected from compounds of Formula (Ia) and pharmaceutically acceptable salts, solvates, and hydrates thereof:

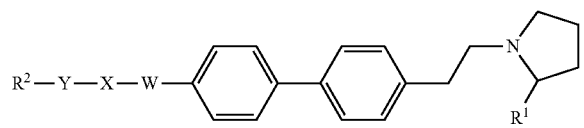

(Ia)

wherein:
$R^1$ is $C_1$-$C_4$ alkyl;
$R^2$ is selected from: $C_1$-$C_4$ alkoxycarbonyl, carboxyl, and tetrazolyl;
W is selected from: $C_1$-$C_4$ alkylene, $C_3$-$C_7$ cycloalkylene, and carbonyl; or
W is absent;
X is selected from: —O—, —NHC=O—, and carbonyl; or
X is absent; and
Y is selected from: $C_1$-$C_4$ alkylene, $C_3$-$C_7$ cycloalkylene, and heterocycylene; or
Y is absent.

One aspect of the present invention pertains to compositions comprising a compound of the present invention.

One aspect of the present invention pertains to pharmaceutical compositions comprising a compound of the present invention and a pharmaceutically acceptable carrier.

One aspect of the present invention pertains to methods for treating an H3 receptor-associated disorder in an individual comprising administering to the individual in need thereof a therapeutically effective amount of a compound of the present invention or a pharmaceutical composition thereof.

One aspect of the present invention pertains to methods of treating allergic rhinitis in an individual comprising administering to the individual in need thereof a therapeutically effective amount of a compound of the present invention or a pharmaceutical composition thereof.

One aspect of the present invention pertains to the use of a compound of the present invention or a pharmaceutical composition thereof in the manufacture of a medicament for the treatment of an H3 receptor-associated disorder.

One aspect of the present invention pertains to the use of a compound of the present invention or a pharmaceutical composition thereof in the manufacture of a medicament for the treatment of allergic rhinitis.

One aspect of the present invention pertains to a compound of the present invention or a pharmaceutical composition thereof for use in a method of treatment of the human or animal body by therapy.

One aspect of the present invention pertains to a compound of the present invention or a pharmaceutical composition thereof for use in a method for the treatment of an H3 receptor-associated disorder.

One aspect of the present invention pertains to a compound of the present invention or a pharmaceutical composition thereof for use in a method for the treatment of allergic rhinitis.

One aspect of the present invention pertains to processes for preparing a composition comprising admixing a compound of the present invention and a pharmaceutically acceptable carrier.

One aspect of the present invention pertains to processes for preparing a pharmaceutical composition comprising admixing compound of the present invention and a pharmaceutically acceptable carrier.

These and other aspects of the invention disclosed herein will be set forth in greater detail as the patent disclosure proceeds.

The data shows that Compound 3 effectively inhibits histamine-induced pruritus in mice.

Figure 6:
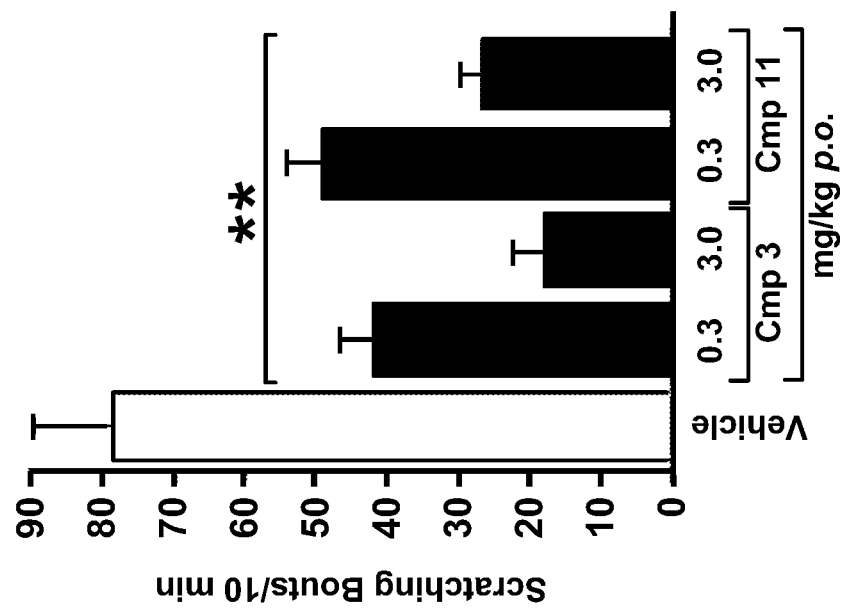

FIG. 6 shows the data from the oral administration of Compound 3 and Compound 11 in the histamine-induced pruritus mouse model. The data shows that Compound 3 and Compound 11 effectively inhibit histamine-induced pruritus in mice.

DETAILED DESCRIPTION OF THE INVENTION

Definitions

For clarity and consistency, the following definitions will be used throughout this patent document.

The term "agonists" refers to moieties that interact and activate the receptor, such as the H3 receptor and initiate a physiological or pharmacological response characteristic of that receptor. For example, when moieties activate the intracellular response upon binding to the receptor, or enhance GTP binding to membranes.

The term "antagonists" refers to moieties that competitively bind to the receptor at the same site as agonists (for example, the endogenous ligand), but which do not activate the intracellular response initiated by the active form of the receptor and can thereby inhibit the intracellular responses by agonists or partial agonists. Antagonists do not diminish the baseline intracellular response in the absence of an agonist or partial agonist.

The term "composition" refers to a compound of the present invention, including but not limited to, salts, solvates, and hydrates of a compound of the present invention, in combination with at least one additional component.

The term "contact or contacting" refers to bringing the indicated moieties together, whether in an in vitro system or an in vivo system. Thus, "contacting" a H3 receptor with a compound of the invention includes the administration of a compound of the present invention to an individual, preferably a human, having a H3 receptor, as well as, for example, introducing a compound of the invention into a sample containing a cellular or more purified preparation containing a H3 receptor.

The term "in need of treatment" and the term "in need thereof" when referring to treatment are used interchangeably to mean a judgment made by a caregiver (e.g. physician, nurse, nurse practitioner, etc. in the case of humans; veterinarian in the case of animals, including non-human mammals) that an individual or animal requires or will benefit from treatment. This judgment is made based on a variety of factors that are in the realm of a caregiver's expertise, but that includes the knowledge that the individual or animal is ill, or will become ill, as the result of a disease, condition or disorder that is treatable by the compounds of the invention. Accordingly, the compounds of the invention can be used in a protective or preventive manner; or compounds of the invention can be used to alleviate, inhibit or ameliorate the disease, condition or disorder.

The term "individual" refers to any animal, including mammals, preferably mice, rats, other rodents, rabbits, dogs, cats, swine, cattle, sheep, horses, or primates and most preferably humans.

The term "inverse agonists" refers to moieties that bind to the endogenous form of the receptor or to the constitutively activated form of the receptor and which inhibit the baseline intracellular response initiated by the active form of the receptor below the normal base level of activity which is observed in the absence of agonists or partial agonists, or decrease GTP binding to membranes. Preferably, the baseline intracellular response is inhibited in the presence of the inverse agonist by at least 30%, more preferably by at least 50% and most preferably by at least 75%, as compared with the baseline response in the absence of the inverse agonist.

The term "modulate or modulating" refers to an increase or decrease in the amount, quality, response or effect of a particular activity, function or molecule.

The term "pharmaceutical composition" refers to a composition comprising at least one active ingredient; including but not limited to, salts, solvates and hydrates of compounds of the present invention; whereby the composition is amenable to investigation or treatment for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

The term "therapeutically effective amount" refers to the amount of active compound or pharmaceutical agent that elicits the biological or medicinal response in a tissue, system, animal, individual or human that is being sought by a researcher, veterinarian, medical doctor or other clinician or caregiver; or by an individual, which includes one or more of the following:

(1) Preventing the disease; for example, preventing a disease, condition or disorder in an individual that may be predisposed to the disease, condition or disorder but does not yet experience or display the pathology or symptomatology of the disease, (2) Inhibiting the disease; for example, inhibiting a disease, condition or disorder in an individual that is experiencing or displaying the pathology or symptomatology of the disease, condition or disorder (i.e., arresting further development of the pathology and/or symptomatology) and (3) Ameliorating the disease; for example, ameliorating a disease, condition or disorder in an individual that is experiencing or displaying the pathology or symptomatology of the disease, condition or disorder (i.e., reversing the pathology and/or symptomatology).

Chemical Group, Moiety, or Radical

The term "$C_1$-$C_4$ alkoxycarbonyl" refers to a radical comprising a single $C_1$-$C_4$ alkoxy group attached to the carbon of a carbonyl group, wherein $C_1$-$C_4$ alkoxy has the same definition as found herein. The alkoxycarbonyl group may be represented by the following:

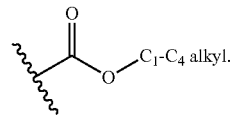

The term "$C_1$-$C_4$ alkylene" refers to a straight or branched, saturated aliphatic, divalent radical having 1 to 4 carbon atoms. Some embodiments contain 1 to 3 carbons. Some embodiments contain 1 or 2 carbons. In some embodiments, $C_1$-$C_4$ alkylene is selected from: methylene (i.e., —$CH_2$—), ethane-1,2-diyl (i.e., —$CH_2CH_2$—), ethane-1,1-diyl (i.e., —$CH(CH_3)$—), propane-2,2-diyl (i.e., —$C(CH_3)_2$—), propane-1,3-diyl (i.e., —$CH_2CH_2CH_2$—), butane-1,4-diyl (i.e., —$CH_2CH_2CH_2$—), 2-methylpropane-1,2-diyl (i.e., —$C(CH_3)_2CH_2$—), and the like.

The term "$C_1$-$C_4$ alkyl" refers to a straight or branched carbon radical containing 1 to 4 carbons. Some embodiments are 1 to 3 carbons. Some embodiments are 1 to 2 carbons.

Some embodiments are 1 carbon. Examples of an alkyl include methyl, ethyl, n-propyl, iso-propyl, n-butyl, s-butyl, isobutyl, and the like.

The term "carbonyl" refers to the group —C(=O)—.

The term "carboxy" refers to the group —CO₂H.

The term "C₃-C₇ cycloalkylene" refers to saturated ring di-radicals containing 3 to 7 carbons. Some embodiments contain 3 to 6 carbons. Some embodiments contain 5 to 6 carbons. Some embodiments contain 3 to 4 carbons. In some embodiments, C₃-C₇ cycloalkylene is selected from: cyclopropane-1,1-diyl, cyclobutane-1,1-diyl, cyclopentane-1,1-diyl, cyclohexane-1,1-diyl, cyclopropane-1,2-diyl, cyclobutane-1,2-diyl, cyclopentane-1,2-diyl, cyclohexane-1,2-diyl, cyclopentane-1,3-diyl, cyclohexane-1,3-diyl, cyclohexane-1,4-diyl, cycloheptane-1,1-diyl, cycloheptane-1,2-diyl, and the like. For further clarity, several representative chemical structures for the term "C₃-C₇ cycloalkylene" are shown below:

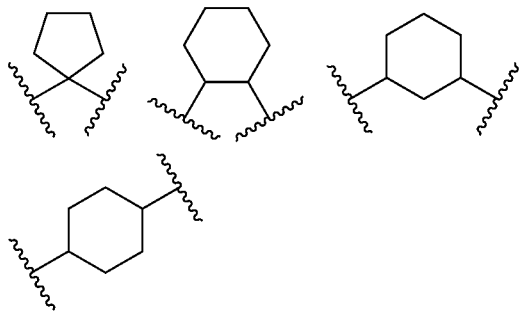

cyclopentane-1,1-diyl cyclohexane-1,2-diyl cyclohexane-1,3-diyl cyclohexane-1,4-diyl.

The term "heterocycle" refers to non-aromatic ring heterocycles containing 3 to 8 ring atoms, wherein one, two or three ring atoms are heteroatoms selected from, for example: O, S, and N, wherein N is optionally substituted with H, C₁-C₄ acyl, or C₁-C₄ alkyl, and S is optionally substituted with one or two oxygen atoms. Examples of a heterocycle include aziridine, azetidine, piperidine, morpholine, piperazine, pyrrolidine, [1,3]-dioxolane, thiomorpholine, [1,4]oxazepane, 1,1-dioxothiomorpholine, azepane, tetrahydrofurane, tetrahydropyrane, tetrahydrothiopyrane, 1-oxidotetrahydro-2H-thiopyrane, 1,1-dioxidotetrahydro-2H-thiopyrane, and the like.

The term "heterocyclylene" refers to non-aromatic ring heterocycle di-radicals containing 3 to 8 ring atoms, wherein heterocycle is as described herein. Examples of a heterocyclylene group include, but are not limited to, aziridine-2,2-diyl, azetidine-2,2-diyl, azetidine-3,3-diyl, pyrrolidine-1,2-diyl, pyrrolidine-1,3-diyl, pyrrolidine-2,3-diyl, piperidine-1,2-diyl, piperidine-1,3-diyl, piperidine-1,4-diyl, oxetane-2,3-diyl, oxetane-2,4-diyl, tetrahydro-2H-pyran-2,3-diyl, 1,1-dioxidotetrahydro-2H-thiopyran-3,5-diyl, and the like.

Compounds of the Invention:

One aspect of the present invention pertains to certain biphenyl derivatives selected from compounds of Formula (Ia):

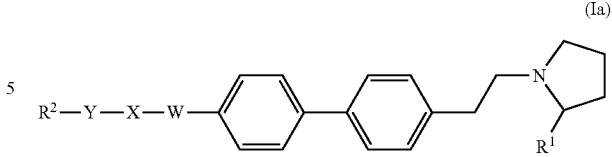

and pharmaceutically acceptable salts, solvates, and hydrates thereof; wherein: $R^1$, $R^2$, W, X, and Y have the same definitions as described herein, supra and infra.

One aspect of the present invention pertains to certain biphenyl derivatives selected from compounds of Formula (Ic):

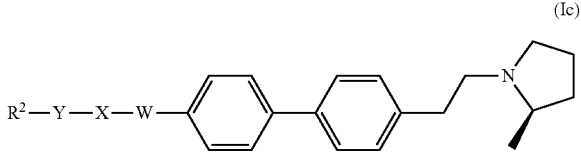

and pharmaceutically acceptable salts, solvates, and hydrates thereof; wherein: $R^2$, W, X, and Y have the same definitions as described herein, supra and infra.

One aspect of the present invention pertains to certain biphenyl derivatives selected from compounds of Formula (Ie):

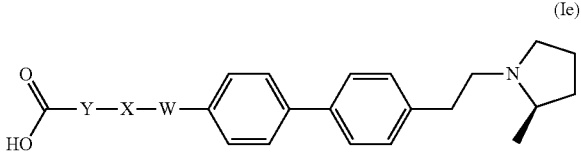

and pharmaceutically acceptable salts, solvates, and hydrates thereof; wherein: W, X, and Y have the same definitions as described herein, supra and infra.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables (e.g., $R^1$, $R^2$, W, X, and Y) contained within the generic chemical formulae described herein (e.g., (Ia), (Ic), (Ie), (Ig), (Ii), (Ik), and (Im)) are specifically embraced by the present invention just as if each and every combination was individually explicitly recited, to the extent that such combinations embrace compounds that result in stable compounds (i.e., compounds that can be isolated, characterized and tested for biological activity). In addition, all subcombinations of the chemical groups listed in the embodiments describing such variables, as well as all subcombinations of uses and medical indications described herein, are also specifically embraced by the present invention just as if each and every subcombination of chemical groups and subcombination of uses and medical indications was individually and explicitly recited herein.

As used herein, "substituted" indicates that at least one hydrogen atom of the chemical group is replaced by a non-hydrogen substituent or group, the non-hydrogen substituent or group can be monovalent or divalent. When the substituent or group is divalent, then it is understood that this group is further substituted with another substituent or group. When a chemical group herein is "substituted" it may have up to the full valance of substitution; for example, a methyl group can be substituted by 1, 2, or 3 substituents, a methylene group can be substituted by 1 or 2 substituents and the like. Likewise, "substituted with one or more substituents" refers to the substitution of a group with one substituent up to the total number of substituents physically allowed by the group. Further, when a group is substituted with more than one group they can be identical or they can be different.

Compounds of the invention can also include tautomeric forms, such as keto-enol tautomers and the like. Tautomeric forms can be in equilibrium or sterically locked into one form by appropriate substitution. It is understood that the various tautomeric forms are within the scope of the compounds of the present invention.

It is understood and appreciated that compounds of Formula (Ia) and formulae related thereto may have one or more chiral centers and therefore can exist as enantiomers and/or diastereoisomers. The invention is understood to extend to and embrace all such enantiomers, diastereoisomers and mixtures thereof, including but not limited to racemates. It is understood that compounds of Formula (Ia) and formulae used throughout this disclosure are intended to represent all individual enantiomers and mixtures thereof, unless stated or shown otherwise.

The $R^1$ Group

In some embodiments, $R^1$ is $C_1$-$C_4$ alkyl.
In some embodiments, $R^1$ is methyl.

The $R^2$ Group

In some embodiments, $R^2$ is selected from: $C_1$-$C_4$ alkoxycarbonyl, carboxyl, and tetrazolyl.
In some embodiments, $R^2$ is selected from: methoxycarbonyl, ethoxycarbonyl, tert-butoxycarbonyl, carboxyl, 1H-tetrazol-1-yl, 2H-tetrazol-2-yl, and 1H-tetrazol-5-yl.
In some embodiments, $R^2$ is $C_1$-$C_4$ alkoxycarbonyl.
In some embodiments, $R^2$ is selected from: methoxycarbonyl, ethoxycarbonyl, and tert-butoxycarbonyl.
In some embodiments, $R^2$ is carboxyl.
In some embodiments, $R^2$ is tetrazolyl.
In some embodiments, $R^2$ is selected from: 1H-tetrazol-1-yl, 2H-tetrazol-2-yl, and 1H-tetrazol-5-yl.
In some embodiments, $R^2$ is methoxycarbonyl.
In some embodiments, $R^2$ is ethoxycarbonyl.
In some embodiments, $R^2$ is tert-butoxycarbonyl.
In some embodiments, $R^2$ is 1H-tetrazol-1-yl.
In some embodiments, $R^2$ is 2H-tetrazol-2-yl.
In some embodiments, $R^2$ is 1H-tetrazol-5-yl.

The Group W

In some embodiments, W is selected from: $C_1$-$C_4$ alkylene, $C_3$-$C_7$ cycloalkylene, and carbonyl; or W is absent.
In some embodiments, W is selected from: methylene, ethane-1,2-diyl, propane-2,2-diyl, propane-1,3-diyl, cyclopentane-1,1-diyl, and carbonyl.
In some embodiments, W is $C_1$-$C_4$ alkylene.
In some embodiments, W is selected from: methylene, ethane-1,2-diyl, propane-1,3-diyl, and propane-2,2-diyl.
In some embodiments, W is $C_3$-$C_7$ cycloalkylene.
In some embodiments, W is cyclopentane-1,1-diyl.
In some embodiments, W is carbonyl.
In some embodiments, W is methylene.
In some embodiments, W is ethane-1,2-diyl.
In some embodiments, W is propane-2,2-diyl.
In some embodiments, W is propane-1,3-diyl.
In some embodiments, W is carbonyl.
In some embodiments, W is absent.

One aspect of the present invention pertains to certain biphenyl derivatives selected from compounds of Formula (Ig):

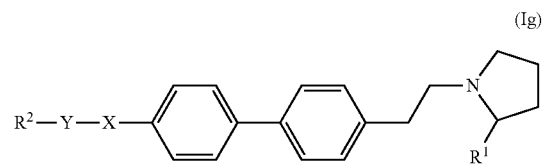

and pharmaceutically acceptable salts, solvates, and hydrates thereof; wherein: $R^1$, $R^2$, X, and Y have the same definitions as described herein, supra and infra.

The Group X

In some embodiments, X is selected from: —O—, —NHC=O—, and carbonyl; or X is absent.
In some embodiments, X is —O—.
In some embodiments, X is —NHC=O—.
In some embodiments, X is carbonyl.
In some embodiments, X is absent.

One aspect of the present invention pertains to certain biphenyl derivatives selected from compounds of Formula (Ii):

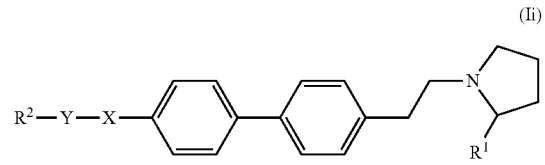

and pharmaceutically acceptable salts, solvates, and hydrates thereof; wherein: $R^1$, $R^2$, W, and Y have the same definitions as described herein, supra and infra.

The Group Y

In some embodiments, Y is selected from: $C_1$-$C_4$ alkylene, $C_3$-$C_7$ cycloalkylene, and heterocyclylene; or Y is absent.
In some embodiments, Y is selected from: methylene, propane-2,2-diyl, propane-1,3-diyl, ethane-1,1-diyl, ethane-1,2-diyl, cyclohexane-1,2-diyl, pyrrolidine-1,2-diyl, and piperidine-1,4-diyl.
In some embodiments, Y is $C_1$-$C_4$ alkylene.
In some embodiments, Y is selected from: methylene, propane-2,2-diyl, propane-1,3-diyl, ethane-1,1-diyl, and ethane-1,2-diyl.
In some embodiments, Y is $C_3$-$C_7$ cycloalkylene.
In some embodiments, Y is cyclohexane-1,2-diyl.
In some embodiments, Y is heterocyclylene.
In some embodiments, Y is selected from: pyrrolidine-1,2-diyl and piperidine-1,4-diyl.
In some embodiments, Y is methylene.
In some embodiments, Y is propane-2,2-diyl.
In some embodiments, Y is propane-1,3-diyl.
In some embodiments, Y is ethane-1,1-diyl.
In some embodiments, Y is ethane-1,2-diyl.
In some embodiments, Y is pyrrolidine-1,2-diyl.
In some embodiments, Y is piperidine-1,4-diyl.
In some embodiments, Y is absent.

One aspect of the present invention pertains to certain biphenyl derivatives selected from compounds of Formula (Ik):

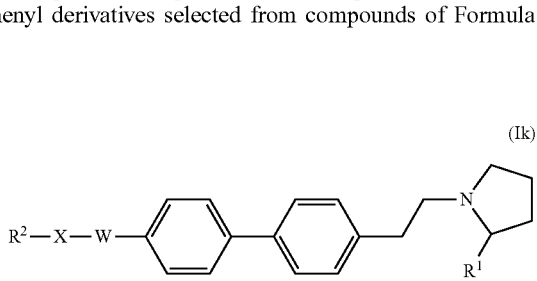

and pharmaceutically acceptable salts, solvates, and hydrates thereof; wherein: $R^1$, $R^2$, W, and X have the same definitions as described herein, supra and infra.

Combinations of Groups W, X, and Y

In some embodiments, W and X are both absent.

In some embodiments, W and Y are both absent.

In some embodiments, X and Y are both absent.

One aspect of the present invention pertains to certain biphenyl derivatives selected from compounds of Formula (Im):

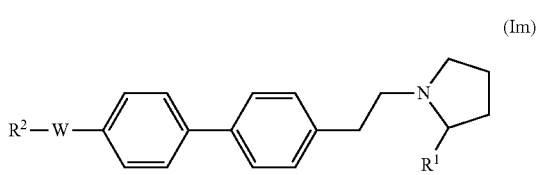

and pharmaceutically acceptable salts, solvates, and hydrates thereof; wherein: $R^1$, $R^2$, and W have the same definitions as described herein, supra and infra.

Peripherally Restricted Compounds

One aspect of the present invention pertains to certain biphenyl derivatives selected from compounds of Formula (Ia) or a formula related thereto (e.g., (Ic), (Ie), (Ig), (Ii), (Ik), and (Im)) and pharmaceutically acceptable salts, solvates, and hydrates thereof; wherein the compounds are peripherally restricted (i.e., the concentration of the compound is higher in the plasma than the brain). In some embodiments, compounds of the present invention have a brain to plasma ratio in the range of about 1.0 to about 0.0001. In some embodiments, compounds of the present invention have a brain to plasma ratio in the range of about 0.9 to about 0.0001. In some embodiments, compounds of the present invention have a brain to plasma ratio of less than about 1.0. In some embodiments, compounds of the present invention have a brain to plasma ratio of less than or equal to 0.9, 0.8, 0.7, 0.6, 0.5, 0.4, 0.3, 0.2, 0.1, 0.09, 0.08, 0.07, 0.06, 0.05, 0.04, 0.03, 0.02, or 0.01. The brain to plasma ratio can be determined by any of the conventional methods know in the art, for example, see Example 7.

Certain Combinations of the Present Invention

Some embodiments of the present invention pertain to compounds of Formula (Ic) and pharmaceutically acceptable salts, solvates, and hydrates thereof:

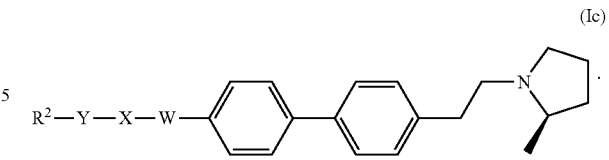

Some embodiments of the present invention pertain to compounds of Formula (Ic) and pharmaceutically acceptable salts, solvates, and hydrates thereof:

wherein:

$R^2$ is selected from: methoxycarbonyl, ethoxycarbonyl, tert-butoxycarbonyl, carboxyl, 1H-tetrazol-1-yl, 2H-tetrazol-2-yl, and 1H-tetrazol-5-yl;

W is selected from: methylene, ethane-1,2-diyl, propane-2,2-diyl, propane-1,3-diyl, cyclopentane-1,1-diyl, and carbonyl; or W is absent;

X is selected from: —O—, —NHC=O—, and carbonyl; or

X is absent; and

Y is selected from: methylene, propane-2,2-diyl, propane-1,3-diyl, ethane-1,1-diyl, ethane-1,2-diyl, cyclohexane-1,2-diyl, pyrrolidine-1,2-diyl, and piperidine-1,4-diyl; or Y is absent.

Some embodiments of the present invention pertain to compounds of Formula (Ic) and pharmaceutically acceptable salts, solvates, and hydrates thereof:

wherein:

$R^2$ is selected from: $C_1$-$C_4$ alkoxycarbonyl, carboxyl, and tetrazolyl;

W is selected from: $C_1$-$C_4$ alkylene and $C_3$-$C_7$ cycloalkylene;

X is selected from: —O—, —NHC=O—, and carbonyl; or

X is absent; and

Y is selected from: $C_1$-$C_4$ alkylene, $C_3$-$C_7$ cycloalkylene, and heterocyclylene; or Y is absent.

Some embodiments of the present invention pertain to compounds of Formula (Ic) and pharmaceutically acceptable salts, solvates, and hydrates thereof:

wherein:

$R^2$ is selected from: methoxycarbonyl, ethoxycarbonyl, tert-butoxycarbonyl, carboxyl, 1H-tetrazol-1-yl, 2H-tetrazol-2-yl, and 1H-tetrazol-5-yl;

W is selected from: methylene, ethane-1,2-diyl, propane-2,2-diyl, propane-1,3-diyl, and cyclopentane-1,1-diyl;

X is selected from: —O—, —NHC=O—, and carbonyl; or

X is absent; and

Y is selected from: methylene, propane-2,2-diyl, propane-1,3-diyl, ethane-1,1-diyl, ethane-1,2-diyl, cyclohexane-1,2-diyl, pyrrolidine-1,2-diyl, and piperidine-1,4-diyl; or Y is absent.

Some embodiments of the present invention pertain to compounds of Formula (Ic) and pharmaceutically acceptable salts, solvates, and hydrates thereof:

wherein:

$R^2$ is selected from: $C_1$-$C_4$ alkoxycarbonyl and carboxyl;

W is selected from: $C_1$-$C_4$ alkylene and $C_3$-$C_7$ cycloalkylene; or

W is absent;

X is selected from: —O—, —NHC=O—, and carbonyl; and

Y is selected from: $C_1$-$C_4$ alkylene, $C_3$-$C_7$ cycloalkylene, and heterocyclylene.

Some embodiments of the present invention pertain to compounds of Formula (Ic) and pharmaceutically acceptable salts, solvates, and hydrates thereof:
wherein:
$R^2$ is selected from: methoxycarbonyl, ethoxycarbonyl, tert-butoxycarbonyl, and carboxyl;
W is selected from: methylene, ethane-1,2-diyl, and cyclopentane-1,1-diyl; or
W is absent;
X is selected from: —O—, —NHC═O—, and carbonyl; and
Y is selected from: methylene, propane-2,2-diyl, propane-1,3-diyl, ethane-1,1-diyl, ethane-1,2-diyl, cyclohexane-1,2-diyl, pyrrolidine-1,2-diyl, and piperidine-1,4-diyl.

Some embodiments of the present invention pertain to compounds of Formula (Ie) and pharmaceutically acceptable salts, solvates, and hydrates thereof:

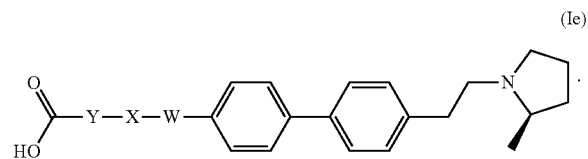

(Ie)

Some embodiments of the present invention pertain to compounds of Formula (Ie) and pharmaceutically acceptable salts, solvates, and hydrates thereof:
wherein:
W is selected from: methylene, ethane-1,2-diyl, propane-2,2-diyl, propane-1,3-diyl, and cyclopentane-1,1-diyl; or
W is absent;
X is selected from: —O—, —NHC═O—, and carbonyl; or
X is absent; and
Y is selected from: methylene, propane-2,2-diyl, propane-1,3-diyl, ethane-1,1-diyl, ethane-1,2-diyl, cyclohexane-1,2-diyl, and pyrrolidine-1,2-diyl; or
Y is absent.

Some embodiments of the present invention pertain to compounds of Formula (Ie) and pharmaceutically acceptable salts, solvates, and hydrates thereof:
wherein:
W is selected from: $C_1$-$C_4$ alkylene and $C_3$-$C_7$ cycloalkylene;
X is selected from: —O—, —NHC═O—, and carbonyl; or
X is absent; and
Y is selected from: $C_1$-$C_4$ alkylene, $C_3$-$C_7$ cycloalkylene, and heterocyclylene; or
Y is absent.

Some embodiments of the present invention pertain to compounds of Formula (Ie) and pharmaceutically acceptable salts, solvates, and hydrates thereof:
wherein:
W is selected from: methylene, ethane-1,2-diyl, propane-2,2-diyl, propane-1,3-diyl, and cyclopentane-1,1-diyl;
X is selected from: —O—, —NHC═O—, and carbonyl; or
X is absent; and
Y is selected from: methylene, propane-2,2-diyl, propane-1,3-diyl, ethane-1,1-diyl, ethane-1,2-diyl, cyclohexane-1,2-diyl, and pyrrolidine-1,2-diyl; or
Y is absent.

Some embodiments of the present invention pertain to compounds of Formula (Ie) and pharmaceutically acceptable salts, solvates, and hydrates thereof:
wherein:
W is selected from: $C_1$-$C_4$ alkylene and $C_3$-$C_7$ cycloalkylene; or
W is absent;
X is selected from: —O—, —NHC═O—, and carbonyl; and
Y is selected from: $C_1$-$C_4$ alkylene, $C_3$-$C_7$ cycloalkylene, and heterocyclylene.

Some embodiments of the present invention pertain to compounds of Formula (Ie) and pharmaceutically acceptable salts, solvates, and hydrates thereof:
wherein:
W is selected from: methylene, ethane-1,2-diyl, and cyclopentane-1,1-diyl; or
W is absent;
X is selected from: —O—, —NHC═O—, and carbonyl; and
Y is selected from: methylene, propane-2,2-diyl, propane-1,3-diyl, ethane-1,1-diyl, ethane-1,2-diyl, cyclohexane-1,2-diyl, and pyrrolidine-1,2-diyl.

One aspect of the present invention encompasses every combination of one or more compounds selected from the following compounds and pharmaceutically acceptable salts, solvates, and hydrates thereof:
4'-(2-(2-methylpyrrolidin-1-yl)ethyl)biphenyl-4-carboxylic acid; 2-(4'-(2-(2-methylpyrrolidin-1-yl)ethyl)biphenyl-4-yl)acetic acid; 3-(4'-(2-(2-methylpyrrolidin-1-yl)ethyl)biphenyl-4-yl)propanoic acid; ethyl 2-((4'-(2-(2-methylpyrrolidin-1-yl)ethyl)biphenyl-4-yl)methoxy)acetate; 2-((4'-(2-(2-methylpyrrolidin-1-yl)ethyl)biphenyl-4-yl)methoxy)acetic acid; 2-(2-(4'-(2-(2-methylpyrrolidin-1-yl)ethyl)biphenyl-4-yl)ethoxy)acetic acid; 1-(2-(4'-(2-(2-methylpyrrolidin-1-yl)ethyl)biphenyl-4-yl)ethyl)-1H-tetrazole; 2-(2-(4'-(2-(2-methylpyrrolidin-1-yl)ethyl)biphenyl-4-yl)ethyl)-2H-tetrazole; methyl 3-(4'-(2-(2-methylpyrrolidin-1-yl)ethyl)biphenyl-4-yl)propanoate; 2-methyl-2-(4'-(2-(2-methylpyrrolidin-1-yl)ethyl)biphenyl-4-yl)propanoic acid; ethyl 3-(4'-(2-(2-methylpyrrolidin-1-yl)ethyl)biphenyl-4-yl)propanoate; tert-butyl 2-methyl-2-(3-(4'-(2-(2-methylpyrrolidin-1-yl)ethyl)biphenyl-4-yl)propanamido)propanoate; tert-butyl 2-(3-(4'-(2-(2-methylpyrrolidin-1-yl)ethyl)biphenyl-4-yl)propanamido)propanoate; ethyl 2-(1-(4'-(2-(2-methylpyrrolidin-1-yl)ethyl)biphenyl-4-yl)cyclopentanecarboxamido)cyclohexanecarboxylate; ethyl 3-(1-(4'-(2-(2-methylpyrrolidin-1-yl)ethyl)biphenyl-4-yl)cyclopentanecarboxamido)propanoate; methyl 4-(1-(4'-(2-(2-methylpyrrolidin-1-yl)ethyl)biphenyl-4-yl)cyclopentanecarboxamido)butanoate; 2-methyl-2-(3-(4'-(2-(2-methylpyrrolidin-1-yl)ethyl)biphenyl-4-yl)propanamido)propanoic acid; 2-(3-(4'-(2-(2-methylpyrrolidin-1-yl)ethyl)biphenyl-4-yl)propanamido)propanoic acid; 1-(4'-(2-(2-methylpyrrolidin-1-yl)ethyl)biphenyl-4-yl)cyclopentanecarboxylic acid; ethyl 2-(1-(4'-(2-((R)-2-methylpyrrolidin-1-yl)ethyl)biphenyl-4-yl)cyclopentanecarboxamido)cyclohexanecarboxylate; methyl 3-(1-(4'-(2-(2-methylpyrrolidin-1-yl)ethyl)biphenyl-4-yl)cyclopentanecarboxamido)propanoate; tert-butyl 3-(1-(4'-(2-(2-methylpyrrolidin-1-yl)ethyl)biphenyl-4-yl)cyclopentanecarboxamido)propanoate; tert-butyl 4-(1-(4'-(2-(2-methylpyrrolidin-1-yl)ethyl)biphenyl-4-yl)cyclopentanecarboxamido)butanoate; methyl 2-(3-(4'-(2-(2-methylpyrrolidin-1-yl)ethyl)biphenyl-4-yl)propanamido)

acetate; methyl 1-(4'-(2-(2-methylpyrrolidin-1-yl)ethyl)biphenyl-4-yl)cyclopentanecarboxylate; tert-butyl 2-(3-(4'-(2-(2-methylpyrrolidin-1-yl)ethyl)biphenyl-4-yl)propanamido)acetate; methyl 2-(1-(4'-(2-(2-methylpyrrolidin-1-yl)ethyl)biphenyl-4-yl)cyclopentanecarboxamido)acetate; methyl 2-(1-(4'-(2-(2-methylpyrrolidin-1-yl)ethyl)biphenyl-4-yl)cyclopentanecarboxamido)propanoate; 2-(3-(4'-(2-(2-methylpyrrolidin-1-yl)ethyl)biphenyl-4-yl)propanamido) acetic acid; 2-(1-(4'-(2-(2-methylpyrrolidin-1-yl)ethyl)biphenyl-4-yl)cyclopentanecarboxamido)cyclohexanecarboxylic acid; tert-butyl 3-(3-(4'-(2-(2-methylpyrrolidin-1-yl)ethyl)biphenyl-4-yl)propanamido)propanoate; 1-(3-(4'-(2-(2-methylpyrrolidin-1-yl)ethyl)biphenyl-4-yl)propanoyl)pyrrolidine-2-carboxylic acid; 4-(1-(4'-(2-(2-methylpyrrolidin-1-yl)ethyl)biphenyl-4-yl)cyclopentanecarboxamido)butanoic acid; tert-butyl 4-(3-(4'-(2-(2-methylpyrrolidin-1-yl)ethyl)biphenyl-4-yl)propanamido)butanoate; ethyl 1-(3-(4'-(2-(2-methylpyrrolidin-1-yl)ethyl)biphenyl-4-yl)propanoyl)piperidine-4-carboxylate; 4-(4'-(2-(2-methylpyrrolidin-1-yl)ethyl)biphenyl-4-yl)-4-oxobutanoic acid; 5-((4'-(2-(2-methylpyrrolidin-1-yl)ethyl)biphenyl-4-yl)methyl)-1H-tetrazole; methyl 2-(4'-(2-(2-methylpyrrolidin-1-yl)ethyl)biphenyl-4-ylcarboxamido)propanoate; methyl 3-(4'-(2-(2-methylpyrrolidin-1-yl)ethyl)biphenyl-4-ylcarboxamido)propanoate; methyl 2-(4'-(2-(2-methylpyrrolidin-1-yl)ethyl)biphenyl-4-ylcarboxamido)acetate; 2-(4'-(2-(2-methylpyrrolidin-1-yl)ethyl)biphenyl-4-ylcarboxamido) acetic acid; 2-methyl-2-(4'-(2-(2-methylpyrrolidin-1-yl)ethyl)biphenyl-4-ylcarboxamido)propanoic acid; 3-(4'-(2-(2-methylpyrrolidin-1-yl)ethyl)biphenyl-4-ylcarboxamido)propanoic acid; 5-(2-(4'-(2-(2-methylpyrrolidin-1-yl)ethyl)biphenyl-4-yl)ethyl)-1H-tetrazole; 4-(4'-(2-(2-methylpyrrolidin-1-yl)ethyl)biphenyl-4-yl)butanoic acid; and ethyl 4-(4'-(2-(2-methylpyrrolidin-1-yl)ethyl)biphenyl-4-yl)butanoate.

One aspect of the present invention encompasses every combination of one or more compounds selected from the compounds in Table A and pharmaceutically acceptable salts, solvates, and hydrates thereof.

TABLE A

| Cmpd No. | Chemical Structure | Chemical Name |
|---|---|---|
| 1 | 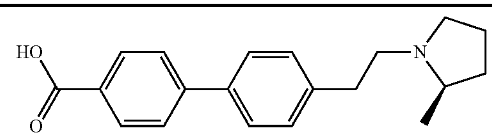 | (R)-4'-(2-(2-methylpyrrolidin-1-yl)ethyl)biphenyl-4-carboxylic acid |
| 2 | 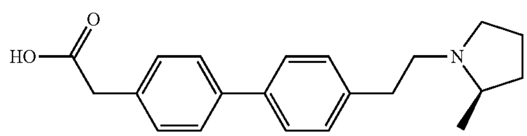 [SMILES: C[C@@H]1CCCN1CCc1ccc(-c2ccc(CC(=O)O)cc2)cc1] | (R)-2-(4'-(2-(2-methylpyrrolidin-1-yl)ethyl)biphenyl-4-yl)acetic acid |
| 3 | 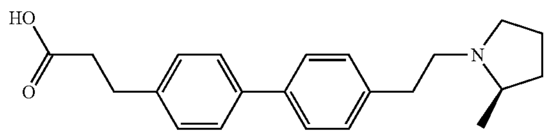 [SMILES: C[C@@H]1CCCN1CCc1ccc(-c2ccc(CCC(=O)O)cc2)cc1] | (R)-3-(4'-(2-(2-methylpyrrolidin-1-yl)ethyl)biphenyl-4-yl)propanoic acid |
| 4 | 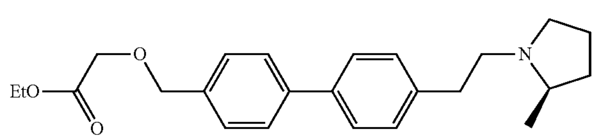 [SMILES: CCOC(=O)COCc1ccc(-c2ccc(CCN3CCC[C@H]3C)cc2)cc1] | (R)-ethyl 2-((4'-(2-(2-methylpyrrolidin-1-yl)ethyl)biphenyl-4-yl)methoxy)acetate |
| 5 | 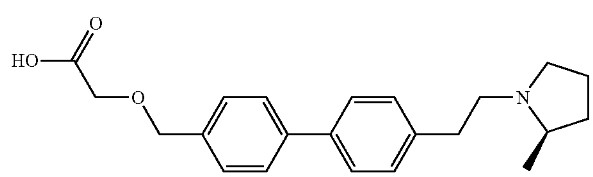 [SMILES: C[C@@H]1CCCN1CCc1ccc(-c2ccc(COCC(=O)O)cc2)cc1] | (R)-2-((4'-(2-(2-methylpyrrolidin-1-yl)ethyl)biphenyl-4-yl)methoxy)acetic acid |
| 6 | 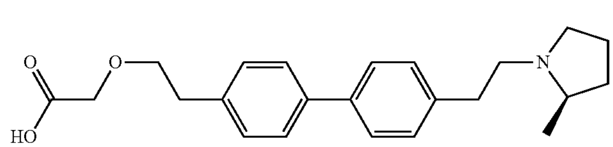 [SMILES: C[C@@H]1CCCN1CCc1ccc(-c2ccc(CCOCC(=O)O)cc2)cc1] | (R)-2-(2-(4'-(2-(2-methylpyrrolidin-1-yl)ethyl)biphenyl-4-yl)ethoxy)acetic acid |
| 7 | 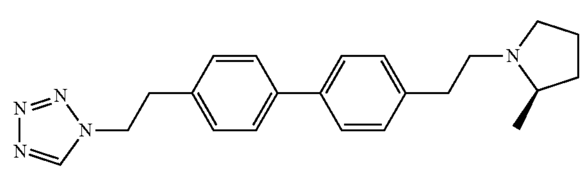 [SMILES: C[C@@H]1CCCN1CCc1ccc(-c2ccc(CCn3cnnn3)cc2)cc1] | (R)-1-(2-(4'-(2-(2-methylpyrrolidin-1-yl)ethyl)biphenyl-4-yl)ethyl)-1H-tetrazole |

| Cmpd No. | Chemical Structure | Chemical Name |
|---|---|---|
| 8 | 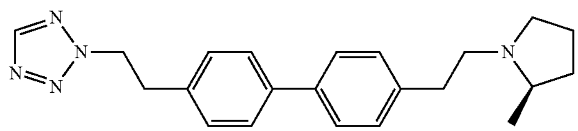 [SMILES: C[C@@H]1CCCN1CCc1ccc(-c2ccc(CCn3ncnn3)cc2)cc1] | (R)-2-(2-(4'-(2-(2-methylpyrrolidin-1-yl)ethyl)biphenyl-4-yl)ethyl)-2H-tetrazole |
| 9 | 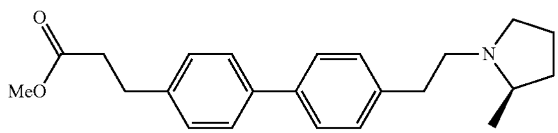 [SMILES: COC(=O)CCc1ccc(-c2ccc(CCN3CCC[C@H]3C)cc2)cc1] | (R)-methyl 3-(4'-(2-(2-methylpyrrolidin-1-yl)ethyl)biphenyl-4-yl)propanoate |
| 10 | 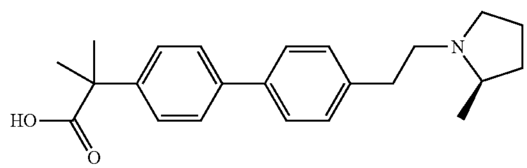 [SMILES: C[C@@H]1CCCN1CCc1ccc(-c2ccc(C(C)(C)C(=O)O)cc2)cc1] | (R)-2-methyl-2-(4'-(2-(2-methylpyrrolidin-1-yl)ethyl)biphenyl-4-yl)propanoic acid |
| 11 | 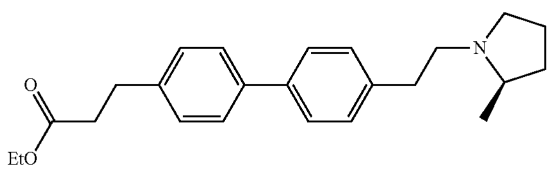 [SMILES: CCOC(=O)CCc1ccc(-c2ccc(CCN3CCC[C@H]3C)cc2)cc1] | (R)-ethyl 3-(4'-(2-(2-methylpyrrolidin-1-yl)ethyl)biphenyl-4-yl)propanoate |
| 12 | 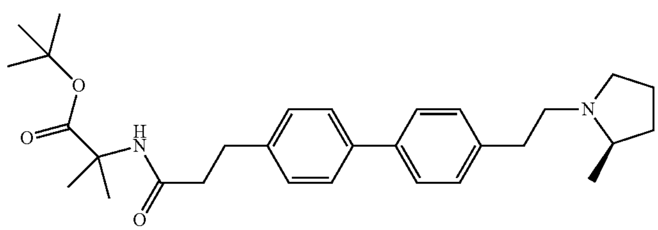 [SMILES: C[C@@H]1CCCN1CCc1ccc(-c2ccc(CCC(=O)NC(C)(C)C(=O)OC(C)(C)C)cc2)cc1] | (R)-tert-butyl 2-methyl-2-(3-(4'-(2-(2-methylpyrrolidin-1-yl)ethyl)biphenyl-4-yl)propanamido)propanoate |
| 13 | 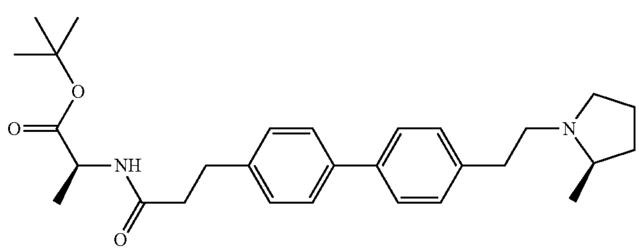 [SMILES: C[C@H](NC(=O)CCc1ccc(-c2ccc(CCN3CCC[C@H]3C)cc2)cc1)C(=O)OC(C)(C)C] | (S)-tert-butyl 2-(3-(4'-(2-((R)-2-methylpyrrolidin-1-yl)ethyl)biphenyl-4-yl)propanamido)propanoate |
| 14 | 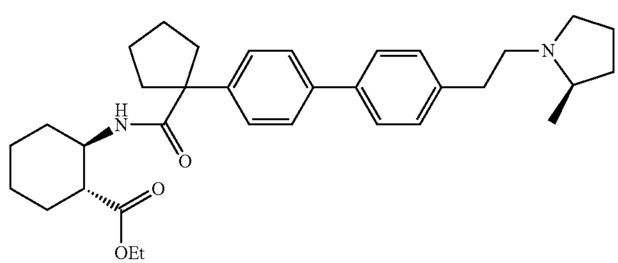 [SMILES: CCOC(=O)[C@@H]1CCCC[C@H]1NC(=O)C1(c2ccc(-c3ccc(CCN4CCC[C@H]4C)cc3)cc2)CCCC1] | (1R,2R)-ethyl 2-(1-(4'-(2-((R)-2-methylpyrrolidin-1-yl)ethyl)biphenyl-4-yl)cyclopentanecarboxamido)cyclohexanecarboxylate |

TABLE A-continued

| Cmpd No. | Chemical Structure | Chemical Name |
|---|---|---|
| 15 | 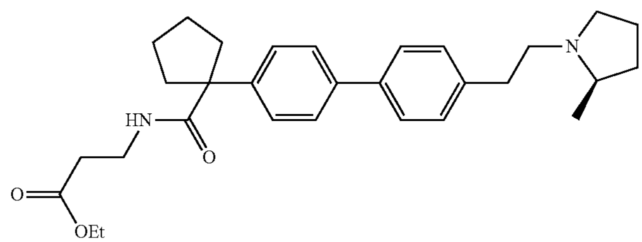 [SMILES: CCOC(=O)CCNC(=O)C1(c2ccc(-c3ccc(CCN4CCC[C@H]4C)cc3)cc2)CCCC1] | (R)-ethyl 3-(1-(4'-(2-(2-methylpyrrolidin-1-yl)ethyl)biphenyl-4-yl)cyclopentanecarboxamido)propanoate |
| 16 | 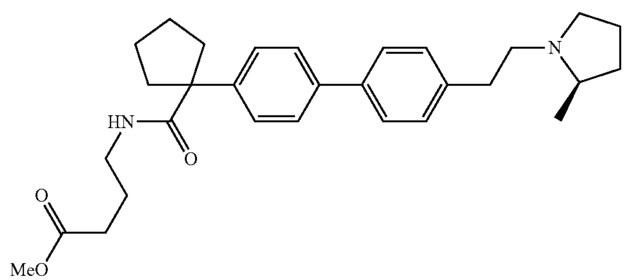 [SMILES: COC(=O)CCCNC(=O)C1(c2ccc(-c3ccc(CCN4CCC[C@H]4C)cc3)cc2)CCCC1] | (R)-methyl 4-(1-(4'-(2-(2-methylpyrrolidin-1-yl)ethyl)biphenyl-4-yl)cyclopentanecarboxamido)butanoate |
| 17 | 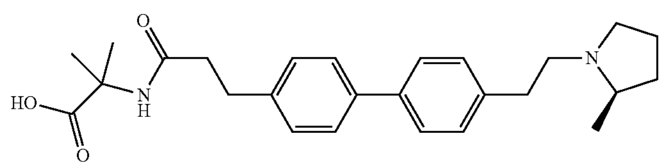 [SMILES: C[C@@H]1CCCN1CCc1ccc(-c2ccc(CCC(=O)NC(C)(C)C(=O)O)cc2)cc1] | (R)-2-methyl-2-(3-(4'-(2-(2-methylpyrrolidin-1-yl)ethyl)biphenyl-4-yl)propanamido)propanoic acid |
| 18 | 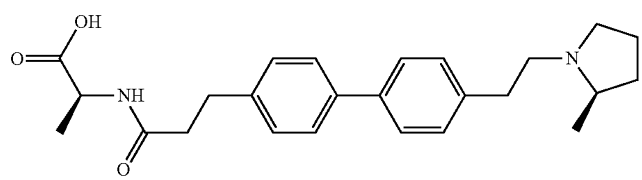 [SMILES: C[C@H](NC(=O)CCc1ccc(-c2ccc(CCN3CCC[C@H]3C)cc2)cc1)C(=O)O] | (S)-2-(3-(4'-(2-((R)-2-methylpyrrolidin-1-yl)ethyl)biphenyl-4-yl)propanamido)propanoic acid |
| 19 | 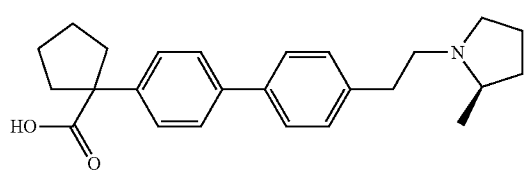 [SMILES: C[C@@H]1CCCN1CCc1ccc(-c2ccc(C3(C(=O)O)CCCC3)cc2)cc1] | (R)-1-(4'-(2-(2-methylpyrrolidin-1-yl)ethyl)biphenyl-4-yl)cyclopentanecarboxylic acid |
| 20 | 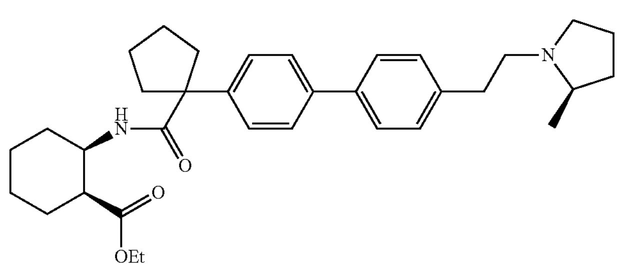 [SMILES: CCOC(=O)[C@H]1CCCC[C@H]1NC(=O)C1(c2ccc(-c3ccc(CCN4CCC[C@H]4C)cc3)cc2)CCCC1] | (1R,2S)-ethyl 2-(1-(4'-(2-((R)-2-methylpyrrolidin-1-yl)ethyl)biphenyl-4-yl)cyclopentanecarboxamido)cyclohexanecarboxylate |
| 21 | 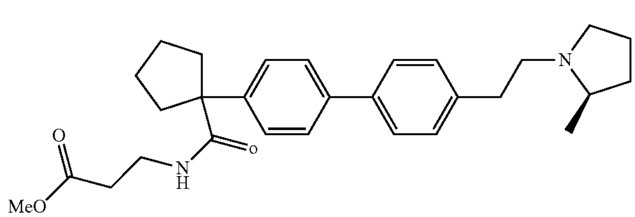 | (R)-methyl 3-(1-(4'-(2-(2-methylpyrrolidin-1-yl)ethyl)biphenyl-4-yl)cyclopentanecarboxamido)propanoate |

TABLE A-continued

| Cmpd No. | Chemical Structure | Chemical Name |
|---|---|---|
| 22 | 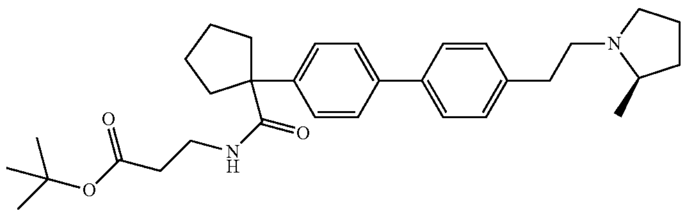 [SMILES: C[C@@H]1CCCN1CCc1ccc(-c2ccc(C3(C(=O)NCCC(=O)OC(C)(C)C)CCCC3)cc2)cc1] | (R)-tert-butyl 3-(1-(4'-(2-(2-methylpyrrolidin-1-yl)ethyl)biphenyl-4-yl)cyclopentanecarboxamido)propanoate |
| 23 | 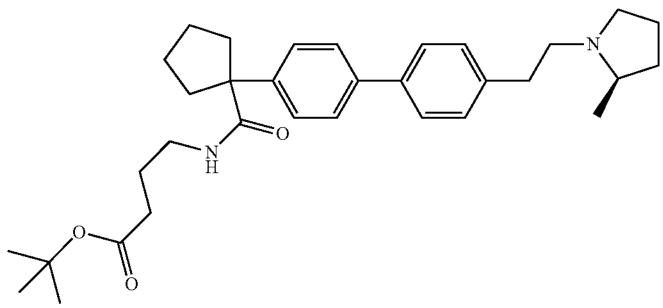 [SMILES: C[C@@H]1CCCN1CCc1ccc(-c2ccc(C3(C(=O)NCCCC(=O)OC(C)(C)C)CCCC3)cc2)cc1] | (R)-tert-butyl 4-(1-(4'-(2-(2-methylpyrrolidin-1-yl)ethyl)biphenyl-4-yl)cyclopentanecarboxamido)butanoate |
| 24 | 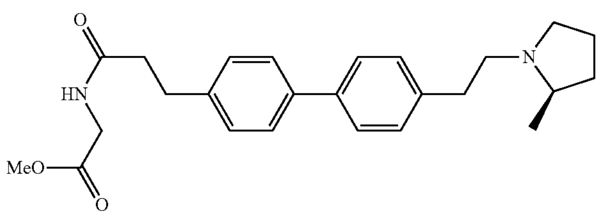 [SMILES: COC(=O)CNC(=O)CCc1ccc(-c2ccc(CCN3CCC[C@H]3C)cc2)cc1] | (R)-methyl 2-(3-(4'-(2-(2-methylpyrrolidin-1-yl)ethyl)biphenyl-4-yl)propanamido)acetate |
| 25 | 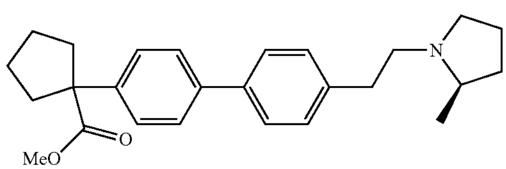 [SMILES: COC(=O)C1(c2ccc(-c3ccc(CCN4CCC[C@H]4C)cc3)cc2)CCCC1] | (R)-methyl 1-(4'-(2-(2-methylpyrrolidin-1-yl)ethyl)biphenyl-4-yl)cyclopentanecarboxylate |
| 26 | 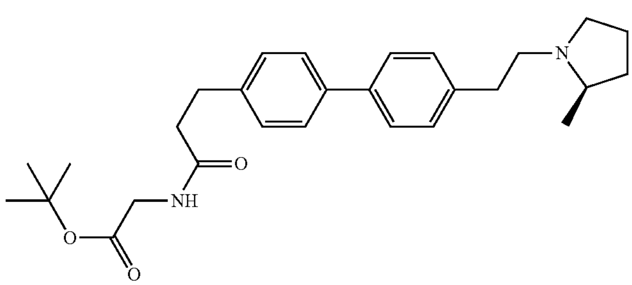 [SMILES: C[C@@H]1CCCN1CCc1ccc(-c2ccc(CCC(=O)NCC(=O)OC(C)(C)C)cc2)cc1] | (R)-tert-butyl 2-(3-(4'-(2-(2-methylpyrrolidin-1-yl)ethyl)biphenyl-4-yl)propanamido)acetate |
| 27 | 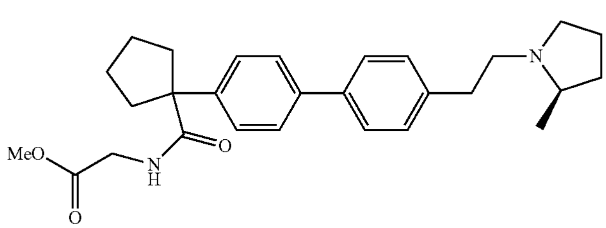 [SMILES: COC(=O)CNC(=O)C1(c2ccc(-c3ccc(CCN4CCC[C@H]4C)cc3)cc2)CCCC1] | (R)-methyl 2-(1-(4'-(2-(2-methylpyrrolidin-1-yl)ethyl)biphenyl-4-yl)cyclopentanecarboxamido)acetate |

TABLE A-continued

| Cmpd No. | Chemical Structure | Chemical Name |
|---|---|---|
| 28 | 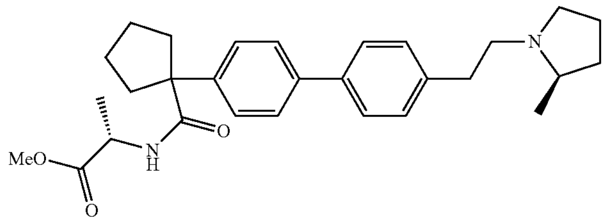 [SMILES: COC(=O)[C@H](C)NC(=O)C1(c2ccc(-c3ccc(CCN4CCC[C@H]4C)cc3)cc2)CCCC1] | (S)-methyl 2-(1-(4'-(2-((R)-2-methylpyrrolidin-1-yl)ethyl)biphenyl-4-yl)cyclopentanecarboxamido)propanoate |
| 29 | 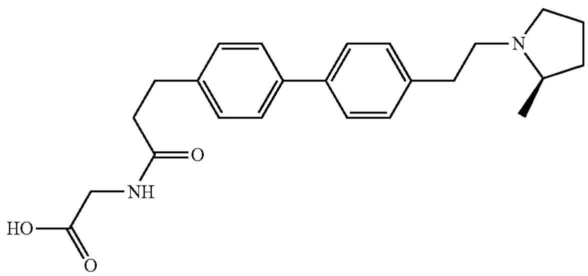 [SMILES: C[C@@H]1CCCN1CCc1ccc(-c2ccc(CCC(=O)NCC(=O)O)cc2)cc1] | (R)-2-(3-(4'-(2-(2-methylpyrrolidin-1-yl)ethyl)biphenyl-4-yl)propanamido)acetic acid |
| 30 | 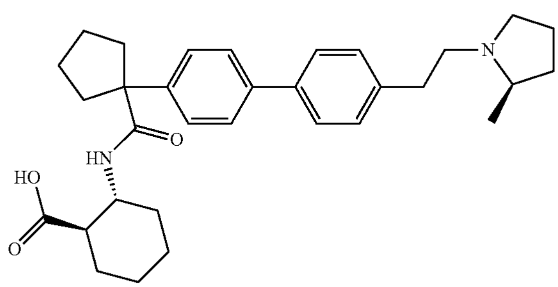 [SMILES: C[C@@H]1CCCN1CCc1ccc(-c2ccc(C3(C(=O)N[C@@H]4CCCC[C@H]4C(=O)O)CCCC3)cc2)cc1] | (1R,2R)-2-(1-(4'-(2-((R)-2-methylpyrrolidin-1-yl)ethyl)biphenyl-4-yl)cyclopentanecarboxamido)cyclohexanecarboxylic acid |
| 31 | 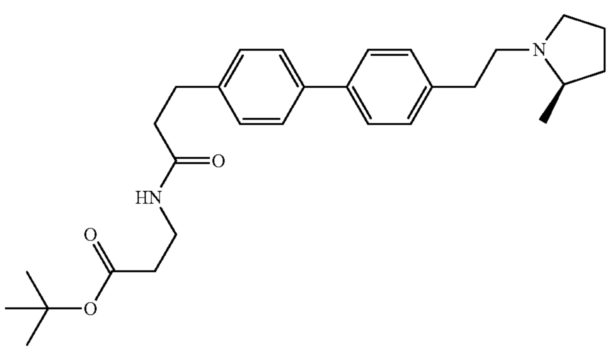 [SMILES: C[C@@H]1CCCN1CCc1ccc(-c2ccc(CCC(=O)NCCC(=O)OC(C)(C)C)cc2)cc1] | (R)-tert-butyl 3-(3-(4'-(2-(2-methylpyrrolidin-1-yl)ethyl)biphenyl-4-yl)propanamido)propanoate |
| 32 | 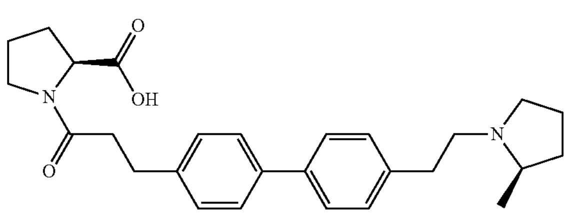 [SMILES: C[C@@H]1CCCN1CCc1ccc(-c2ccc(CCC(=O)N3CCC[C@H]3C(=O)O)cc2)cc1] | (S)-1-(3-(4'-(2-((R)-2-methylpyrrolidin-1-yl)ethyl)biphenyl-4-yl)propanoyl)pyrrolidine-2-carboxylic acid |

TABLE A-continued

| Cmpd No. | Chemical Structure | Chemical Name |
|---|---|---|
| 33 | 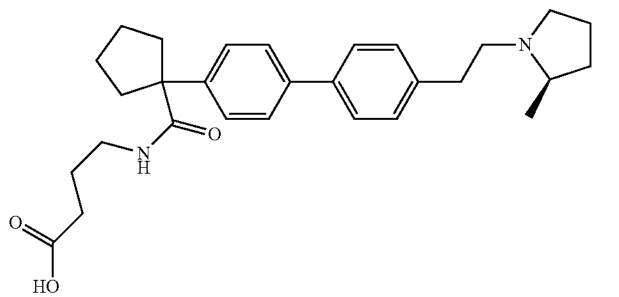 [SMILES: C[C@@H]1CCCN1CCc1ccc(-c2ccc(C3(C(=O)NCCCC(=O)O)CCCC3)cc2)cc1] | (R)-4-(1-(4'-(2-(2-methylpyrrolidin-1-yl)ethyl)biphenyl-4-yl)cyclopentanecarboxamido)butanoic acid |
| 34 | 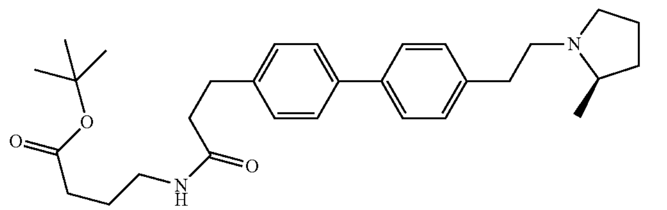 [SMILES: C[C@@H]1CCCN1CCc1ccc(-c2ccc(CCC(=O)NCCCC(=O)OC(C)(C)C)cc2)cc1] | (R)-tert-butyl 4-(3-(4'-(2-(2-methylpyrrolidin-1-yl)ethyl)biphenyl-4-yl)propanamido)butanoate |
| 35 | 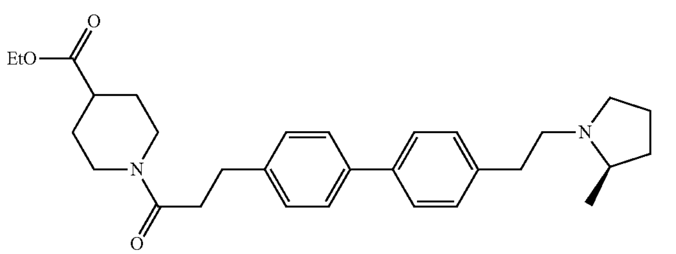 [SMILES: CCOC(=O)C1CCN(C(=O)CCc2ccc(-c3ccc(CCN4CCC[C@H]4C)cc3)cc2)CC1] | (R)-ethyl 1-(3-(4'-(2-(2-methylpyrrolidin-1-yl)ethyl)biphenyl-4-yl)propanoyl)piperidine-4-carboxylate |
| 36 | 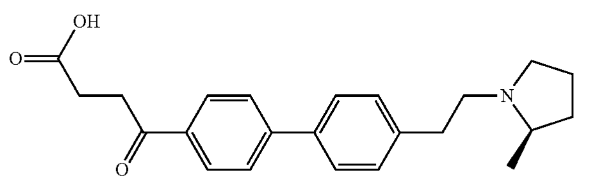 [SMILES: C[C@@H]1CCCN1CCc1ccc(-c2ccc(C(=O)CCC(=O)O)cc2)cc1] | (R)-4-(4'-(2-(2-methylpyrrolidin-1-yl)ethyl)biphenyl-4-yl)-4-oxobutanoic acid |
| 37 | 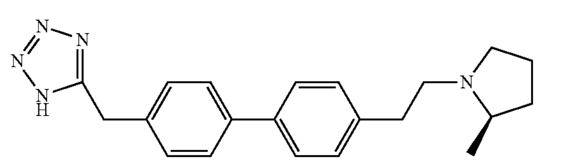 [SMILES: C[C@@H]1CCCN1CCc1ccc(-c2ccc(Cc3nnn[nH]3)cc2)cc1] | (R)-5-((4'-(2-(2-methylpyrrolidin-1-yl)ethyl)biphenyl-4-yl)methyl)-1H-tetrazole |
| 38 | 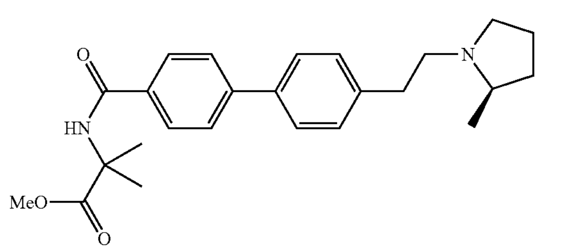 [SMILES: COC(=O)C(C)(C)NC(=O)c1ccc(-c2ccc(CCN3CCC[C@H]3C)cc2)cc1] | (R)-methyl 2-methyl-2-(4'-(2-(2-methylpyrrolidin-1-yl)ethyl)biphenyl-4-ylcarboxamido)propanoate |

TABLE A-continued

| Cmpd No. | Chemical Structure | Chemical Name |
|---|---|---|
| 39 | 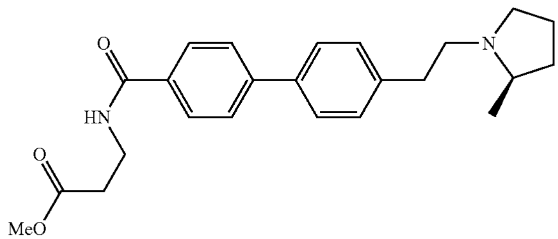 [SMILES: COC(=O)CCNC(=O)c1ccc(-c2ccc(CCN3CCC[C@H]3C)cc2)cc1] | (R)-methyl 3-(4'-(2-(2-methylpyrrolidin-1-yl)ethyl)biphenyl-4-ylcarboxamido)propanoate |
| 40 | 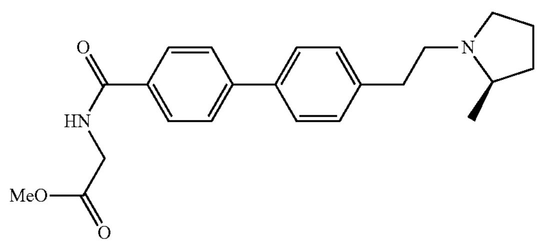 [SMILES: COC(=O)CNC(=O)c1ccc(-c2ccc(CCN3CCC[C@H]3C)cc2)cc1] | (R)-methyl 2-(4'-(2-(2-methylpyrrolidin-1-yl)ethyl)biphenyl-4-ylcarboxamido)acetate |
| 41 | 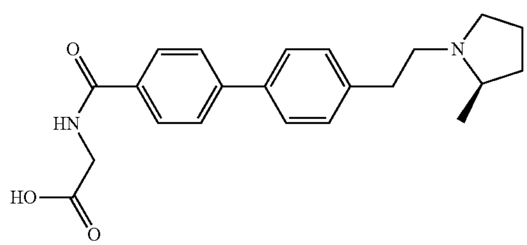 [SMILES: C[C@@H]1CCCN1CCc1ccc(-c2ccc(C(=O)NCC(=O)O)cc2)cc1] | (R)-2-(4'-(2-(2-methylpyrrolidin-1-yl)ethyl)biphenyl-4-ylcarboxamido)acetic acid |
| 42 | 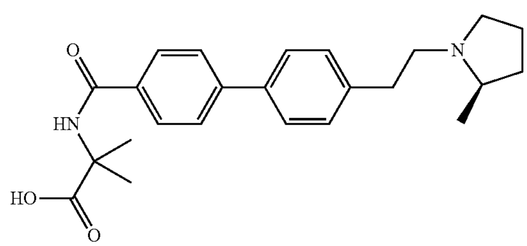 [SMILES: C[C@@H]1CCCN1CCc1ccc(-c2ccc(C(=O)NC(C)(C)C(=O)O)cc2)cc1] | (R)-2-methyl-2-(4'-(2-(2-methylpyrrolidin-1-yl)ethyl)biphenyl-4-ylcarboxamido)propanoic acid |
| 43 | 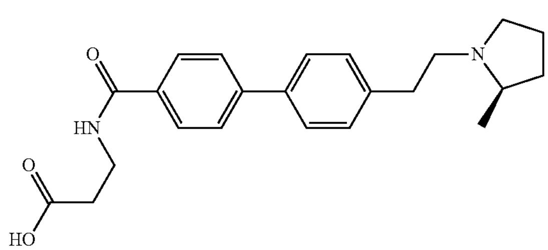 [SMILES: C[C@@H]1CCCN1CCc1ccc(-c2ccc(C(=O)NCCC(=O)O)cc2)cc1] | (R)-3-(4'-(2-(2-methylpyrrolidin-1-yl)ethyl)biphenyl-4-ylcarboxamido)propanoic acid |
| 44 | 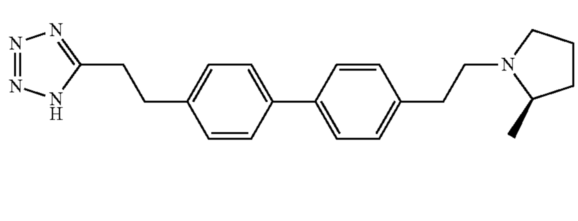 [SMILES: C[C@@H]1CCCN1CCc1ccc(-c2ccc(CCc3nnn[nH]3)cc2)cc1] | (R)-5-(2-(4'-(2-(2-methylpyrrolidin-1-yl)ethyl)biphenyl-4-yl)ethyl)-1H-tetrazole |

TABLE A-continued

| Cmpd No. | Chemical Structure | Chemical Name |
| --- | --- | --- |
| 45 | 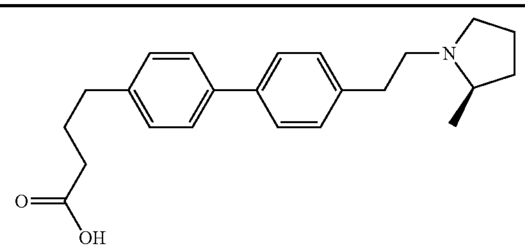 | (R)-4-(4'-(2-(2-methylpyrrolidin-1-yl)ethyl)biphenyl-4-yl)butanoic acid |
| 46 | 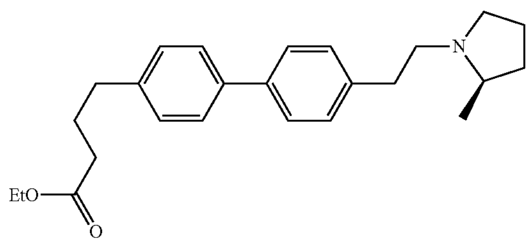 [SMILES: CCOC(=O)CCCc1ccc(-c2ccc(CCN3CCC[C@H]3C)cc2)cc1] | (R)-ethyl 4-(4'-(2-(2-methylpyrrolidin-1-yl)ethyl)biphenyl-4-yl)butanoate |

Additionally, individual compounds and chemical genera of the present invention, for example those compounds found in Table A including diastereoisomers and enantiomers thereof, encompass all pharmaceutically acceptable salts, solvates, and particularly hydrates, thereof.

The compounds of Formula (Ia) may be prepared according to relevant published literature procedures that are used by one skilled in the art. Exemplary reagents and procedures for these reactions appear hereinafter in the working Examples. Protection and deprotection may be carried out by procedures generally known in the art (see, for example, Greene, T. W. and Wuts, P. G. M., *Protecting Groups in Organic Synthesis*, 3$^{rd}$ Edition, 1999 [Wiley]).

It is understood that the present invention embraces each diastereoisomer, each enantiomer and mixtures thereof of each compound and generic formulae disclosed herein just as if they were each individually disclosed with the specific stereochemical designation for each chiral carbon. Separation of the individual isomers (such as, by chiral HPLC, recrystallization of diastereoisomeric mixtures and the like) or selective synthesis (such as, by enantiomeric selective syntheses and the like) of the individual isomers is accomplished by application of various methods which are well known to practitioners in the art.

Indications and Methods of Prophylaxis and/or Treatment

Histamine [2-(imidazol-4-yl)ethylamine] exerts its physiological effects through four distinct G-protein coupled receptors (GPCRs), termed H1, H2, H3 and H4. The histamine H3 receptor was first identified in 1983, when it was determined that the H3 receptor acted as an autoreceptor controlling both the synthesis and release of histamine (see: Arrang et al. *Nature* 1983, 302, 832-7). At least four human and three rat splice variants have proven functional activity in pharmacological assays (Passani et al., *Trends in Pharmacol. Sci.* 2004, 25, 618-625). Rat and human H3 receptors also show constitutive activity which means that they can transduce a signal even in the absence of a ligand. Histamine H3 receptors also function as heteroceptors, modulating the release of a number of other transmitter substances including serotonin, acetylcholine, dopamine and noradrenaline (see: Brown et al. *Prog. Neurobiol.* 2001, 63, 637-672). Thus, there are a number of therapeutic applications for ligands which target the H3 receptor, where the ligand functions as either an antagonist or inverse agonist (for reviews see: Leurs et al. *Nat. Rev. Drug. Discov.* 2005, 4, 107-120; Passani et al. *Trends Pharmacol. Sci.* 2004, 25, 618-625).

Accordingly, preclinical studies have identified a number of indications which are amenable to treatment with H3 receptor antagonists and inverse agonists, such as compounds of the present invention. The compounds disclosed herein are believed to be useful in the treatment and/or prevention of several diseases and disorders, and in the amelioration of symptoms thereof. These compounds can be used alone or in combination with other compounds for the treatment and/or prevention of diseases and disorders. Without limitation, these diseases and disorders include the following.

Histamine H3 receptor antagonists have been shown to increase wakefulness (e.g. Lin J. S. et al. *Brain Research* 1990, 523, 325-330). This effect demonstrates that H3 receptor antagonists can be useful for disorders of sleep and wakefulness (Parmentier et al. *J. Neurosci.* 2002, 22, 7695-7711; Ligneau et al. *J. Pharmacol. Exp. Ther.* 1998, 287, 658-666). For example, H3 receptor antagonists and inverse agonists can be used to treat the somnolence syndrome associated with different pathological conditions, for example, sleep apnea and Parkinson's disease or circumstances associated with lifestyle, for example, daytime somnolence from sleep deprivation as a result of nocturnal jobs, overwork, or jet-lag (see Passani et al., *Trends Pharmacol. Sci.* 2004, 25, 618-625). Somnolence is one of the major problems of public health because of its high prevalence (19-37% of the general population) and risk for causing work and traffic accidents.

Sleep apnea (alternatively sleep apnoea) is a common sleep disorder characterized by brief interruptions of breathing during sleep. These episodes, called apneas, last 10 seconds or more and occur repeatedly throughout the night. People with sleep apnea partially awaken as they struggle to breathe, but in the morning they may not be aware of the disturbances in their sleep. The most common type of sleep apnea is obstructive sleep apnea (OSA), caused by relaxation of soft tissue in the back of the throat that blocks the passage of air. Central sleep apnea (CSA) is caused by irregularities in the brain's normal signals to breathe. The hallmark symptom of the disorder is excessive daytime sleepiness. Additional symptoms of sleep apnea include restless sleep, loud snoring (with periods of silence followed by gasps), falling asleep during the day, morning headaches, trouble concentrating, irritability, forgetfulness, mood or behaviour changes, weight gain, increased heart rate, anxiety, and depression.

Few drug-based treatments of obstructive sleep apnea are known despite over two decades of research and tests. Oral administration of the methylxanthine theophylline (chemically similar to caffeine) can reduce the number of episodes of apnea, but can also produce side effects such as palpitations and insomnia. Theophylline is generally ineffective in adults with OSA, but is sometimes used to treat CSA, and infants and children with apnea. In 2003 and 2004, some neuroactive drugs, particularly modern-generation antidepressants including mirtazapine, have been reported to reduce incidences of obstructive sleep apnea. When other treatments do not completely treat the OSA, drugs are sometimes prescribed to treat a patient's daytime sleepiness or somnolence. These range from stimulants such as amphetamines to modern anti-narcoleptic medicines. The drug modafinil is seeing increased use in this role as of 2004.

In addition, for example, H3 receptor antagonists and inverse agonists can be used to treat narcolepsy (Tedford et al. *Soc. Neurosci. Abstr.* 1999, 25, 460.3). Narcolepsy is a neurological condition most often characterized by Excessive Daytime Sleepiness (EDS), episodes of sleep and disorder of REM or rapid eye movement sleep. The main characteristic of narcolepsy is overwhelming Excessive Daytime Sleepiness (EDS), even after adequate nighttime sleep. A person with narcolepsy is likely to become drowsy or to fall asleep, often at inappropriate times and places. In addition, nighttime sleep may be fragmented with frequent wakenings. Classic symptoms of narcolepsy include, for example, cataplexy which is sudden episodes of loss of muscle function, ranging from slight weakness (such as limpness at the neck or knees, sagging facial muscles, or inability to speak clearly) to complete body collapse. Episodes may be triggered by sudden emotional reactions such as laughter, anger, surprise, or fear, and may last from a few seconds to several minutes. Another symptom of narcolepsy is sleep paralysis, which is the temporary inability to talk or move when waking up. Other symptoms include, for example, hypnagogic hallucinations which are vivid, often frightening, dream-like experiences that occur while dozing, falling asleep and/or while awakening, and automatic behaviour which occurs when a person continues to function (talking, putting things away, etc.) during sleep episodes, but awakens with no memory of performing such activities. Daytime sleepiness, sleep paralysis, and hypnagogic hallucinations also occur in people who do not have narcolepsy, such as in people who are suffering from extreme lack of sleep. Cataplexy is generally considered unique to narcolepsy.

Currently the treatments available for narcolepsy treat the symptoms, but not the underlying cause. For cataplexy and REM-sleep symptoms, antidepressant medications and other drugs that suppress REM sleep are prescribed. The drowsiness is normally treated using stimulants such as methylphenidate (Ritalin), amphetamines (Adderall), dextroamphetamine (Dexedrine), methamphetamine (Desoxyn), modafinil (Provigil), etc. Other medications used are codeine and selegiline. The cataplexy is treated using clomipramine, imipramine, or protriptyline but this need only be done in severe cases. The drug gamma-hydroxybutyrate (GHB) (Xyrem) is approved in the USA by the Food and Drug Administration to treat both the cataplexy and excessive daytime sleepiness associated with narcolepsy.

Interestingly, modafinil (Provigil) has recently been shown to increase hypothalamic histamine release (Ishizuka et al. *Neurosci. Lett.* 2003, 339, 143-146).

In addition, recent studies using the classic Doberman model of narcolepsy with a non-imidazole H3 receptor antagonist showed that a H3 receptor antagonist can reduce the number of cataplectic attacks and the duration of the attacks (Carruthers *Ann. Meet. Eur. Histamine Res. Soc.* 2004, Abs. p 31).

In summary, H3 receptor antagonists and inverse agonists can be used for the treatment and/or prevention of conditions associated with excessive daytime sleepiness such as hypersomnia, narcolepsy, sleep apnea, time zone change disorder, and other disorders which are associated with excessive daytime sleepiness such as fibromyalgia, and multiple sclerosis (Parmentier et al., *J. Neurosci.* 2002, 22, 7695-7711; Ligneau et al. *J. Pharmacol. Exp. Ther.* 1998, 287, 658-666). Other conditions include excessive sleepiness due to shift-work, medical disorders, psychiatric disorders, narcolepsy, primary hypersomnia, and the like. Histamine H3 receptor antagonists and inverse agonists can also be used occasionally to promote wakefulness or vigilance in shift workers, sleep deprivation, post anesthesia grogginess, drowsiness as a side effect from a medication, military use and the like.

In addition, wakefulness is a prerequisite for several brain functions including attention, learning, and memory and is required for appropriate behaviours in response to environmental challenges. Histamine H3 receptor antagonists and inverse agonists have been shown to improve cognitive performance in various animal models (Hancock and Fox in *Milestones in Drug Therapy*, ed. Buccafusco, 2003). These compounds can be used as pro-cognitive agents and can increase vigilance. Therefore, H3 receptor antagonists and inverse agonists can be used in aging or degenerative disorders in which vigilance, attention and memory are impaired, for example, as in Alzheimer's disease or other dementias.

Alzheimer's disease (AD), a neurodegenerative disorder, is the most common cause of dementia. It is characterized clinically by progressive cognitive deterioration together with neuropsychiatric symptoms and behavioural changes. The most striking early symptom is memory loss, which usually manifests as minor forgetfulness that becomes steadily more pronounced with illness progression, with relative preservation of older memories. As the disorder progresses, cognitive (intellectual) impairment extends to the domains of language, skilled movements, recognition and functions closely related to the frontal and temporal lobes of the brain such as decision-making and planning. There is currently no cure for AD, although there are drugs which offer symptomatic benefit, specifically with respect to short-term memory impairment. These drugs include acetylcholinesterase inhibitors such as donepezil (Aricept), galantamine (Razadyne) and rivastigmine (Exelon) and NMDA antagonists such as memantine.

Histamine H3 receptor antagonists and inverse agonists can be used to treat or prevent cognitive disorders (Passani et al. *Trends Pharmacol. Sci.* 2004, 25, 618-625), epilepsy (Vohora et al. *Pharmacol. Biochem. Behav.* 2001, 68, 735-741), depression (Perez-Garcia et al. *Psychopharmacol.* 1999, 142, 215-220), attention deficit hyperactivity disorder (ADHD), (Fox et al. *Behav. Brain Res.* 2002, 131, 151-61), and schizophrenia (Fox et al. *J. Pharmacol. Exp. Ther.* 2005, 313, 176-190). These indications are described briefly below. For additional information, see reviews by Leurs et al., *Nat. Rev. Drug. Discov.* 2005, 4, 107-120, and Vohora *Investigational Drugs* 2004, 7, 667-673). Histamine H3 receptor antagonists or inverse agonists can also be used as a novel therapeutic approach to restore cortical activation in comatose or brain-traumatized patients (Passani et al., *Trends in Pharmacol. Sci.* 2004, 25, 618-625).

As stated above, H3 receptor antagonists and inverse agonists can be used to treat or prevent epilepsy. Epilepsy (often referred to as a seizure disorder) is a chronic neurological condition characterized by recurrent unprovoked seizures. In terms of their pattern of activity, seizures may be described as either partial (focal) or generalized. Partial seizures only involve a localized part of the brain, whereas generalized seizures involve the entire cortex. There are many different epilepsy syndromes, each presenting with its own unique combination of seizure type, typical age of onset, EEG findings, treatment, and prognosis. Some common seizure syndromes include, for example, infantile spasms (West syndrome), childhood absence epilepsy, and benign focal epilepsy of childhood (Benign Rolandic epilepsy), juvenile myoclonic epilepsy, temporal lobe epilepsy, frontal lobe epilepsy and Lennox-Gastaut syndrome.

Compounds of the present invention can be used in combination with various known drugs. For example, compounds of the present invention can be used with one or more drugs that prevent seizures or reduce seizure frequency: these include carbamazepine (common brand name Tegretol), clobazam (Frisium), clonazepam (Klonopin), ethosuximide (Zarontin), felbamate (Felbatol), fosphenytoin (Cerebyx), flurazepam (Dalmane), gabapentin (Neurontin), lamotrigine (Lamictal), levetiracetam (Keppra), oxcarbazepine (Trileptal), mephenytoin (Mesantoin), phenobarbital (Luminal), phenytoin (Dilantin), pregabalin (Lyrica), primidone (Mysoline), sodium valproate (Epilim), tiagabine (Gabitril), topiramate (Topamax), valproate semisodium (Depakote), valproic acid (Depakene, Convulex), and vigabatrin (Sabril). Other drugs are commonly used to abort an active seizure or interrupt a seizure flurry; these include diazepam (Valium) and lorazepam (Ativan). Drugs used only in the treatment of refractory status epilepticus include paraldehyde (Paral) and pentobarbital (Nembutal).

As stated above, a H3 receptor antagonist or inverse agonist can be used as the sole agent of treatment or can be used in combination with other agents. For example, Vohora et al. show that a H3 receptor antagonist can work as an anti-epilepsy, anti-seizure drug and also showed effect with sub-effective doses of the H3 receptor antagonist in combination with sub-effective doses of known anti-epileptic drugs (Vohora et al. *Pharmacol. Biochem. Behav.* 2001, 68, 735-741).

Perez-Garcia et al. (*Psychopharmacol.* 1999, 142, 215-220) tested the ability of a H3 receptor agonist and antagonist on experimental mouse models of anxiety (elevated plus-maze) and depression (forced swimming test). They found that while the compounds did not have a significant effect on the model of anxiety, an H3 receptor antagonist did have a significant dose-dependent effect in the model of depression. Thus, H3 receptor antagonists or inverse agonists can have antidepressant effects.

Clinical depression is a state of sadness or melancholia that has advanced to the point of being disruptive to an individual's social functioning and/or activities of daily living. Clinical depression affects about 16% of the population on at least one occasion in their lives. Clinical depression is currently the leading cause of disability in the U.S. as well as other countries, and is expected to become the second leading cause of disability worldwide (after heart disease) by the year 2020, according to the World Health Organization.

Compounds of the present invention can be used in combination with various known drugs. For example, compounds of the present invention can be used with one or more of the drugs currently available that can relieve the symptoms of depression. They include, for example, monoamine oxidase inhibitors (MAOIs) such as Nardil or Moclobemide (Manerix), tricyclic antidepressants, selective serotonin reuptake inhibitors (SSRIs) such as fluoxetine (Prozac), paroxetine (Paxil), escitalopram (Lexapro), and sertraline (Zoloft), norepinephrine reuptake inhibitors such as reboxetine (Edronax), and serotonin-norepinephrine reuptake inhibitors (SNRIs) such as venlafaxine (Effexor) and duloxetine (Cymbalta).

As stated above, H3 receptor antagonists and inverse agonists can be used to treat or prevent attention deficit hyperactivity disorder (ADHD). According to the Diagnostic and Statistical Manual of Mental Disorders-IV-TR, ADHD is a developmental disorder that arises in childhood, in most cases before the age of 7 years, is characterized by developmentally inappropriate levels of inattention and/or hyperactive-impulsive behavior, and results in impairment in one or more major life activities, such as family, peer, educational, occupational, social, or adaptive functioning. ADHD can also be diagnosed in adulthood.

The first-line medications used to treat ADHD are mostly stimulants, which work by stimulating the areas of the brain responsible for focus, attention, and impulse control. The use of stimulants to treat a syndrome often characterized by hyperactivity is sometimes referred to as a paradoxical effect, but there is no real paradox in that stimulants activate brain inhibitory and self-organizing mechanisms permitting the individual to have greater self-regulation. The stimulants used include, for example, methylphenidate (sold as Ritalin, Ritalin SR and Ritalin LA), Metadate, Metadate ER, Metadate CD, Concerta, Focalin, Focalin XR or Methylin. The stimulants also include, for example, amphetamines such dextroamphetamine, sold as Dexedrine, Dexedrine Spansules, Adderall, and Adderall XR, a trade name for a mixture of dextroamphetamine and laevoamphetamine salts, methamphetamine sold as Desoxyn, bupropion, a dopamine and norepinephrine reuptake inhibitor, marketed under the brand name Wellbutrin. A non-stimulant medication to treat ADHD is Atomoxetine (sold as Strattera) a norepinephrine reuptake inhibitor. Other drugs sometimes used for ADHD include, for example, benzphetamine, Provigil/Alertec/modafinil and clonidine. Recently it has been reported that in a rat pup model for ADHD, a H3 receptor antagonist was at least as effective as methylphenidate (Ritalin) (Hancock and Fox in *Milestones in Drug Therapy*, ed. Buccafusco, 2003). Compounds of the present invention can be used in combination with various known drugs. For example, compounds of the present invention can be used with one or more of the drugs used to treat ADHD and related disorders.

As stated above, H3 receptor antagonists and inverse agonists can be used to treat or prevent schizophrenia. Schizophrenia is a psychiatric diagnosis that describes a mental disorder characterized by impairments in the perception or expression of reality and by significant social or occupational dysfunction. A person experiencing untreated schizophrenia is typically characterized as demonstrating disorganized thinking, and as experiencing delusions or auditory hallucinations. Although the disorder is primarily thought to affect cognition, it can also contribute to chronic problems with behavior and emotion. Schizophrenia is often described in terms of "positive" and "negative" symptoms. Positive symptoms include delusions, auditory hallucinations and thought disorder, and are typically regarded as manifestations of psychosis. Negative symptoms are so named because they are considered to be the loss or absence of normal traits or abilities, and include features such as flat, blunted or constricted affect and emotion, poverty of speech and lack of motivation.

Some models of schizophrenia include formal thought disorder and planning difficulties in a third group, a "disorganization syndrome."

The first line pharmacological therapy for schizophrenia is usually the use of antipsychotic medication. Antipsychotic drugs are only thought to provide symptomatic relief from the positive symptoms of psychosis. The newer atypical antipsychotic medications (such as clozapine, risperidone, olanzapine, quetiapine, ziprasidone and aripiprazole) are usually preferred over older typical antipsychotic medications (such as chlorpromazine and haloperidol) due to their favorable side-effect profile. While the atypical antipsychotics are associated with less extra pyramidal side-effects and tardive dyskinesia than the conventional antipsychotics, some of the agents in this class (especially olanzapine and clozapine) appear to be associated with metabolic side effects such as weight gain, hyperglycemia and hypertriglyceridemia that must be considered when choosing appropriate pharmacotherapy.

Histamine H3 receptor antagonists or inverse agonists can be used to treat obesity (Hancock, *Curr. Opin. Investig. Drugs* 2003, 4, 1190-1197). The role of neuronal histamine in food intake has been established for many years and neuronal histamine release and/or signalling has been implicated in the anorectic actions of known mediators in the feeding cycle such as leptin, amylin and bombesin. In the brain, the H3 receptor is implicated in the regulation of histamine release in the hypothalamus. Moreover, in situ hybridization studies have revealed H3 receptor mRNA expression in rat brown adipose tissue, indicating a role in the regulation of thermogenesis (Karlstedt et al., *Mol. Cell. Neurosci.* 2003, 24, 614-622). Furthermore, H3 receptor antagonists have been investigated in various preclinical models of obesity and have shown to be effective in reducing food intake, reducing weight, and decreasing total body fat in mice (Hancock, et al. *Eur. J. Pharmacol.* 2004, 487, 183-197). The most common drugs used for the treatment of obesity are sibutramine (Meridia) and orlistat (Xenical), both of which have limited effectiveness and significant side effects. Therefore, novel anti-obesity agents, such as H3 receptor antagonists or inverse agonists, are needed.

Histamine H3 receptor antagonists or inverse agonists can also be used to treat upper airway allergic responses (U.S. Pat. Nos. 5,217,986; 5,352,707 and 5,869,479) including allergic rhinitis and nasal congestion. Allergic rhinitis is a frequently occurring chronic disease that affects a large number of people. Recent analysis of H3 receptor expression in the periphery by quantitative PCR revealed that H3 receptor mRNA is abundantly expressed in human nasal mucosa (Varty et al. *Eur. J. Pharmacol.* 2004, 484, 83-89). In addition, in a cat model of nasal decongestion, a combination of H3 receptor antagonists with the H1 receptor antagonist chlorpheniramine resulted in significant nasal decongestion without the hypertensive effect seen with adrenergic agonists. (McLeod et al. *Am. J. Rhinol.* 1999, 13, 391-399). Thus, H3 receptor antagonists or inverse agonists can be used alone or in combination with H1 receptor blockage for the treatment of allergic rhinitis and nasal congestion.

Histamine H3 receptor antagonists or inverse agonists have therapeutic potential for the treatment of pain (Medhurst et al. *Biochemical Pharmacology* (2007), 73(8), 1182-1194).

Itch, or pruritus, is the unpleasant sensation that leads to a desire to scratch (for reviews, see Journal of Investigative Dermatology (2006) 126: 1705-1718; and Lancet (2003) 361: 690-94). It is a common and distressing symptom in a variety of conditions and diseases. Itch typically occurs in peripheral diseases such as allergic conjunctivitis, allergic rhinitis, hemorrhoids, atopic dermatitis, allergic dermatitis, acute and chronic urticaria (hives), psoriasis and dermatoses of fungal, allergic and non-allergic origin. Itching can also be a major symptom of many systemic diseases such as, Hodgkin's disease, chronic renal failure, polycythemia vera, hyperthyroidism, malignancy, infection, chronic cholestatic liver disease and end-stage renal disease, and cholestasis. In addition, senile itch without an obvious cause, except perhaps xerosis, occurs in more than half of the population aged 70 years. In all cases chronic severe generalized itch can be disabling.

While not intending to be complete, diseases or conditions associated with itch further include primary biliary cirrhosis (PBC), primary sclerosis cholangitis (PSC), chronic renal disease, epidural morphine, pregnancy, diabetes mellitus, thyroid illness, hyperparathyroidism, iron deficiency anemia, viral infection, aquagenic pruritus, and psychogenic itch. Itch causes sufferers to scratch, leading to skin damage, increased risk of skin infection, and worsening of inflammation. However, despite the prevalence of this clinically important symptom, the pathogenesis of itch is not well understood, and treatment options are limited (Paus, R., et al., J. Clin. Invest. 2006, 116:1174-1185).

Itching can be elicited by chemical, electrical, mechanical and thermal stimulation. So far no morphological structure has been identified as a specific receptor for the itch sensation, but it is assumed that itch receptors are linked to the free nerve endings of C-fibers close to the dermo-epidermal junction. The impulses set up in the thin, non-myelinated, slowly conducting C-fibers enter the spinal cord via the dorsal horn, then ascend in the contralateral spinothalmic tract, pass via the thalamus and end in the somatosensory cortex of the post-central gyrus. Itching and pain are related phenomena, and it was previously believed that itching was equal to sub-threshold pain, i.e. with increased activity in the C-fibers the perceived sensation changed from itching to pain. Although itch was once thought to be a subliminal form of pain (intensity theory), current evidence points to separate sensory neuronal systems mediating the two modalities. First, pain and itch are dissociable. Pain and itch evoke different motor responses, scratching for itch and withdrawal for pain. Second, based on clinical observations, systemically-administered opioids have a dichotomous effect on these two sensory modalities. μ-Opioid receptor agonists reduce pain but can cause itch. Furthermore, antagonizing the central μ-opioid receptors, for example with naloxone or naltrexone, suppresses pruritus and at the same time may lower the pain threshold.

Itch due to skin inflammation is thought to be mediated at least partly by activation of skin mast cells, which release pruritogenic mediators to activate receptors on peripheral nerve endings to transmit itch signals. Among the substances released from mast cells, histamine is a particularly potent pruritogen. When injected into the skin, histamine causes strong itch sensations in humans and animals. Therefore, antagonists of histamine receptors have been explored as itch treatments. There are several topical and systemic agents that suppress itching in selected clinical settings. Unfortunately, no universally effective anti-pruritic drug exists. Therefore, there is an urgent need for new approaches for managing itch.

Accordingly, one aspect of the present invention relates to the inhibition of the histamine 3 receptor (H3R) in an individual, such as by administration of a compound of the present invention, can reduce itching or pruritus. In Example 5 and Example 6 the G-protein coupled H3R is shown as a key effector of the itch sensation. Accordingly, in one embodiment, the present invention provides a method of preventing and/or treating itch in an individual in need thereof by administering a therapeutically effective amount of a compound or agent that modulates the H3R.

In addition, peripherally restricted inhibitors of H3R are capable of mediating the inhibition of itch. Accordingly, screening for peripherally restricted inhibitors (i.e. antagonists and/or inverse agonists), and the application of peripherally restricted inhibitors in the various embodiments of the invention is contemplated. Peripherally restricted compounds can be advantageous to the extent that the peripheral restriction reduces the CNS effects of H3R inhibition. Such effects may include, for example, wakefulness. In one embodiment of this invention, H3R inhibitors, for example antagonists and inverse agonists, are peripherally restricted and may be assayed or screened based on their inability or reduced ability to inhibit H3R in the CNS (for example, in the brain).

In one embodiment, the invention comprises a method for treating or preventing itching or the symptoms thereof in an individual wherein an inhibitor of H3R is administered to the individual.

In one embodiment, the invention disclosed herein is suitable for the prevention and/or treatment of itch that is associated with a disease or disorder selected from eczema, atopic eczematous dermatitis, seborrheic dermatitis, atopic dermatitis, contact dermatitis, irritant dermatitis, xerosis (dry skin), psoriasis, a fungal infection, athlete's foot, a yeast infection, diaper rash, vaginal itch, parasitic infections, parasitic infestations including scabies and lice, lichen planus, lichen simplex, lichen simplex chronicus, lichen sclerosis, itch secondary to medications, senile itch, uremia, idiopathic itch, itch associated with liver cirrhosis, itch associated with inflammation, itch associated with allergies, itch associated with cancer, itch associated with chemotherapy, itch associated with kidney disease, itch associated with haemodialysis, burns, scalds, sunburn, wound healing, itch associated with an insect bite, itch associated with a flea bite, itch associated with an insect sting, itch associated with a mosquito sting, itch associated with a mite bite, urticaria, urticaria caused by a plant, urticaria caused by poison ivy, urticaria caused by stinging nettle, sweat gland abnormalities, bullous pemphigoid, photodematoses, skin blisters, adult acne, chicken pox, and dermatitis herpetiformis.

Itching can be associated with various types of cancers such as Hodgkin's disease, Lymphoma, Leukemia, Kaposi's sarcoma, AIDs, liver metastases, and renal failure, and may be associated with some antibiotics. Acute itching, during the infusion of chemotherapy could be an early sign of a hypersensitivity reaction. Chemotherapy medications commonly associated with risk of allergic reactions include: L-asparaginase, paclitaxel, docetaxel, teniposide, procarbazine, and cytarabine. Itching can occur as chronic side effect of anticancer treatments including Proleukin® (Interleukin-2), Interferon (Intron® & Roferon®), radiation therapy, acute and chronic graft-versus-host disease (GVHD), and occasionally supportive growth factors including Neupogen® (G-CSF) and Leukine® (GM-CSF).

Certain Embodiments of the Present Invention

One aspect of the present invention pertains to methods of inducing wakefulness in an individual comprising administering to the individual in need thereof a therapeutically effective amount of a compound of the present invention or a pharmaceutical composition thereof.

One aspect of the present invention pertains to methods for treating an H3 receptor-associated disorder in an individual comprising administering to the individual in need thereof a therapeutically effective amount of a compound of the present invention or a pharmaceutical composition thereof.

One aspect of the present invention pertains to methods for treating an H3 receptor-associated disorder selected from the group: a cognitive disorder, epilepsy, brain trauma, depression, obesity, disorders of sleep and wakefulness, narcolepsy, shift-work sleep disorder, cataplexy, hypersomnia, somnolence syndrome, jet lag, sleep apnea, excessive daytime sleepiness, attention deficit hyperactivity disorder (ADHD), schizophrenia, allergies, allergic responses in the upper airway, allergic rhinitis, nasal congestion, dementia, Alzheimer's disease, pain, and pruritus in an individual comprising administering to the individual in need thereof a therapeutically effective amount of a compound of the present invention or a pharmaceutical composition thereof.

One aspect of the present invention pertains to methods for treating allergic rhinitis in an individual comprising administering to said individual in need thereof a therapeutically effective amount of a compound of the present invention or a pharmaceutical composition thereof.

One aspect of the present invention pertains to methods for treating pruritus in an individual comprising administering to the individual in need thereof a therapeutically effective amount of a compound of the present invention or a pharmaceutical composition thereof.

One aspect of the present invention pertains to methods for treating pruritus in an individual comprising administering to the individual in need thereof a therapeutically effective amount of a compound of the present invention or a pharmaceutical composition thereof, wherein pruritus is associated with a disorder selected from eczema, atopic eczematous dermatitis, seborrheic dermatitis, atopic dermatitis, contact dermatitis, irritant dermatitis, xerosis (dry skin), psoriasis, a fungal infection, athlete's foot, a yeast infection, diaper rash, vaginal itch, parasitic infections, parasitic infestations including scabies and lice, lichen planus, lichen simplex, lichen simplex chronicus, lichen sclerosis, itch secondary to medications, senile itch, uremia, idiopathic itch, itch associated with liver cirrhosis, itch associated with inflammation, itch associated with allergies, itch associated with cancer, itch associated with chemotherapy, itch associated with kidney disease, itch associated with haemodialysis, burns, scalds, sunburn, wound healing, itch associated with an insect bite, itch associated with a flea bite, itch associated with an insect sting, itch associated with a mosquito sting, itch associated with a mite bite, urticaria, urticaria caused by a plant, urticaria caused by poison ivy, urticaria caused by stinging nettle, sweat gland abnormalities, bullous pemphigoid, photodematoses, skin blisters, adult acne, chicken pox, and dermatitis herpetiformis.

One aspect of the present invention pertains to methods for treating a cognitive disorder in an individual comprising administering to the individual in need thereof a therapeutically effective amount of a compound of the present invention or a pharmaceutical composition thereof.

One aspect of the present invention pertains to methods for treating epilepsy in an individual comprising administering to the individual in need thereof a therapeutically effective amount of a compound of the present invention or a pharmaceutical composition thereof.

One aspect of the present invention pertains to methods for treating a disorder of sleep and wakefulness in an individual comprising administering to the individual in need thereof a therapeutically effective amount of a compound of the present invention or a pharmaceutical composition thereof.

One aspect of the present invention pertains to methods for treating narcolepsy in an individual comprising administering to the individual in need thereof a therapeutically effective amount of a compound of the present invention or a pharmaceutical composition thereof.

One aspect of the present invention pertains to methods for treating shift-work sleep disorder in an individual comprising administering to the individual in need thereof a therapeutically effective amount of a compound of the present invention or a pharmaceutical composition thereof.

One aspect of the present invention pertains to methods for treating cataplexy in an individual comprising administering to the individual in need thereof a therapeutically effective amount of a compound of the present invention or a pharmaceutical composition thereof.

One aspect of the present invention pertains to methods for treating jet lag in an individual comprising administering to the individual in need thereof a therapeutically effective amount of a compound of the present invention or a pharmaceutical composition thereof.

One aspect of the present invention pertains to methods for treating sleep apnea in an individual comprising administering to the individual in need thereof a therapeutically effective amount of a compound of the present invention or a pharmaceutical composition thereof.

One aspect of the present invention pertains to methods for treating excessive daytime sleepiness in an individual comprising administering to the individual in need thereof a therapeutically effective amount of a compound of the present invention or a pharmaceutical composition thereof.

One aspect of the present invention pertains to methods for treating attention deficit hyperactivity disorder in an individual comprising administering to the individual in need thereof a therapeutically effective amount of a compound of the present invention or a pharmaceutical composition thereof.

One aspect of the present invention pertains to methods for treating schizophrenia in an individual comprising administering to the individual in need thereof a therapeutically effective amount of a compound of the present invention or a pharmaceutical composition thereof.

One aspect of the present invention pertains to methods for treating pain in an individual comprising administering to the individual in need thereof a therapeutically effective amount of a compound of the present invention or a pharmaceutical composition thereof.

One aspect of the present invention pertains to the use of a compound of the present invention or a pharmaceutical composition thereof in the manufacture of a medicament for inducing wakefulness.

One aspect of the present invention pertains to the use of a compound of the present invention or a pharmaceutical composition thereof in the manufacture of a medicament for the treatment of an H3 receptor-associated disorder.

One aspect of the present invention pertains to the use of a compound of the present invention or a pharmaceutical composition thereof in the manufacture of a medicament for the treatment of a disorder selected from the group: a cognitive disorder, epilepsy, brain trauma, depression, obesity, disorders of sleep and wakefulness, narcolepsy, shift-work sleep disorder, cataplexy, hypersomnia, somnolence syndrome, jet lag, sleep apnea, excessive daytime sleepiness, attention deficit hyperactivity disorder (ADHD), schizophrenia, allergies, allergic responses in the upper airway, allergic rhinitis, nasal congestion, dementia, Alzheimer's disease, pain, and pruritus.

One aspect of the present invention pertains to the use of a compound of the present invention or a pharmaceutical composition thereof in the manufacture of a medicament for the treatment of allergic rhinitis.

One aspect of the present invention pertains to the use of a compound of the present invention or a pharmaceutical composition thereof in the manufacture of a medicament for the treatment of pruritus.

One aspect of the present invention pertains to the use of a compound of the present invention or a pharmaceutical composition thereof in the manufacture of a medicament for the treatment of pruritus, wherein pruritus is associated with a disorder selected from eczema, atopic eczematous dermatitis, seborrheic dermatitis, atopic dermatitis, contact dermatitis, irritant dermatitis, xerosis (dry skin), psoriasis, a fungal infection, athlete's foot, a yeast infection, diaper rash, vaginal itch, parasitic infections, parasitic infestations including scabies and lice, lichen planus, lichen simplex, lichen simplex chronicus, lichen sclerosis, itch secondary to medications, senile itch, uremia, idiopathic itch, itch associated with liver cirrhosis, itch associated with inflammation, itch associated with allergies, itch associated with cancer, itch associated with chemotherapy, itch associated with kidney disease, itch associated with haemodialysis, burns, scalds, sunburn, wound healing, itch associated with an insect bite, itch associated with a flea bite, itch associated with an insect sting, itch associated with a mosquito sting, itch associated with a mite bite, urticaria, urticaria caused by a plant, urticaria caused by poison ivy, urticaria caused by stinging nettle, sweat gland abnormalities, bullous pemphigoid, photodematoses, skin blisters, adult acne, chicken pox, and dermatitis herpetiformis.

One aspect of the present invention pertains to the use of a compound of the present invention or a pharmaceutical composition thereof in the manufacture of a medicament for the treatment of a cognitive disorder.

One aspect of the present invention pertains to the use of a compound of the present invention or a pharmaceutical composition thereof in the manufacture of a medicament for the treatment of epilepsy.

One aspect of the present invention pertains to the use of a compound of the present invention or a pharmaceutical composition thereof in the manufacture of a medicament for the treatment of a disorder of sleep and wakefulness.

One aspect of the present invention pertains to the use of a compound of the present invention or a pharmaceutical composition thereof in the manufacture of a medicament for the treatment of narcolepsy.

One aspect of the present invention pertains to the use of a compound of the present invention or a pharmaceutical composition thereof in the manufacture of a medicament for the treatment of shift-work sleep disorder.

One aspect of the present invention pertains to the use of a compound of the present invention or a pharmaceutical composition thereof in the manufacture of a medicament for the treatment of cataplexy.

One aspect of the present invention pertains to the use of a compound of the present invention or a pharmaceutical composition thereof in the manufacture of a medicament for the treatment of jet lag.

One aspect of the present invention pertains to the use of a compound of the present invention or a pharmaceutical composition thereof in the manufacture of a medicament for the treatment of sleep apnea.

One aspect of the present invention pertains to the use of a compound of the present invention or a pharmaceutical composition thereof in the manufacture of a medicament for the treatment of excessive daytime sleepiness.

One aspect of the present invention pertains to the use of a compound of the present invention or a pharmaceutical composition thereof in the manufacture of a medicament for the treatment of attention deficit hyperactivity disorder.

One aspect of the present invention pertains to the use of a compound of the present invention or a pharmaceutical composition thereof in the manufacture of a medicament for the treatment of schizophrenia.

One aspect of the present invention pertains to the use of a compound of the present invention or a pharmaceutical composition thereof in the manufacture of a medicament for the treatment of pain.

One aspect of the present invention pertains to a compound of the present invention or a pharmaceutical composition thereof for use in a method of treatment of the human or animal body by therapy.

One aspect of the present invention pertains to a compound of the present invention or a pharmaceutical composition thereof for use in a method of inducing wakefulness.

One aspect of the present invention pertains to a compound of the present invention or a pharmaceutical composition thereof for use in a method of treatment of an H3 receptor-associated disorder.

One aspect of the present invention pertains to a compound of the present invention or a pharmaceutical composition thereof for use in a method of treatment of an H3 receptor-associated disorder selected from the group: a cognitive disorder, epilepsy, brain trauma, depression, obesity, disorders of sleep and wakefulness, narcolepsy, shift-work sleep disorder, cataplexy, hypersomnia, somnolence syndrome, jet lag, sleep apnea, excessive daytime sleepiness, attention deficit hyperactivity disorder (ADHD), schizophrenia, allergies, allergic responses in the upper airway, allergic rhinitis, nasal congestion, dementia, Alzheimer's disease, pain, and pruritus.

One aspect of the present invention pertains to a compound of the present invention or a pharmaceutical composition thereof for use in a method of treatment of allergic rhinitis.

One aspect of the present invention pertains to a compound of the present invention or a pharmaceutical composition thereof for use in a method of treatment of pruritus.

One aspect of the present invention pertains to a compound of the present invention or a pharmaceutical composition thereof for use in a method of treatment of pruritus, wherein the pruritus is associated with a disorder selected from eczema, atopic eczematous dermatitis, seborrheic dermatitis, atopic dermatitis, contact dermatitis, irritant dermatitis, xerosis (dry skin), psoriasis, a fungal infection, athlete's foot, a yeast infection, diaper rash, vaginal itch, parasitic infections, parasitic infestations including scabies and lice, lichen planus, lichen simplex, lichen simplex chronicus, lichen sclerosis, itch secondary to medications, senile itch, uremia, idiopathic itch, itch associated with liver cirrhosis, itch associated with inflammation, itch associated with allergies, itch associated with cancer, itch associated with chemotherapy, itch associated with kidney disease, itch associated with haemodialysis, burns, scalds, sunburn, wound healing, itch associated with an insect bite, itch associated with a flea bite, itch associated with an insect sting, itch associated with a mosquito sting, itch associated with a mite bite, urticaria, urticaria caused by a plant, urticaria caused by poison ivy, urticaria caused by stinging nettle, sweat gland abnormalities, bullous pemphigoid, photodematoses, skin blisters, adult acne, chicken pox, and dermatitis herpetiformis.

One aspect of the present invention pertains to a compound of the present invention or a pharmaceutical composition thereof for use in a method of treatment of a cognitive disorder.

One aspect of the present invention pertains to a compound of the present invention or a pharmaceutical composition thereof for use in a method of treatment of epilepsy.

One aspect of the present invention pertains to a compound of the present invention or a pharmaceutical composition thereof for use in a method of treatment of a disorder of sleep and wakefulness.

One aspect of the present invention pertains to a compound of the present invention or a pharmaceutical composition thereof for use in a method of treatment of narcolepsy.

One aspect of the present invention pertains to a compound of the present invention or a pharmaceutical composition thereof for use in a method of treatment of shift-work sleep disorder.

One aspect of the present invention pertains to a compound of the present invention or a pharmaceutical composition thereof for use in a method of treatment of cataplexy.

One aspect of the present invention pertains to a compound of the present invention or a pharmaceutical composition thereof for use in a method of treatment of jet lag.

One aspect of the present invention pertains to a compound of the present invention or a pharmaceutical composition thereof for use in a method of treatment of sleep apnea.

One aspect of the present invention pertains to a compound of the present invention or a pharmaceutical composition thereof for use in a method of treatment of excessive daytime sleepiness.

One aspect of the present invention pertains to a compound of the present invention or a pharmaceutical composition thereof for use in a method of treatment of attention deficit hyperactivity disorder.

One aspect of the present invention pertains to a compound of the present invention or a pharmaceutical composition thereof for use in a method of treatment of schizophrenia.

One aspect of the present invention pertains to a compound of the present invention or a pharmaceutical composition thereof for use in a method of treatment of pain.

Pharmaceutical Compositions

A further aspect of the present invention pertains to pharmaceutical compositions comprising one or more compounds as described herein and one or more pharmaceutically acceptable carriers. Some embodiments pertain to pharmaceutical compositions comprising a compound of the present invention and a pharmaceutically acceptable carrier.

Some embodiments of the present invention include a method of producing a pharmaceutical composition comprising admixing at least one compound according to any of the compound embodiments disclosed herein and a pharmaceutically acceptable carrier.

Formulations may be prepared by any suitable method, typically by uniformly mixing the active compound(s) with liquids or finely divided solid carriers, or both, in the required proportions and then, if necessary, forming the resulting mixture into a desired shape.

Conventional excipients, such as binding agents, fillers, acceptable wetting agents, tabletting lubricants and disintegrants may be used in tablets and capsules for oral administration. Liquid preparations for oral administration may be in the form of solutions, emulsions, aqueous or oily suspensions and syrups. Alternatively, the oral preparations may be in the form of dry powder that can be reconstituted with water or another suitable liquid vehicle before use. Additional additives such as suspending or emulsifying agents, non-aqueous vehicles (including edible oils), preservatives and flavorings and colorants may be added to the liquid preparations. Parenteral dosage forms may be prepared by dissolving the compound of the invention in a suitable liquid vehicle and filter sterilizing the solution before filling and sealing an appropriate vial or ampule. These are just a few examples of the many appropriate methods well known in the art for preparing dosage forms.

A compound of the present invention can be formulated into pharmaceutical compositions using techniques well known to those in the art. Suitable pharmaceutically-acceptable carriers, outside those mentioned herein, are known in the art; for example, see Remington, *The Science and Practice of Pharmacy*, 20$^{th}$ Edition, 2000, Lippincott Williams & Wilkins, (Editors: Gennaro et al.).

While it is possible that, for use in the prophylaxis or treatment, a compound of the invention may, in an alternative use, be administered as a raw or pure chemical, it is preferable however to present the compound or active ingredient as a pharmaceutical formulation or composition further comprising a pharmaceutically acceptable carrier.

The invention thus further provides pharmaceutical formulations comprising a compound of the invention or a pharmaceutically acceptable salt, solvate, hydrate or derivative thereof together with one or more pharmaceutically acceptable carriers thereof and/or prophylactic ingredients. The carrier(s) must be "acceptable" in the sense of being compatible with the other ingredients of the formulation and not overly deleterious to the recipient thereof.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation, insufflation or by a transdermal patch. Transdermal patches dispense a drug at a controlled rate by presenting the drug for absorption in an efficient manner with a minimum of degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The compounds of the invention, together with a conventional adjuvant, carrier, or diluent, may thus be placed into the form of pharmaceutical formulations and unit dosages thereof and in such form may be employed as solids, such as tablets or filled capsules, or liquids such as solutions, suspensions, emulsions, elixirs, gels or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles and such unit dosage forms may contain any suitable effective amount of the active ingredient commensurate with the intended daily dosage range to be employed.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable pharmaceutically acceptable carrier.

Compounds of the present invention or a solvate or physiologically functional derivative thereof can be used as active ingredients in pharmaceutical compositions, specifically as H3 receptor modulators. By the term "active ingredient" is defined in the context of a "pharmaceutical composition" and refers to a component of a pharmaceutical composition that provides the primary pharmacological effect, as opposed to an "inactive ingredient" which would generally be recognized as providing no pharmaceutical benefit.

The dose when using the compounds of the present invention can vary within wide limits and as is customary and is known to the physician, it is to be tailored to the individual conditions in each individual case. It depends, for example, on the nature and severity of the illness to be treated, on the condition of the patient, on the compound employed or on whether an acute or chronic disease state is treated or prophylaxis is conducted or on whether further active compounds are administered in addition to the compounds of the present invention. Representative doses of the present invention include, but not limited to, about 0.001 mg to about 5000 mg, about 0.001 mg to about 2500 mg, about 0.001 mg to about 1000 mg, 0.001 mg to about 500 mg, 0.001 mg to about 250 mg, about 0.001 mg to 100 mg, about 0.001 mg to about 50 mg and about 0.001 mg to about 25 mg. Multiple doses may be administered during the day, especially when relatively large amounts are deemed to be needed, for example 2, 3 or 4 doses. Depending on the individual and as deemed appropriate from the patient's physician or caregiver it may be necessary to deviate upward or downward from the doses described herein.

The amount of active ingredient, or an active salt or derivative thereof, required for use in treatment will vary not only with the particular salt selected but also with the route of administration, the nature of the condition being treated and the age and condition of the patient and will ultimately be at the discretion of the attendant physician or clinician. In general, one skilled in the art understands how to extrapolate in vivo data obtained in a model system, typically an animal model, to another, such as a human. In some circumstances, these extrapolations may merely be based on the weight of the animal model in comparison to another, such as a mammal, preferably a human, however, more often, these extrapolations are not simply based on weights, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, on whether an acute or chronic disease state is being treated or prophylaxis is conducted or on whether further active compounds are administered in addition to the compounds of the present invention and as part of a drug combination. The dosage regimen for treating a disease condition with the compounds and/or compositions of this invention is selected in accordance with a variety factors as cited above. Thus, the actual dosage regimen employed may vary widely and therefore may deviate from a preferred dosage regimen and one skilled in the art will recognize that dosage and dosage regimen outside these typical ranges can be tested and, where appropriate, may be used in the methods of this invention.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations. The daily dose can be divided, especially when relatively large amounts are administered as deemed appropriate, into several, for example 2, 3 or 4 part administrations. If appropriate, depending on individual behavior, it may be necessary to deviate upward or downward from the daily dose indicated.

The compounds of the present invention can be administrated in a wide variety of oral and parenteral dosage forms. It will be obvious to those skilled in the art that the following dosage forms may comprise, as the active component, either a compound of the invention or a pharmaceutically acceptable salt, solvate or hydrate of a compound of the invention.

For preparing pharmaceutical compositions from the compounds of the present invention, the selection of a suitable pharmaceutically acceptable carrier can be either solid, liquid or a mixture of both. Solid form preparations include powders, tablets, pills, capsules, cachets, suppositories and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted to the desire shape and size.

The powders and tablets may contain varying percentage amounts of the active compound. A representative amount in a powder or tablet may contain from 0.5 to about 90 percent of the active compound; however, an artisan would know when amounts outside of this range are necessary. Suitable carriers for powders and tablets are magnesium carbonate, magnesium stearate, talc, sugar, lactose, pectin, dextrin, starch, gelatin, tragacanth, methylcellulose, sodium carboxymethylcellulose, a low melting wax, cocoa butter and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized molds, allowed to cool and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The pharmaceutical compositions may take such forms as suspensions, solutions, or emulsions in oily or aqueous vehicles and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous formulations suitable for oral use can be prepared by dissolving or suspending the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well-known suspending agents.

Also included are solid form preparations which are intended to be converted, shortly before use, to liquid form preparations for oral administration. Such liquid forms include solutions, suspensions and emulsions. These preparations may contain, in addition to the active component, colorants, flavors, stabilizers, buffers, artificial and natural sweeteners, dispersants, thickeners, solubilizing agents and the like.

For topical administration to the epidermis the compounds according to the invention may be formulated as ointments, creams or lotions, or as a transdermal patch.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multi-dose form. In the latter case of a dropper or pipette, this may be achieved by the patient administering an appropriate, predetermined volume of the solution or suspension. In the case of a spray, this may be achieved for example by means of a metering atomizing spray pump.

Administration to the respiratory tract may also be achieved by means of an aerosol formulation in which the active ingredient is provided in a pressurized pack with a suitable propellant. If the compounds of the present invention or pharmaceutical compositions comprising them are administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of the compounds of the present invention as an aerosol can be prepared by processes well known to the person skilled in the art. For their preparation, for example, solutions or dispersions of the compounds of the present invention in water, water/alcohol mixtures or suitable saline solutions can be employed using customary additives, for example benzyl alcohol or other suitable preservatives, absorption enhancers for increasing the bioavailability, solubilizers, dispersants and others and, if appropriate, customary propellants, for example include carbon dioxide, CFCs, such as, dichlorodifluoromethane, trichlorofluoromethane, or dichlorotetrafluoroethane; and the like. The aerosol may conveniently also contain a surfactant such as lecithin. The dose of drug may be controlled by provision of a metered valve.

In formulations intended for administration to the respiratory tract, including intranasal formulations, the compound will generally have a small particle size for example of the order of 10 microns or less. Such a particle size may be obtained by means known in the art, for example by micronization. When desired, formulations adapted to give sustained release of the active ingredient may be employed.

Alternatively the active ingredients may be provided in the form of a dry powder, for example, a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

The compounds according to the invention may optionally exist as pharmaceutically acceptable salts including pharmaceutically acceptable acid addition salts prepared from pharmaceutically acceptable non-toxic acids including inorganic and organic acids. Representative acids include, but are not limited to, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like, such as those pharmaceutically acceptable salts listed in *Journal of Pharmaceutical Sciences*, 66:1-19 (1977).

The acid addition salts may be obtained as the direct products of compound synthesis. In the alternative, the free base may be dissolved in a suitable solvent containing the appropriate acid and the salt isolated by evaporating the solvent or otherwise separating the salt and solvent. The compounds of this invention may form solvates with standard low molecular weight solvents using methods known to the skilled artisan.

Compounds of the present invention can be converted to "pro-drugs." The term "pro-drugs" refers to compounds that have been modified with specific chemical groups known in the art and when administered into an individual these groups undergo biotransformation to give the parent compound. Pro-drugs can thus be viewed as compounds of the invention containing one or more specialized non-toxic protective groups used in a transient manner to alter or to eliminate a property of the compound. In one general aspect, the "pro-drug" approach is utilized to facilitate oral absorption. A thorough discussion is provided in T. Higuchi and V. Stella, Pro-drugs as Novel Delivery Systems Vol. 14 of the A.C.S. Symposium Series; and in *Bioreversible Carriers in Drug Design*, ed. Edward B. Roche, American Pharmaceutical Association and Pergamon Press, 1987.

Some embodiments of the present invention include a method of producing a pharmaceutical composition for "combination-therapy" comprising admixing at least one compound according to any of the compound embodiments disclosed herein, together with at least one known pharmaceutical agent as described herein and a pharmaceutically acceptable carrier.

It is noted that when the H3 receptor modulators are utilized as active ingredients in a pharmaceutical composition, these are not intended for use only in humans, but in other non-human mammals as well. Indeed, recent advances in the area of animal health-care mandate that consideration be given for the use of active agents, such as H3 receptor modulators, for the treatment of an H3-associated disease or disorder in companionship animals (e.g., cats, dogs, etc.) and in livestock animals (e.g., cows, chickens, fish, etc.) Those of ordinary skill in the art are readily credited with understanding the utility of such compounds in such settings.

Hydrates and Solvates

It is understood that when the phrase "pharmaceutically acceptable salts, solvates, and hydrates" or the phrase "pharmaceutically acceptable salt, solvate, or hydrate" is used when referring to compounds described herein, it embraces pharmaceutically acceptable solvates and/or hydrates of the compounds, pharmaceutically acceptable salts of the compounds, as well as pharmaceutically acceptable solvates and/or hydrates of pharmaceutically acceptable salts of the compounds. It is also understood that when the phrase "pharmaceutically acceptable solvates and hydrates" or the phrase "pharmaceutically acceptable solvate or hydrate" is used when referring to compounds described herein that are salts, it embraces pharmaceutically acceptable solvates and/or hydrates of such salts.

It will be apparent to those skilled in the art that the dosage forms described herein may comprise, as the active component, either a compound described herein or a pharmaceutically acceptable salt or as a solvate or hydrate thereof. Moreover, various hydrates and solvates of the compounds described herein and their salts will find use as intermediates in the manufacture of pharmaceutical compositions. Typical procedures for making and identifying suitable hydrates and solvates, outside those mentioned herein, are well known to those in the art; see for example, pages 202-209 of K. J. Guillory, "Generation of Polymorphs, Hydrates, Solvates, and Amorphous Solids," in: Polymorphism in Pharmaceutical Solids, ed. Harry G. Britain, Vol. 95, Marcel Dekker, Inc., New York, 1999. Accordingly, one aspect of the present invention pertains to methods of administering hydrates and solvates of compounds described herein and/or their pharmaceutical acceptable salts, that can be isolated and characterized by methods known in the art, such as, thermogravimetric analysis (TGA), TGA-mass spectroscopy, TGA-Infrared spectroscopy, powder X-ray diffraction (XRPD), Karl Fisher titration, high resolution X-ray diffraction, and the like. There are several commercial entities that provide quick and efficient services for identifying solvates and hydrates on a routine basis. Example companies offering these services include Wilmington PharmaTech (Wilmington, Del.), Avantium Technologies (Amsterdam) and Aptuit (Greenwich, Conn.).

Isotopes

The present disclosure includes all isotopes of atoms occurring in the present compounds, intermediates, salts and crystalline forms thereof. Isotopes include those atoms having the same atomic number but different mass numbers. One aspect of the present invention includes every combination of one or more atoms in the present compounds, intermediates, salts, and crystalline forms thereof that is replaced with an atom having the same atomic number but a different mass number. One such example is the replacement of an atom that is the most naturally abundant isotope, such as $^1H$ or $^{12}C$, found in one the present compounds, intermediates, salts, and crystalline forms thereof, with a different atom that is not the most naturally abundant isotope, such as $^2H$ or $^3H$ (replacing $^1H$), or $^{11}C$, $^{13}C$, or $^{14}C$ (replacing $^{12}C$). A compound wherein such a replacement has taken place is commonly referred to as being an isotopically-labeled compound. Isotopic-labeling of the present compounds, intermediates, salts, and crystalline forms thereof can be accomplished using any one of a variety of different synthetic methods know to those of ordinary skill in the art and they are readily credited with understanding the synthetic methods and available reagents needed to conduct such isotopic-labeling. By way of general example, and without limitation, isotopes of hydrogen include $^2H$ (deuterium) and $^3H$ (tritium). Isotopes of carbon include $^{11}C$, $^{13}C$, and $^{14}C$. Isotopes of nitrogen include $^{13}N$ and $^{15}N$. Isotopes of oxygen include $^{15}O$, $^{17}O$, and $^{18}C$. An isotope of fluorine includes $^{18}F$. An isotope of sulfur includes $^{35}S$. An isotope of chlorine includes $^{36}Cl$. Isotopes of bromine include $^{75}Br$, $^{76}Br$, $^{77}Br$, and $^{82}Br$. Isotopes of iodine include $^{123}I$, $^{124}I$, $^{125}I$, and $^{131}I$. Another aspect of the present invention includes compositions, such as, those prepared during synthesis, preformulation, and the like, and pharmaceutical compositions, such as, those prepared with the intent of using in a mammal for the treatment of one or more of the disorders described herein, comprising one or more of the present compounds, intermediates, salts, and crystalline forms thereof, wherein the naturally occurring distribution of the isotopes in the composition is perturbed. Another aspect of the present invention includes compositions and pharmaceutical compositions comprising compounds as described herein wherein the compound is enriched at one or more positions with an isotope other than the most naturally abundant isotope. Methods are readily available to measure such isotope perturbations or enrichments, such as, mass spectrometry, and for isotopes that are radio-isotopes additional methods are available, such as, radio-detectors used in connection with HPLC or GC.

Other Utilities

Another object of the present invention relates to radiolabeled compounds of the present invention that would be useful not only in radio-imaging but also in assays, both in vitro and in vivo, for localizing and quantitating the H3 receptor in tissue samples, including human and for identifying H3 receptor ligands by inhibition binding of a radio-labeled compound. It is a further object of this invention to develop novel H3 receptor assays of which comprise such radio-labeled compounds.

The present invention embraces isotopically-labeled compounds of the present invention. Isotopically or radio-labeled compounds are those which are identical to compounds disclosed herein, but for the fact that one or more atoms are replaced or substituted by an atom having an atomic mass or mass number different from the atomic mass or mass number most commonly found in nature. Suitable radionuclides that may be incorporated in compounds of the present invention include but are not limited to $^2H$ (also written as D for deuterium), $^3H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{75}Br$, $^{76}Br$, $^{77}Br$, $^{82}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro H3 receptor labeling and competition assays, compounds that incorporate $^3H$, $^{14}C$, $^{82}Br$, $^{125}I$, $^{131}I$ or $^{35}S$ will generally be most useful. For radio-imaging applications $^{11}C$, $^{18}F$, $^{125}I$, $^{124}$, $^{131}I$, $^{75}Br$, $^{76}Br$ or $^{77}Br$ will generally be most useful.

It is understood that a "radio-labeled" or "labeled compound" is a compound of Formulae (Ia), (Ic), (Ie), (Ig), (Ii), (Ik), and (Im) that has incorporated at least one radionuclide; in some embodiments the radionuclide is selected from the group consisting of $^3H$, $^{14}C$, $^{125}I$, $^{35}S$ and $^{82}Br$.

Certain isotopically-labeled compounds of the present invention are useful in compound and/or substrate tissue distribution assays. In some embodiments the radionuclide $^3H$ and/or $^{14}C$ isotopes are useful in these studies. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of the present invention can generally be prepared by following procedures analogous to those disclosed in the Drawings and Examples infra, by substituting an isotopically labeled reagent for a non-isotopically labeled reagent. Other synthetic methods that are useful are discussed infra. Moreover, it should be understood that all of the atoms represented in the compounds of the invention can be either the most commonly occurring isotope of such atoms or the scarcer radio-isotope or nonradioactive isotope.

Synthetic methods for incorporating radio-isotopes into organic compounds are applicable to compounds of the invention and are well known in the art. These synthetic methods, for example, incorporating activity levels of tritium into target molecules, are as follows:

A. Catalytic Reduction with Tritium Gas: This procedure normally yields high specific activity products and requires halogenated or unsaturated precursors.

B. Reduction with Sodium Borohydride [$^3H$]: This procedure is rather inexpensive and requires precursors containing reducible functional groups such as aldehydes, ketones, lactones, esters and the like.

C. Reduction with Lithium Aluminum Hydride [$^3H$]: This procedure offers products at almost theoretical specific activities. It also requires precursors containing reducible functional groups such as aldehydes, ketones, lactones, esters and the like.

D. Tritium Gas Exposure Labeling: This procedure involves exposing precursors containing exchangeable protons to tritium gas in the presence of a suitable catalyst.

E. N-Methylation using Methyl Iodide [$^3H$]: This procedure is usually employed to prepare O-methyl or N-methyl ($^3H$) products by treating appropriate precursors with high specific activity methyl iodide ($^3$H). This method in general allows for higher specific activity, such as for example, about 70-90 Ci/mmol.

Synthetic methods for incorporating activity levels of $^{125}$I into target molecules include:

A. Sandmeyer and like reactions: This procedure transforms an aryl amine or a heteroaryl amine into a diazonium salt, such as a diazonium tetrafluoroborate salt and subsequently to $^{125}$I labeled compound using Na$^{125}$I. A represented procedure was reported by Zhu, G-D. and co-workers in *J. Org. Chem.*, 2002, 67, 943-948.

B. Ortho $^{125}$Iodination of phenols: This procedure allows for the incorporation of $^{125}$I at the ortho position of a phenol as reported by Collier, T. L. and co-workers in *J. Labelled Compd. Radiopharm.*, 1999, 42, S264-S266.

C. Aryl and heteroaryl bromide exchange with $^{125}$I: This method is generally a two step process. The first step is the conversion of the aryl or heteroaryl bromide to the corresponding tri-alkyltin intermediate using for example, a Pd catalyzed reaction [i.e. Pd(Ph$_3$P)$_4$] or through an aryl or heteroaryl lithium, in the presence of a tri-alkyltinhalide or hexaalkylditin [e.g., (CH$_3$)$_3$SnSn(CH$_3$)$_3$]. A representative procedure was reported by Le Bas, M.-D. and co-workers in *J. Labelled Compd. Radiopharm*, 2001, 44, S280-S282.

A radiolabeled H3 receptor compound of Formula (Ia) can be used in a screening assay to identify/evaluate compounds. In general terms, a newly synthesized or identified compound (i.e., test compound) can be evaluated for its ability to reduce binding of the "radio-labeled compound of Formula (Ia)" to the H3 receptor. Accordingly, the ability of a test compound to compete with the "radio-labeled compound of Formula (Ia)" for the binding to the H3 receptor directly correlates to its binding affinity.

The labeled compounds of the present invention bind to the H3 receptor. In one embodiment the labeled compound has an IC$_{50}$ less than about 500 µM, in another embodiment the labeled compound has an IC$_{50}$ less than about 100 µM, in yet another embodiment the labeled compound has an IC$_{50}$ less than about 10 µM, in yet another embodiment the labeled compound has an IC$_{50}$ less than about 1 µM and in still yet another embodiment the labeled inhibitor has an IC$_{50}$ less than about 0.1 µM.

Other uses of the disclosed receptors and methods will become apparent to those in the art based upon, inter alia, a review of this disclosure.

As will be recognized, the steps of the methods of the present invention need not be performed any particular number of times or in any particular sequence. Additional objects, advantages and novel features of this invention will become apparent to those skilled in the art upon examination of the following examples thereof, which are intended to be illustrative and not intended to be limiting.

EXAMPLES

Example 1

Syntheses of Compounds of the Present Invention

General synthetic schemes for the preparation of compounds of the present invention are illustrated in FIGS. 1 through 4 where the symbols have the same definitions as used throughout this disclosure.

The compounds of the invention and their syntheses are further illustrated by the following examples. The following examples are provided to further define the invention without, however, limiting the invention to the particulars of these examples. The compounds described herein, supra and infra, are named according to the CS ChemDraw Ultra Version 7.0.1, AutoNom version 2.2, CS ChemDraw Ultra Version 9.0.7, or ChemBioDraw Ultra Version 12.0. In certain instances common names are used and it is understood that these common names would be recognized by those skilled in the art.

Chemistry:

Proton nuclear magnetic resonance ($^1$H NMR) spectra were recorded on a Bruker Avance-400 equipped with a QNP (Quad Nucleus Probe) or a BBI (Broad Band Inverse) and z-gradient. Chemical shifts are given in parts per million (ppm) with the residual solvent signal used as reference. NMR abbreviations are used as follows: s=singlet, d=doublet, dd=doublet of doublets, ddd=doublet of doublet of doublets, dt=doublet of triplets, t=triplet, td=triplet of doublets, tt=triplet of triplets, q=quartet, m=multiplet, bs=broad singlet, bt=broad triplet. Microwave irradiations were carried out using a Smith Synthesizer™ or an Emrys Optimizer™ (Biotage). Thin-layer chromatography (TLC) was performed on silica gel 60 F$_{254}$ (Merck), preparatory thin-layer chromatography (prep TLC) was preformed on PK6F silica gel 60 A 1 mm plates (Whatman) and column chromatography was carried out on a silica gel column using Kieselgel 60, 0.063-0.200 mm (Merck). Evaporation was done under reduced pressure on a Büchi rotary evaporator.

LCMS spec: HPLC-pumps: LC-10AD VP, Shimadzu Inc.; HPLC system controller: SCL-10A VP, Shimadzu Inc; UV-Detector: SPD-10A VP, Shimadzu Inc; Autosampler: CTC HTS, PAL, Leap Scientific; Mass spectrometer: API 150EX with Turbo Ion Spray source, AB/MDS Sciex; Software: Analyst 1.2.

Example 1.1

Preparation of (R)-4-(2-(2-Methylpyrrolidin-1-yl)ethyl)phenylboronic Acid

Step A: Preparation of (R)-1-(4-Bromophenethyl)-2-methylpyrrolidine

A 4 L jacketed reactor equipped with mechanical stirrer, thermocouple, gas inlet, heating/cooling and condenser was charged with 4-bromophenethyl methanesulfonate (199.8 g, 716 mmol), followed by acetonitrile (2.2 L), and the resulting slurry was stirred efficiently. Water (270 mL) was then added, followed by gradual addition of potassium carbonate (297.2 g, 2.147 mol). (R)-2-methylpyrrolidine L-tartrate (168.8 g, 717 mmol) was then added, and the reaction mixture was heated at 71° C. overnight. The reaction mixture was cooled and the solvent was removed. The residue was suspended in water (500 mL) and extracted with isopropyl acetate (2×400 mL). The organic extracts were combined, rinsed with water (150 mL), dried over sodium sulfate, filtered, and concentrated to dryness to provide a golden yellow oil (191 g). This material was combined with 185 g of material which was prepared at identical scale by the same method and dissolved in isopropyl acetate (2×500 mL). The mixture was extracted with 1N HCl (2×300 mL and 1×200 mL). The acidic aqueous layer was separated and pH adjusted to 11-12 with 25% NaOH. The resulting mixture was then extracted with isopropyl acetate (2×350 mL), washed with water (150 mL) and dried over MgSO$_4$ (100 g). Upon filtration and solvent removal, a pale yellow oil was obtained to provide the title compound (337.5 g). LCMS m/z=268.1 [M+H]$^+$; $^1$H NMR (CDCl$_3$, 400 MHz) δ ppm 1.16 (d, J=6.2 Hz, 3H), 1.46-1.55 (m, 1H), 1.71-1.81 (m, 1H), 1.82-1.90 (m, 1H), 1.94-2.01 (m, 1H), 2.24-2.31 (m, 1H), 2.32-2.39 (m, 1H), 2.41-2.47 (m, 1H), 2.84 (t, J=8.2 Hz, 2H), 3.01-3.08 (m, 1H), 3.26-3.31 (m, 1H), 7.11 (d, J=8.5 Hz, 2H), 7.42 (d, J=8.1 Hz, 2H).

Step B: Preparation of (R)-4-(2-(2-Methylpyrrolidin-1-yl)ethyl)phenylboronic Acid To a 1 L 3-neck flask equipped with mechanical stirrer, thermometer, and addition funnel under an atmosphere of nitrogen was charged a solution of (R)-1-(4-bromophenethyl)-2-methylpyrrolidine (26.8 g, 100 mmol) in anhydrous THF (250 mL). The reaction mixture was then cooled to an internal temperature of −78° C. A solution of n-butyl lithium (2.5M in hexane, 52 mL, 130 mmol) was added dropwise, maintaining an internal temperature below −70° C. Once addition was complete, stirring was continued an additional 15 min prior to the addition of triisopropyl borate (75 g, 400 mmol), followed by a rinse with 50 mL anhydrous THF, maintaining an internal temperature below −65° C. during addition. The reaction mixture was then allowed to warm to ambient temperature over 1.5 h, and was then quenched by dropwise addition of 2 N HCl (100 mL). The resulting mixture was stirred overnight, and the solvent volume was reduced to about 150 mL. The resulting suspension was cooled in an ice bath and filtered, rinsing sparingly with cold isopropanol. The filtrate volume was again reduced to 50 mL and the process was repeated. The filter cakes were combined, taken up in boiling isopropanol (250 mL), dissolving most, but not all of the solids. The mixture was then cooled in an ice bath and filtered, then the filtrate was concentrated to half volume and the process was repeated to provide two additional crops. A white solid was obtained as the title compound (23 g). LCMS m/z=234.3 [M+H]$^+$. $^1$H NMR (400 MHz, DMSO-d$_6$) δ ppm 1.41 (d, J=6.6 Hz, 3H), 1.59-1.68 (m, 1H), 1.89-2.00 (m, 2H), 2.15-2.22 (m, 1H), 3.00-3.07 (m, 2H), 3.11-3.19 (m, 2H), 3.37-3.50 (m, 2H), 3.57-3.65 (m, 1H), 4.80-6.75 (bs, 3H), 7.27 (d, J=7.6 Hz, 2H), 7.76 (d, J=8.2 Hz, 2H).

Example 1.2

Preparation of (R)-2-(2-(4'-(2-(2-Methylpyrrolidin-1-yl)ethyl)biphenyl-4-yl)ethoxy)acetic Acid (Compound 6)

Step A: Preparation of (R)-2-(4'-(2-(2-Methylpyrrolidin-1-yl)ethyl)biphenyl-4-yl)ethanol A mixture of (R)-4-(2-(2-methylpyrrolidin-1-yl)ethyl) phenylboronic acid (1.00 g, 4.29 mmol), 2-(4-bromophenyl) ethanol (0.862 g, 4.29 mmol), 2M Na$_2$CO$_3$ (2.145 mL, 4.29 mmol), and tetrakis(triphenylphosphine)palladium(0) (0.149 g, 0.129 mmol) in toluene (3 mL) and MeOH (0.857 mL) was heated at 100° C. under microwave irradiation for 2.5 h. The mixture was extracted with EtOAc, toluene and DCM. The combined organics were concentrated. The residue was purified by column chromatography and recrystallized from EtOAc to give the title compound. LCMS m/z=310.5 [M+H]$^+$.

Step B: Preparation of (R)-2-(2-(4'-(2-(2-Methylpyrrolidin-1-yl)ethyl)biphenyl-4-yl)ethoxy)acetic Acid (Compound 6)

To a solution of (R)-2-(4'-(2-(2-methylpyrrolidin-1-yl) ethyl)biphenyl-4-yl)ethanol (80 mg, 0.259 mmol) and tert-butyl 2-bromoacetate (605 mg, 3.10 mmol) in CHCl$_3$ (3 mL) was added 2M Na$_2$CO$_3$ (1.939 mL, 3.88 mmol). The mixture was stirred overnight at 55° C. The aqueous layer was separated, washed with DCM, and neutralized with 2M HCl. The aqueous mixture was then purified by HPLC. LCMS m/z=368.4 [M+H]$^+$.

Example 1.3

Preparation of (R)-1-(2-(4'-(2-(2-Methylpyrrolidin-1-yl)ethyl)biphenyl-4-yl)ethyl)-1H-tetrazole (Compound 7) & (R)-2-(2-(4'-(2-(2-Methylpyrrolidin-1-yl)ethyl)biphenyl-4-yl)ethyl)-2H-tetrazole (Compound 8)

To a mixture of (R)-2-(4'-(2-(2-methylpyrrolidin-1-yl) ethyl)biphenyl-4-yl)ethanol (50 mg, 0.162 mmol), 1H-tetrazole (11.32 mg, 0.162 mmol), and triphenylphosphine (50.9 mg, 0.194 mmol) in DMF (1.5 mL) was added DIAD (0.038 mL, 0.194 mmol). The reaction was stirred at room temperature for 2 h. To the mixture was added H$_2$O (1.5 mL) and extracted with 1:1 EtOAc/Hexane (2×5 mL). The aqueous layer was separated and purified by HPLC to give one regioisomer of the title compound. The organic layer was extracted with 2M HCl (2×2 mL). The HCl solution was purified by HPLC separately to give the other regioisomer of the title compound. Regioisomer 1: LCMS m/z=362.4 [M+H]$^+$; Regioisomer 2: LCMS m/z=362.4 [M+H]$^+$.

Example 1.4

Preparation of (R)-Methyl 3-(4'-(2-(2-Methylpyrrolidin-1-yl)ethyl)biphenyl-4-yl)propanoate (Compound 9)

To (R)-3-(4'-(2-(2-methylpyrrolidin-1-yl)ethyl)biphenyl-4-yl)propanoic acid (14.0 mg, 0.041 mmol, see Example 1.46 for preparation) was added 1.25M hydrogen chloride in methanol (0.996 mL, 1.245 mmol). The reaction was stirred at 60° C. for 2 h. The resulting mixture was concentrated and triturated with acetonitrile to give the title compound. LCMS m/z=352.4 [M+H]$^+$; $^1$H NMR (400 MHz, CD$_3$CN) δ ppm 1.24 (d, J=6.9 Hz, 0.5H), 1.56 (d, J=6.4 Hz, 2.5H), 1.76-1.90 (m, 1H), 1.99-2.14 (m, 2H), 2.23-2.38 (m, 1H), 2.68 (t, J=7.6 Hz, 2H), 2.97 (t, J=7.6 Hz, 2H), 3.00-3.21 (m, 3H), 3.30-3.41 (m, 2H), 3.45-3.55 (m, 1H), 3.65 (s, 3H), 3.69-3.80 (m, 1H), 7.33 (d, J=8.1 Hz, 2H), 7.40 (d, J=8.2 Hz, 2H), 7.58 (d, J=8.2 Hz, 2H), 7.62 (d, J=8.2 Hz, 2H).

Example 1.5

Preparation of (R)-2-Methyl-2-(4'-(2-(2-methylpyrrolidin-1-yl)ethyl)biphenyl-4-yl)propanoic Acid (Compound 10)

A mixture of (R)-4-(2-(2-methylpyrrolidin-1-yl)ethyl) phenylboronic acid hydrochloride (50.9 mg, 0.189 mmol), 2-(4-chlorophenyl)-2-methylpropanoic acid (50 mg, 0.252 mmol), Na$_2$CO$_3$ (107 mg, 1.007 mmol), and dichlorobis(p-dimethylaminophenyldi-tert-butylphosphine)palladium (1.782 mg, 2.52 μmol) in 1,4-dioxane (1 mL) and H$_2$O (0.2 mL) was heated under microwave irradiation at 150° C. for 10 min. To the resulting mixture was added 2 M HCl (8 mL) and extracted with 5% EtOAc/hexane (10 mL). To the aqueous phase was added ACN (2 mL) to dissolve the solid precipitates. The mixture was purified by HPLC. LCMS m/z=352.4 [M+H]$^+$; $^1$H NMR (400 MHz, CD$_3$CN) δ ppm 1.12 (d, J=13.6 Hz, 0.4H), 1.35 (d, J=6.4 Hz, 2.6H), 1.48 (s, 6H), 1.57-1.72

(m, 1H), 1.89-2.00 (m, 2H), 2.09-2.21 (m, 1H), 2.93-3.11 (m, 4H), 3.22-3.35 (m, 1H), 3.37-3.48 (m, 1H), 3.62-3.75 (m, 1H), 7.27 (d, J=8.1 Hz, 2H), 7.37 (d, J=8.3 Hz, 2H), 7.51 (d, J=8.2 Hz, 2H), 7.52 (d, J=7.9 Hz, 2H).

Example 1.6

Preparation of (R)-Ethyl 3-(4'-(2-(2-Methylpyrrolidin-1-yl)ethyl)biphenyl-4-yl)propanoate (Compound 11)

To (R)-3-(4'-(2-(2-methylpyrrolidin-1-yl)ethyl)biphenyl-4-yl)propanoic acid (15.8 mg, 0.047 mmol) was added 1.25M hydrogen chloride in ethanol (1.124 mL, 1.405 mmol). The reaction was stirred at 60° C. for 2 h. The mixture was concentrated and triturated with acetonitrile to give the title compound. LCMS m/z=366.6 [M+H]$^+$; $^1$H NMR (400 MHz, CD$_3$CN) δ ppm 1.22 (t, J=7.1 Hz, 3H), 1.24 (d, J=6.9 Hz, 0.5H), 1.56 (d, J=6.5 Hz, 2.5H), 1.75-1.90 (m, 1H), 1.98-2.14 (m, 2H), 2.22-2.38 (m, 1H), 2.66 (t, J=7.4 Hz, 2H), 2.97 (t, J=7.6 Hz, 2H), 3.00-3.21 (m, 3H), 3.30-3.41 (m, 2H), 3.45-3.54 (m, 1H), 3.69-3.79 (m, 1H), 4.11 (q, J=7.1 Hz, 2H), 7.31 (d, J=8.1 Hz, 2H), 7.40 (d, J=8.1 Hz, 2H), 7.58 (d, J=8.1 Hz, 2H), 7.62 (d, J=8.1 Hz, 2H).

Example 1.7

Preparation of (R)-tert-Butyl 2-Methyl-2-(3-(4'-(2-(2-methylpyrrolidin-1-yl)ethyl)biphenyl-4-yl)propanamido)propanoate (Compound 12)

To a solution of (R)-3-(4'-(2-(2-methylpyrrolidin-1-yl)ethyl)biphenyl-4-yl)propanoic acid (40 mg, 0.119 mmol), tert-butyl 2-amino-2-methylpropanoate hydrochloride (27.8 mg, 0.142 mmol), and TEA (0.050 mL, 0.356 mmol) in tetrahydrofuran (1 mL) and acetonitrile (1 mL) was added HATU (54.1 mg, 0.142 mmol). The reaction mixture was stirred at 60° C. for 1.5 h and 1M HCl was added to neutralize the reaction solution. The resulting mixture was purified by HPLC to give the title compound. LCMS m/z=479.4 [M+H]$^+$; $^1$H NMR (400 MHz, CD$_3$CN) δ ppm 1.27 (d, J=6.9 Hz, 0.4H), 1.37 (s, 6H), 1.41 (s, 9H), 1.46 (d, J=6.5 Hz, 2.6H), 1.70-1.82 (m, 1H), 2.01-2.12 (m, 2H), 2.23-2.33 (m, 1H), 2.45 (t, J=7.8 Hz, 2H), 2.93 (t, J=7.6 Hz, 2H), 3.05-3.22 (m, 4H), 3.39-3.48 (m, 1H), 3.53-3.62 (m, 1H), 3.72-3.82 (m, 1H), 6.60 (s, 1H), 7.34 (d, J=8.2 Hz, 2H), 7.39 (d, J=8.2 Hz, 2H), 7.58 (d, J=8.2 Hz, 2H), 7.63 (d, J=8.2 Hz, 2H).

Example 1.8

Preparation of (S)-tert-Butyl 2-(3-(4'-(2-((R)-2-Methylpyrrolidin-1-yl)ethyl)biphenyl-4-yl)propanamido)propanoate (Compound 13)

To a solution of (R)-3-(4'-(2-(2-methylpyrrolidin-1-yl)ethyl)biphenyl-4-yl)propanoic acid (40 mg, 0.119 mmol), (S)-tert-butyl 2-aminopropanoate hydrochloride (25.8 mg, 0.142 mmol), and TEA (0.050 mL, 0.356 mmol) in tetrahydrofuran (1 mL) and acetonitrile (1 mL) was added HATU (54.1 mg, 0.142 mmol). The reaction was stirred at 60° C. for 2 h. The mixture was added 1M HCl (1 mL) and purified by HPLC to give the title compound. LCMS m/z=465.5 [M+H]$^+$; $^1$H NMR (400 MHz, CD$_3$CN) δ ppm 1.27 (d, J=6.7 Hz, 0.4H), 1.28 (d, J=7.2 Hz, 3H), 1.44 (s, 9H), 1.46 (d, J=6.6 Hz, 2.6H), 1.70-1.82 (m, 1H), 2.01-2.12 (m, 2H), 2.23-2.33 (m, 1H), 2.51 (t, J=7.8 Hz, 2H), 2.95 (t, J=7.7 Hz, 2H), 3.05-3.21 (m, 4H), 3.37-3.48 (m, 1H), 3.49-3.62 (m, 1H), 3.73-3.83 (m, 1H), 4.20-4.29 (m, 1H), 6.64 (d, 7.1 Hz, 1H), 7.34 (d, J=8.1 Hz, 2H), 7.39 (d, J=8.1 Hz, 2H), 7.58 (d, J=8.1 Hz, 2H), 7.63 (d, J=8.1 Hz, 2H).

Example 1.9

Preparation of (1R,2R)-Ethyl 2-(1-(4'-(2-((R)-2-Methylpyrrolidin-1-yl)ethyl)biphenyl-4-yl)cyclopentanecarboxamido)cyclohexanecarboxylate (Compound 14)

A mixture of (R)-1-(4'-(2-(2-methylpyrrolidin-1-yl)ethyl)biphenyl-4-yl)cyclopentanecarboxylic acid (15 mg, 0.040 mmol), (1S,2S)-ethyl 2-aminocyclohexanecarboxylate hydrochloride (9.08 mg, 0.044 mmol), HATU (16.62 mg, 0.044 mmol), and TEA (0.017 mL, 0.119 mmol) in DMF (0.4 mL) was stirred at room temperature overnight. The mixture was acidified with 1M HCl and purified by HPLC to give the title compound. LCMS m/z=531.6 [M+H]$^+$.

Example 1.10

Preparation of (R)-Ethyl 3-(1-(4'-(2-(2-Methylpyrrolidin-1-yl)ethyl)biphenyl-4-yl)cyclopentanecarboxamido)propanoate (Compound 15)

A mixture of (R)-1-(4'-(2-(2-methylpyrrolidin-1-yl)ethyl)biphenyl-4-yl)cyclopentanecarboxylic acid (15 mg, 0.040 mmol), ethyl 3-aminopropanoate hydrochloride (6.71 mg, 0.044 mmol), HATU (16.62 mg, 0.044 mmol), and TEA (0.017 mL, 0.119 mmol) in DMF (0.4 mL) was stirred at room temperature overnight. The mixture was acidified with 1M HCl and purified by HPLC to give the title compound. LCMS m/z=477.5.

Example 1.11

Preparation of (R)-Methyl 4-(1-(4'-(2-(2-Methylpyrrolidin-1-yl)ethyl)biphenyl-4-yl)cyclopentanecarboxamido)butanoate (Compound 16)

A mixture of (R)-1-(4'-(2-(2-methylpyrrolidin-1-yl)ethyl)biphenyl-4-yl)cyclopentanecarboxylic acid (15 mg, 0.040 mmol), methyl 4-aminobutanoate hydrochloride (6.71 mg, 0.044 mmol), HATU (16.62 mg, 0.044 mmol), and TEA (0.017 mL, 0.119 mmol) in DMF (0.4 mL) was stirred at room temperature overnight. The mixture was acidified with 1M HCl and purified by HPLC to give the title compound. LCMS m/z=477.5 [M+H]$^+$.

Example 1.12

Preparation of (R)-2-Methyl-2-(3-(4'-(2-(2-Methylpyrrolidin-1-yl)ethyl)biphenyl-4-yl)propanamido)propanoic acid (Compound 17)

To (R)-tert-butyl 2-methyl-2-(3-(4'-(2-(2-methylpyrrolidin-1-yl)ethyl)biphenyl-4-yl)propanamido)propanoate 2,2,2-trifluoroacetate (2.0 mg, 3.37 mol) was added 4M hydrogen chloride in dioxane (0.295 mL, 1.181 mmol). The reaction was stirred at room temperature for 4 h. The mixture was concentrated to give the title compound. LCMS m/z=423.3 [M+H]$^+$.

Example 1.13

Preparation of (S)-2-(3-(4'-(2-((R)-2-methylpyrrolidin-1-yl)ethyl)biphenyl-4-yl)propanamido)propanoic acid (Compound 18)

To (S)-tert-butyl 2-(3-(4'-(2-((R)-2-methylpyrrolidin-1-yl)ethyl)biphenyl-4-yl)propanamido)propanoate 2,2,2-trifluoroacetate (4.4 mg, 7.60 mol) was added 4M hydrogen chloride in dioxane (0.665 mL, 2.66 mmol). The reaction was stirred at room temperature for 4 h. The mixture was concentrated to give the title compound. LCMS m/z=409.4 [M+H]$^+$.

Example 1.14

Preparation of (R)-1-(4'-(2-(2-Methylpyrrolidin-1-yl)ethyl)biphenyl-4-yl)cyclopentanecarboxylic Acid (Compound 19)

A mixture of (R)-4-(2-(2-methylpyrrolidin-1-yl)ethyl)phenylboronic acid hydrochloride (300 mg, 1.113 mmol), 1-(4-chlorophenyl)cyclopentanecarboxylic acid (300 mg, 1.335 mmol), Na$_2$CO$_3$ (472 mg, 4.45 mmol), and dichlorobis(p-dimethylaminophenyldi-tert-butylphosphine)palladium (7.88 mg, 0.011 mmol) in 1,4-dioxane (6 mL) and H$_2$O (1.2 mL) was heated under microwave irradiation at 150° C. for 10 min. The mixture was concentrated. The residue was purified by HPLC to give the title compound. LCMS m/z=378.3 [M+H]$^+$.

Example 1.15

Preparation of (1R,2S)-Ethyl 2-(1-(4'-(2-((R)-2-Methylpyrrolidin-1-yl)ethyl)biphenyl-4-yl)cyclopentanecarboxamido)cyclohexanecarboxylate (Compound 20)

A mixture of (R)-1-(4'-(2-(2-methylpyrrolidin-1-yl)ethyl)biphenyl-4-yl)cyclopentanecarboxylic acid (15 mg, 0.040 mmol), (1R,2S)-ethyl 2-aminocyclohexanecarboxylate hydrochloride (9.08 mg, 0.044 mmol), HATU (16.62 mg, 0.044 mmol), and TEA (0.017 mL, 0.119 mmol) in DMF (0.4 mL) was stirred at room temperature overnight. The mixture was acidified with 1M HCl and purified by HPLC to give the title compound. LCMS m/z=531.7 [M+H]$^+$; $^1$H NMR (400 MHz, CD$_3$CN) δ ppm 1.13 (t, J=7.1 Hz, 3H), 1.27 (d, J=6.8 Hz, 0.4H), 1.32-1.41 (m, 3H), 1.41-1.54 (m, 2H), 1.46 (d, J=7.1 Hz, 2.6H), 1.55-1.66 (m, 2H), 1.67-1.84 (m, 6H), 1.98-2.11 (m, 3H), 2.22-2.32 (m, 1H), 2.45-2.55 (m, 3H), 2.62-2.68 (m, 1H), 3.06-3.18 (m, 4H), 3.35-3.47 (m, 1H), 3.49-3.60 (m, 1H), 3.73-3.85 (m, 1H), 3.92-4.01 (m, 2H), 4.02-4.11 (m, 1H), 6.19 (d, J=8.3 Hz, 1H), 7.40 (d, J=8.2 Hz, 2H), 7.45 (d, J=8.3 Hz, 2H), 7.60-7.67 (m, 4H).

Example 1.16

Preparation of (R)-Methyl 3-(1-(4'-(2-(2-Methylpyrrolidin-1-yl)ethyl)biphenyl-4-yl)cyclopentanecarboxamido)propanoate (Compound 21)

A mixture of (R)-1-(4'-(2-(2-methylpyrrolidin-1-yl)ethyl)biphenyl-4-yl)cyclopentanecarboxylic acid (15 mg, 0.040 mmol), methyl 3-aminopropanoate hydrochloride (6.10 mg, 0.044 mmol), HATU (16.62 mg, 0.044 mmol), and TEA (0.017 mL, 0.119 mmol) in DMF (0.4 mL) was stirred at room temperature overnight. The mixture was acidified with 1M HCl and purified by HPLC. LCMS m/z=463.2 [M+H]$^+$.

Example 1.17

Preparation of (R)-tert-Butyl 3-(1-(4'-(2-(2-Methylpyrrolidin-1-yl)ethyl)biphenyl-4-yl)cyclopentanecarboxamido)propanoate (Compound 22)

A mixture of (R)-1-(4'-(2-(2-methylpyrrolidin-1-yl)ethyl)biphenyl-4-yl)cyclopentanecarboxylic acid (15 mg, 0.040 mmol), tert-butyl 3-aminopropanoate hydrochloride (7.94 mg, 0.044 mmol), HATU (16.62 mg, 0.044 mmol), and TEA (0.017 mL, 0.119 mmol) in DMF (0.4 mL) was stirred at room temperature overnight. The mixture was acidified with 1M HCl and purified by HPLC. LCMS m/z=505.5 [M+H]$^+$.

Example 1.18

Preparation of (R)-tert-Butyl 4-(1-(4'-(2-(2-Methylpyrrolidin-1-yl)ethyl)biphenyl-4-yl)cyclopentanecarboxamido)butanoate (Compound 23)

A mixture of (R)-1-(4'-(2-(2-methylpyrrolidin-1-yl)ethyl)biphenyl-4-yl)cyclopentanecarboxylic acid (15 mg, 0.040 mmol), tert-butyl 4-aminobutanoate hydrochloride (8.55 mg, 0.044 mmol), HATU (16.62 mg, 0.044 mmol), and TEA (0.017 mL, 0.119 mmol) in DMF (0.4 mL) was stirred at room temperature overnight. The mixture was acidified with 1M HCl and purified by HPLC. LCMS m/z=519.7 [M+H]$^+$.

Example 1.19

Preparation of (R)-Methyl 2-(3-(4'-(2-(2-Methylpyrrolidin-1-yl)ethyl)biphenyl-4-yl)propanamido)acetate (Compound 24)

To a solution of (R)-3-(4'-(2-(2-methylpyrrolidin-1-yl)ethyl)biphenyl-4-yl)propanoic acid (40 mg, 0.119 mmol), methyl 2-aminoacetate hydrochloride (19.35 mg, 0.154 mmol), and TEA (0.050 mL, 0.356 mmol) in tetrahydrofuran (1 mL) and acetonitrile (1 mL) was added HATU (54.1 mg, 0.142 mmol). The reaction was stirred at 60° C. for 2 h. The mixture was added 1M HCl and purified by HPLC to give the title compound. LCMS m/z=409.1 [M+H]$^+$; $^1$H NMR (400 MHz, CD$_3$CN) δ ppm 1.27 (d, J=6.8 Hz, 0.3H), 1.46 (d, J=6.5 Hz, 2.7H), 1.70-1.82 (m, 1H), 2.01-2.12 (m, 2H), 2.23-2.33 (m, 1H), 2.56 (t, J=7.7 Hz, 2H), 2.96 (t, J=7.8 Hz, 2H), 3.07-3.21 (m, 4H), 3.36-3.47 (m, 1H), 3.49-3.61 (m, 1H), 3.69 (s, 3H), 3.73-3.83 (m, 1H), 3.90 (d, 6.0 Hz, 2H), 6.80 (s, 1H), 7.34 (d, J=8.1 Hz, 2H), 7.38 (d, J=8.1 Hz, 2H), 7.57 (d, J=8.1 Hz, 2H), 7.63 (d, J=8.2 Hz, 2H).

Example 1.20

Preparation of (R)-Methyl 1-(4'-(2-(2-Methylpyrrolidin-1-yl)ethyl)biphenyl-4-yl)cyclopentanecarboxylate (Compound 25)

To (R)-1-(4'-(2-(2-methylpyrrolidin-1-yl)ethyl)biphenyl-4-yl)cyclopentanecarboxylic acid (30.0 mg, 0.079 mmol) was added 1.25M hydrogen chloride in methanol (1.907 mL, 2.384 mmol). The reaction was stirred at room temperature for 4 h. The mixture was concentrated and purified by HPLC to give the title compound. LCMS m/z=392.5 [M+H]$^+$; $^1$H NMR (400 MHz, CD$_3$CN) δ ppm 1.27 (d, J=6.9 Hz, 0.3H), 1.46 (d, J=6.5 Hz, 2.7H), 1.67-1.84 (m, 5H), 2.01-2.12 (m, 2H), 2.23-2.33 (m, 1H), 2.59-2.67 (m, 1H), 3.05-3.21 (m, 4H), 3.36-3.47 (m, 1H), 3.51-3.58 (m, 1H), 3.61 (s, 3H), 3.73-3.84 (m, 1H), 7.40 (d, J=8.2 Hz, 2H), 7.46 (d, J=8.3 Hz, 2H), 7.62 (d, J=8.5 Hz, 2H), 7.65 (d, J=8.3 Hz, 2H).

Example 1.21

Preparation of (R)-tert-Butyl 2-(3-(4'-(2-(2-Methylpyrrolidin-1-yl)ethyl)biphenyl-4-yl)propanamido)acetate (Compound 26)

To a solution of (R)-3-(4'-(2-(2-methylpyrrolidin-1-yl)ethyl)biphenyl-4-yl)propanoic acid (40 mg, 0.119 mmol), tert-butyl 2-aminoacetate (18.66 mg, 0.142 mmol), and TEA (0.033 mL, 0.237 mmol) in DMF (1 mL) was added HATU (54.1 mg, 0.142 mmol). The reaction was stirred at 60° C. for 2 h. The mixture was added 1M HCl (1 mL) and purified by HPLC to give the title compound. LCMS m/z=451.4 [M+H]$^+$; $^1$H NMR (400 MHz, CD$_3$CN) δ ppm 1.27 (d, J=6.9 Hz, 0.4H), 1.45 (s, 9H), 1.47 (d, J=6.5 Hz, 2.6H), 1.71-1.83 (m, 1H), 2.02-2.12 (m, 2H), 2.23-2.33 (m, 1H), 2.55 (t, J=7.5 Hz, 2H), 2.96 (t, J=7.8 Hz, 2H), 3.06-3.21 (m, 4H), 3.37-3.47 (m, 1H), 3.50-3.63 (m, 1H), 3.72-3.84 (m, 1H), 6.63 (s, 1H), 7.35 (d, J=8.2 Hz, 2H), 7.39 (d, J=8.2 Hz, 2H), 7.58 (d, J=8.2 Hz, 2H), 7.64 (d, J=8.2 Hz, 2H).

Example 1.22

Preparation of (R)-Methyl 2-(1-(4'-(2-(2-Methylpyrrolidin-1-yl)ethyl)biphenyl-4-yl)cyclopentanecarboxamido)acetate (Compound 27)

A mixture of (R)-1-(4'-(2-(2-methylpyrrolidin-1-yl)ethyl)biphenyl-4-yl)cyclopentanecarboxylic acid (15 mg, 0.040 mmol), methyl 2-aminoacetate hydrochloride (5.49 mg, 0.044 mmol), HATU (16.62 mg, 0.044 mmol), and TEA (0.017 mL, 0.119 mmol) in DMF (0.4 mL) was stirred at room temperature overnight. The mixture was acidified with 1M HCl and purified by HPLC to give the title compound. LCMS m/z=449.3 [M+H]$^+$.

Example 1.23

Preparation of (S)-Methyl 2-(1-(4'-(2-((R)-2-Methylpyrrolidin-1-yl)ethyl)biphenyl-4-yl)cyclopentanecarboxamido)propanoate (Compound 28)

A mixture of (R)-1-(4'-(2-(2-methylpyrrolidin-1-yl)ethyl)biphenyl-4-yl)cyclopentanecarboxylic acid (15 mg, 0.040 mmol), (S)-methyl 2-aminopropanoate hydrochloride (6.10 mg, 0.044 mmol), HATU (16.62 mg, 0.044 mmol), and TEA (0.017 mL, 0.119 mmol) in DMF (0.4 mL) was stirred at room temperature overnight. The mixture was acidified with 1M HCl and purified by HPLC to give the title compound. LCMS m/z=449.3 [M+H]$^+$.

Example 1.24

Preparation of (R)-2-(3-(4'-(2-(2-Methylpyrrolidin-1-yl)ethyl)biphenyl-4-yl)propanamido)acetic Acid (Compound 29)

To a solution of (R)-methyl 2-(3-(4'-(2-(2-methylpyrrolidin-1-yl)ethyl)biphenyl-4-yl)propanamido)acetate 2,2,2-trifluoroacetate (18 mg, 0.034 mmol) in MeOH (0.5 mL) was added 5M sodium hydroxide (0.048 mL, 0.241 mmol). The reaction was stirred at room temperature overnight. The mixture was added 1M HCl (2 mL) and purified by HPLC to give the title compound. LCMS m/z=395.2 [M+H]$^+$.

Example 1.25

Preparation of (1R,2R)-2-(1-(4'-(2-((R)-2-Methylpyrrolidin-1-yl)ethyl)biphenyl-4-yl)cyclopentanecarboxamido)cyclohexanecarboxylic Acid (Compound 30)

To (1R,2R)-ethyl 2-(1-(4'-(2-((R)-2-methylpyrrolidin-1-yl)ethyl)biphenyl-4-yl)cyclopentanecarboxamido)cyclohexanecarboxylate 2,2,2-trifluoroacetate (2.7 mg, 4.19 μmol) was added 5M sodium hydroxide (0.017 mL, 0.084 mmol). The reaction was stirred at room temperature overnight. The mixture was neutralized with 4M HCl in dioxane. The mixture was concentrated and triturated with acetonitrile to give the title compound. LCMS m/z=503.5 [M+H]$^+$.

Example 1.26

Preparation of (R)-tert-Butyl 3-(3-(4'-(2-(2-Methylpyrrolidin-1-yl)ethyl)biphenyl-4-yl)propanamido)propanoate (Compound 31)

To a solution of (R)-3-(4'-(2-(2-methylpyrrolidin-1-yl)ethyl)biphenyl-4-yl)propanoic acid (30 mg, 0.089 mmol), tert-butyl 3-aminopropanoate hydrochloride (19.38 mg, 0.107 mmol), and TEA (0.037 mL, 0.267 mmol) in DMF (1 mL) was added HATU (40.6 mg, 0.107 mmol). The reaction was stirred at room temperature overnight. The mixture was added H$_2$O (1 mL) and 1M HCl (1 mL) and purified by HPLC to give the title compound. LCMS m/z=465.5 [M+H]$^+$; $^1$H NMR (400 MHz, CD$_3$CN) δ ppm 1.27 (d, J=6.8 Hz, 0.4H), 1.44 (s, 9H), 1.46 (d, J=6.5 Hz, 2.6H), 1.69-1.82 (m, 1H), 2.02-2.12 (m, 2H), 2.23-2.32 (m, 1H), 2.35 (t, J=6.6 Hz, 2H), 2.46 (t, J=7.6 Hz, 2H), 2.93 (t, J=7.6 Hz, 2H), 3.05-3.22 (m, 4H), 3.31-3.38 (m, 2H), 3.38-3.49 (m, 1H), 3.52-3.63 (m, 1H), 3.72-3.82 (m, 1H), 6.50 (s, 1H), 7.32 (d, J=8.1 Hz, 2H), 7.39 (d, J=8.2 Hz, 2H), 7.57 (d, J=8.2 Hz, 2H), 7.63 (d, J=8.2 Hz, 2H).

Example 1.27

Preparation of (S)-1-(3-(4'-(2-((R)-2-Methylpyrrolidin-1-yl)ethyl)biphenyl-4-yl)propanoyl)pyrrolidine-2-carboxylic Acid (Compound 32)

To a solution of (R)-3-(4'-(2-(2-methylpyrrolidin-1-yl)ethyl)biphenyl-4-yl)propanoic acid (15 mg, 0.044 mmol), TEA (0.019 mL, 0.133 mmol), and HATU (25.4 mg, 0.067 mmol) in THF (0.5 mL) and DCM (0.500 mL) was added (S)-trimethylsilyl 1-(trimethylsilyl)pyrrolidine-2-carboxylate (23.07 mg, 0.089 mmol). The reaction mixture was stirred at room temperature overnight. The mixture was concentrated and the residue purified by HPLC to give the title compound. LCMS m/z=435.4 [M+H]$^+$.

Example 1.28

Preparation of (R)-4-(1-(4'-(2-(2-Methylpyrrolidin-1-yl)ethyl)biphenyl-4-yl)cyclopentanecarboxamido)butanoic Acid (Compound 33)

To (R)-tert-butyl 4-(1-(4'-(2-(2-methylpyrrolidin-1-yl)ethyl)biphenyl-4-yl)cyclopentanecarboxamido)butanoate 2,2,2-trifluoroacetate (2.6 mg, 4.11 μmol) was added 4M hydrogen chloride in dioxane (0.103 mL, 0.411 mmol). The reaction was stirred at room temperature overnight. The mixture was concentrated to give the title compound. LCMS m/z=463.4 [M+H]$^+$.

Example 1.29

Preparation of (R)-tert-Butyl 4-(3-(4'-(2-(2-Methylpyrrolidin-1-yl)ethyl)biphenyl-4-yl)propanamido)butanoate (Compound 34)

To a solution of (R)-3-(4'-(2-(2-methylpyrrolidin-1-yl)ethyl)biphenyl-4-yl)propanoic acid (30 mg, 0.089 mmol), tert-butyl 4-aminobutanoate hydrochloride (20.88 mg, 0.107 mmol), and TEA (0.037 mL, 0.267 mmol) in DMF (1 mL) was added HATU (40.6 mg, 0.107 mmol). The reaction was stirred at room temperature overnight. The mixture was added 1M HCl (1 mL) and purified by HPLC to give the title compound. LCMS m/z=479.3 [M+H]$^+$.

Example 1.30

Preparation of (R)-Ethyl 1-(3-(4'-(2-(2-Methylpyrrolidin-1-yl)ethyl)biphenyl-4-yl)propanoyl)piperidine-4-carboxylate (Compound 35)

To a solution of (R)-3-(4'-(2-(2-methylpyrrolidin-1-yl)ethyl)biphenyl-4-yl)propanoic acid (30 mg, 0.089 mmol), ethyl piperidine-4-carboxylate (16.77 mg, 0.107 mmol), and TEA (0.025 mL, 0.178 mmol) in DMF (1 mL) was added HATU (40.6 mg, 0.107 mmol). The reaction was stirred at room temperature overnight. The mixture was added 1M HCl (2 mL) and purified by HPLC to give the title compound. LCMS m/z=477.5 [M+H]$^+$; 1.19 (t, J=7.1 Hz, 3H), 1.25 (d, J=6.8 Hz, 0.3H), 1.37-1.50 (m, 2H), 1.44 (d, J=6.7 Hz, 2.7H), 1.67-1.77 (m, 1H), 1.77-1.89 (m, 2H), 1.99-2.09 (m, 2H), 2.20-2.31 (m, 1H), 2.45-2.56 (m, 1H), 2.57-2.79 (m, 3H), 2.92 (t, J=6.6 Hz, 2H), 3.00-3.19 (m, 5H), 3.34-3.47 (m, 1H), 3.50-3.59 (m, 1H), 3.70-3.86 (m, 2H), 4.06 (q, J=7.0 Hz, 2H), 3.70-3.86 (m, 2H), 7.32 (d, J=8.1 Hz, 2H), 7.36 (d, J=8.2 Hz, 2H), 7.54 (d, J=8.2 Hz, 2H), 7.60 (d, J=8.2 Hz, 2H).

Example 1.31

Preparation of (R)-5-((4'-(2-(2-Methylpyrrolidin-1-yl)ethyl)biphenyl-4-yl)methyl)-1H-tetrazole (Compound 37)

A mixture of (R)-4-(2-(2-methylpyrrolidin-1-yl)ethyl)phenylboronic acid hydrochloride (50 mg, 0.185 mmol), 5-(4-bromobenzyl)-1H-tetrazole (53.2 mg, 0.223 mmol), Na$_2$CO$_3$ (79 mg, 0.742 mmol), and dichlorobis(p-dimethylaminophenyldi-tert-butylphosphine)palladium (1.313 mg, 1.855 µmol) in 1,4-dioxane (1 mL) and H$_2$O (0.2 mL) was heated under microwave irradiation at 130° C. for 120 min. The mixture was concentrated. The residue was purified by HPLC to give the title compound. LCMS m/z=348.1 [M+H]$^+$; $^1$H NMR (400 MHz, CD$_3$CN) δ ppm 1.27 (d, J=6.5 Hz, 0.4H), 1.46 (d, J=6.6 Hz, 2.6H), 1.70-1.82 (m, 1H), 2.02-2.11 (m, 2H), 2.22-2.33 (m, 1H), 3.05-3.21 (m, 4H), 3.36-3.48 (m, 1H), 3.52-3.62 (m, 1H), 3.72-3.83 (m, 1H), 4.36 (s, 2H), 7.36-7.44 (m, 4H), 7.61-7.67 (m, 4H).

Example 1.32

Preparation of (R)-5-(2-(4'-(2-(2-Methylpyrrolidin-1-yl)ethyl)biphenyl-4-yl)ethyl)-1H-tetrazole (Compound 44)

A mixture of (R)-4-(2-(2-methylpyrrolidin-1-yl)ethyl)phenylboronic acid hydrochloride (50 mg, 0.185 mmol), 5-(4-bromophenethyl)-1H-tetrazole (56.3 mg, 0.223 mmol), Na$_2$CO$_3$ (79 mg, 0.742 mmol), and dichlorobis(p-dimethylaminophenyldi-tert-butylphosphine)palladium (1.313 mg, 1.855 µmol) in 1,4-dioxane (1 mL) and H$_2$O (0.2 mL) was heated under microwave irradiation at 130° C. for 120 min. The mixture was concentrated and the residue was purified by HPLC to give the title compound. LCMS m/z=362.5 [M+H]$^+$; 1.22-1.31 (m, 0.4H), 1.45 (d, J=6.6 Hz, 2.6H), 1.69-1.82 (m, 1H), 2.00-2.10 (m, 2H), 2.21-2.32 (m, 1H), 3.04-3.20 (m, 6H), 3.25-3.31 (m, 2H), 3.35-3.47 (m, 1H), 3.50-3.60 (m, 1H), 3.72-3.83 (m, 1H), 7.31 (d, J=8.1 Hz, 2H), 7.37 (d, J=8.1 Hz, 2H), 7.56 (d, J=8.2 Hz, 2H), 7.61 (d, J=8.2 Hz, 2H).

Example 1.33

Preparation of (R)-4-(4'-(2-(2-Methylpyrrolidin-1-yl)ethyl)biphenyl-4-yl)butanoic Acid (Compound 45)

In a microwave reaction vial was placed (R)-4-(2-(2-methylpyrrolidin-1-yl)ethyl)phenylboronic acid hydrochloride (50 mg, 0.185 mmol), 4-(4-bromophenyl)butanoic acid (49.6 mg, 0.204 mmol), dichlorobis(p-dimethylaminophenyldi-tert-butylphosphine)palladium (2.63 mg, 3.71 µmol), and K$_2$CO$_3$ (51.3 mg, 0.371 mmol) in toluene (1.2 mL) and H$_2$O (0.2 mL). The reaction was heated at 130° C. for 120 min under microwave irradiation. The aqueous layer was collected, acidified with 1M HCl, and purified by HPLC to give the title compound. LCMS m/z=352.4 [M+H]$^+$; 1.26 (d, J=6.8 Hz, 0.4H), 1.46 (d, J=6.5 Hz, 2.6H), 1.70-1.82 (m, 1H), 1.87-1.94 (m, 2H), 2.01-2.10 (m, 2H), 2.21-2.30 (m, 1H), 2.33 (t, J=7.4 Hz, 2H), 2.70 (t, J=7.7 Hz, 2H), 3.06-3.18 (m, 4H), 3.35-3.45 (m, 1H), 3.50-3.60 (m, 1H), 3.74-3.84 (m, 1H), 7.31 (d, J=8.3 Hz, 2H), 7.38 (d, J=8.2 Hz, 2H), 7.58 (d, J=8.3 Hz, 2H), 7.63 (d, J=8.3 Hz, 2H).

Example 1.34

Preparation of (R)-Ethyl 4-(4'-(2-(2-Methylpyrrolidin-1-yl)ethyl)biphenyl-4-yl)butanoate (Compound 46) as the HCl Salt To (R)-4-(4'-(2-(2-methylpyrrolidin-1-yl)ethyl)biphenyl-4-yl)butanoic acid compound with 2,2,2-trifluoroacetic acid (1:1) (1.0 mg, 2.148 µmol) was added 1.25M hydrogen chloride in ethanol (0.687 mL, 0.859 mmol). The reaction was stirred at room temperature for 1 h. The mixture was concentrated to give the title compound. LCMS m/z=380.2 [M+H]$^+$.

Example 1.35

Preparation of (R)-Ethyl 2-((4'-(2-(2-Methylpyrrolidin-1-yl)ethyl)biphenyl-4-yl)methoxy)acetate (Compound 4)

Step A: Preparation of Ethyl 2-(4-Bromobenzyloxy)acetate

To a solution of (4-bromophenyl)methanol (1.0 g, 5.35 mmol) in DCM (25 mL) cooled in an ice bath was added rhodium(II) acetate dimmer (0.236 g, 0.535 mmol). To the resulting mixture was slowly added a solution of ethyl diazoacetate (0.721 mL, 6.95 mmol) in DCM (1 mL). The reaction mixture was stirred for 0.5 h. Additional ethyl diazoacetate (300 µL) was added and the resulting mixture was stirred for an additional 0.5 h. The mixture was concentrated and the residue was purified by chromatography (0, 5, 10, 15% EtOAc/Hexanes) to give the title compound. LCMS m/z=273.2 [M+H]$^+$; $^1$H NMR (400 MHz, DMSO-d$_6$) δ ppm 1.21 (t, J=7.1 Hz, 3H), 4.12-4.15 (m, 2H), 4.16 (s, 2H), 4.52 (s, 2H), 7.31 (d, J=8.3 Hz, 2H), 7.55 (d, J=8.3 Hz, 2H).

Step B: Preparation of (R)-Ethyl 2-((4'-(2-(2-Methylpyrrolidin-1-yl)ethyl)biphenyl-4-yl)methoxy)acetate Ethyl 2-(4-bromobenzyloxy)acetate (304 mg, 1.113 mmol), (R)-4-(2-(2-methylpyrrolidin-1-yl)ethyl)phenylboronic acid hydrochloride (300 mg, 1.113 mmol), tetrakis(triphenylphosphine)palladium(0) (64.3 mg, 0.056 mmol) and 2M Na$_2$CO$_3$ (aq.) (1113 µL, 2.226 mmol) were added to a vial with benzene (2 mL) and EtOH (0.6 mL). The reaction was heated under microwave irradiation at 100° C. for an hour and 120° C. for 0.5 h. The reaction was diluted with H$_2$O (1 mL) and extracted with EtOAc (3×2 mL). The combined organics were filtered through a plug of MgSO$_4$. The solvent was evaporated and the residue was purified by column chromatography and prep LCMS to give the title compound. LCMS m/z=382.2 [M+H]$^+$; $^1$H NMR (400 MHz, DMSO-d$_6$) δ ppm 1.18-1.26 (m, 3H), 1.39 (d, J=6.4 Hz, 3H), 1.54-1.70 (m, 1H), 1.85-2.12 (m, 2H), 2.15-2.29 (m, 1H), 2.96-3.14 (m, 2H), 3.14-3.28 (m, 2H), 3.40-3.49 (m, 1H), 3.54 (d, J=20.3 Hz, 1H), 3.59-3.70 (m, 1H), 4.09-4.21 (m, 4H), 4.59 (s, 2H), 7.36-7.49 (m, 4H), 7.66 (d, J=7.71 Hz, 4H), 9.51-10.13 (m, 1H).

Example 1.36

Preparation of (R)-2-((4'-(2-(2-Methylpyrrolidin-1-yl)ethyl)biphenyl-4-yl)methoxy)acetic Acid (Compound 5)

To a solution of (R)-Ethyl 2-((4'-(2-(2-methylpyrrolidin-1-yl)ethyl)biphenyl-4-yl)methoxy)acetate (125.6 mg, 0.329 mmol) in THF (0.5 mL), MeOH (0.5 mL), and H$_2$O (1 mL) was added LiOH (23.65 mg, 0.988 mmol). The reaction was heated briefly to ~50° C. and concentrated. The resulting aqueous mixture was acidified (HCl, 3 eq) and purified by HPLC to give the title compound. LCMS m/z=354.4 [M+H]$^+$; $^1$H NMR (400 MHz, DMSO-d$_6$) δ ppm 1.37 (t, J=5.94 Hz, 3H), 1.53-1.70 (m, 1H), 1.86-2.13 (m, 2H), 2.16-2.28 (m, 1H), 2.91-3.13 (m, 2H), 3.16-3.27 (m, 2H), 3.51-3.71 (m, 3H), 4.09 (s, 2H), 4.58 (s, 2H), 7.37-7.47 (m, 4H), 7.61-7.70 (m, 4H), 9.26-9.84 (m, 1H), 12.68 (bs, 1H).

Example 1.37

Preparation of (R)-4-(4'-(2-(2-Methylpyrrolidin-1-yl)ethyl)biphenyl-4-yl)-4-oxobutanoic Acid (Compound 36)

To a 2 mL heavy-walled tube was added (R)-4-(2-(2-methylpyrrolidin-1-yl)ethyl)phenylboronic acid hydrochloride (127 mg, 0.471 mmol), 4-(4-chlorophenyl)-4-oxobutanoic acid (91 mg, 0.428 mmol), Na$_2$CO$_3$ (136 mg, 1.284 mmol), dichlorobis(p-dimethylaminophenyldi-tert-butylphosphine) palladium (3.03 mg, 4.28 µmol), dioxane (1 mL), and water (0.15 mL). The tube was sealed and heated to 150° C. for 10 min under microwave irradiation. The mixture was purified by preparative HPLC to give the title compound as a white solid. LCMS m/z=366.1 [M+H]; $^1$H NMR (400 MHz, DMSO-d$_6$) δ ppm 1.20 (d, J=6.3 Hz, 0.4H), 1.37 (d, J=6.3 Hz, 2.6H), 1.54-1.65 (m, 1H), 1.90-2.05 (m, 2H), 2.18-2.26 (m, 1H), 2.62 (t, J=7.8 Hz, 2H), 2.95-3.10 (m, 2H), 3.16-3.30 (m, 3H), 3.38-3.68 (m, 4H), 7.46 (d, J=8.2 Hz, 2H), 7.74 (d, J=8.2 Hz, 2H), 7.84 (d, J=8.2 Hz, 2H), 8.06 (d, J=8.2 Hz, 2H), 9.34 (bs, 1H).

Example 1.38

Preparation of (R)-Methyl 2-Methyl-2-(4'-(2-(2-methylpyrrolidin-1-yl)ethyl)biphenyl-4-ylcarboxamido) propanoate (Compound 38)

To a 2 mL scintillation vial was added (R)-4'-(2-(2-methylpyrrolidin-1-yl)ethyl)biphenyl-4-carboxylic acid (60 mg, 0.194 mmol), methyl 2-amino-2-methylpropanoate (22.72 mg, 0.194 mmol), 2-(3H-[1,2,3]triazolo[4,5-b]pyridin-3-yl)-1,1,3,3-tetramethylisouronium hexafluorophosphate(V) (81 mg, 0.213 mmol), N-ethyl-N-isopropylpropan-2-amine (0.069 mL, 0.388 mmol) and ACN (1 mL). The vial was sealed and stirred at 28° C. for 10 min. The mixture was purified by preparative HPLC to give the title compound as a white solid. LCMS m/z=409.4 [M+H]$^+$; $^1$H NMR (400 MHz, DMSO-d$_6$) δ ppm 1.20 (d, J=6.3 Hz, 0.4H), 1.37 (d, J=6.3 Hz, 2.6H), 1.50 (s, 6H), 1.54-1.65 (m, 1H), 1.90-2.05 (m, 2H), 2.18-2.26 (m, 1H), 2.95-3.10 (m, 2H), 3.16-3.30 (m, 2H), 3.40-3.50 (m, 2H), 3.52-3.56 (m, 1H), 3.60 (s, 3H), 3.63-3.70 (m, 2H), 7.46 (d, J=8.2 Hz, 2H), 7.72 (d, J=8.2 Hz, 2H), 7.77 (d, J=8.2 Hz, 2H), 7.96 (d, J=8.2 Hz, 2H), 8.63 (s, 1H), 9.44 (bs, 1H).

Example 1.39

Preparation of (R)-Methyl 3-(4'-(2-(2-Methylpyrrolidin-1-yl)ethyl)biphenyl-4-ylcarboxamido)propanoate (Compound 39)

From (R)-4'-(2-(2-methylpyrrolidin-1-yl)ethyl)biphenyl-4-carboxylic acid and methyl 3-aminopropanoate, the title compound was obtained as a white solid using a similar method to the one described in Example 1.38. LCMS m/z=395.4 [M+H]$^+$; $^1$H NMR (400 MHz, DMSO-d$_6$) δ ppm 1.20 (d, J=6.3 Hz, 0.4H), 1.37 (d, J=6.3 Hz, 2.6H), 1.54-1.65 (m, 1H), 1.90-2.05 (m, 2H), 2.18-2.26 (m, 1H), 2.62 (t, J=7.8 Hz, 2H), 2.95-3.10 (m, 2H), 3.16-3.30 (m, 2H), 3.38-3.58 (m, 5H), 3.62 (s, 3H), 3.62-3.65 (m, 1H), 7.46 (d, J=8.2 Hz, 2H), 7.72 (d, J=8.2 Hz, 2H), 7.77 (d, J=8.2 Hz, 2H), 7.93 (d, J=8.2 Hz, 2H), 8.59 (t, 1H), 9.40 (bs, 1H).

Example 1.40

Preparation of (R)-Methyl 2-(4'-(2-(2-Methylpyrrolidin-1-yl)ethyl)biphenyl-4-ylcarboxamido)acetate (Compound 40)

From (R)-4'-(2-(2-methylpyrrolidin-1-yl)ethyl)biphenyl-4-carboxylic acid and methyl 2-aminoacetate, the title compound was obtained as a white solid using a similar method to the one described in Example 1.38. LCMS m/z=381.4 [M+H]$^+$; $^1$H NMR (400 MHz, DMSO-d$_6$) δ ppm 1.20 (d, J=6.3 Hz, 0.4H), 1.37 (d, J=6.3 Hz, 2.6H), 1.54-1.65 (m, 1H), 1.90-2.05 (m, 2H), 2.18-2.26 (m, 1H), 2.95-3.10 (m, 2H), 3.16-3.30 (m, 2H), 3.38-3.52 (m, 3H), 3.70 (s, 3H), 4.03 (d, J=6.3 Hz, 2H), 7.46 (d, J=8.2 Hz, 2H), 7.74 (d, J=8.2 Hz, 2H), 7.78 (d, J=8.2 Hz, 2H), 7.96 (d, J=8.2 Hz, 2H), 9.00 (t, 1H), 9.41 (bs, 1H).

Example 1.41

Preparation of (R)-2-(4'-(2-(2-Methylpyrrolidin-1-yl) ethyl)biphenyl-4-ylcarboxamido)acetic Acid (Compound 41)

To a 2.0 mL scintillation vial was added (R)-methyl 2-(4'-(2-(2-methylpyrrolidin-1-yl)ethyl)biphenyl-4-ylcarboxamido)acetate (39.7 mg, 0.104 mmol), sodium hydroxide (0.417 mL, 0.417 mmol), and THF (1.5 mL). The vial was sealed and stirred at 60° C. for 1 h. To the reaction mixture was added 1M HCl (417, µL). Water was removed and the resulting solid was washed with ethanol. The supernatant was dried (lyophilizer) to give the title compound as a white solid. LCMS m/z=367.3 [M+H]$^+$.

Example 1.42

Preparation of (R)-2-Methyl-2-(4'-(2-(2-methylpyrrolidin-1-yl)ethyl)biphenyl-4-ylcarboxamido)propanoic Acid (Compound 42)

From (R)-methyl 2-methyl-2-(4'-(2-(2-methylpyrrolidin-1-yl)ethyl)biphenyl-4-ylcarboxamido)propanoate, the title compound was obtained as a white solid using a similar method to the one described in Example 1.41. LCMS m/z=395.4 [M+H]$^+$.

Example 1.43

Preparation of (R)-3-(4'-(2-(2-Methylpyrrolidin-1-yl) ethyl)biphenyl-4-ylcarboxamido)propanoic Acid (Compound 43)

From (R)-methyl 3-(4'-(2-(2-methylpyrrolidin-1-yl)ethyl) biphenyl-4-ylcarboxamido)propanoate, the title compound was obtained as a white solid using a similar method to the one described in Example 1.41. LCMS m/z=381.2 [M+H]$^+$.

Example 1.44

Preparation of (R)-4'-(2-(2-Methylpyrrolidin-1-yl) ethyl)biphenyl-4-carboxylic Acid (Compound 1)

From (R)-4-(2-(2-methylpyrrolidin-1-yl)ethyl)phenylboronic acid hydrochloride and 4-bromobenzoic acid, the title compound was obtained as a yellow solid using a similar method to the one described in Example 1.37. LCMS m/z=310.2 [M+H]$^+$; $^1$H NMR (400 MHz, DMSO-d$_6$) δ ppm 1.20 (d, J=6.3 Hz, 0.4H), 1.37 (d, J=6.3 Hz, 2.6H), 1.54-1.65 (m, 1H), 1.90-2.05 (m, 2H), 2.18-2.26 (m, 1H), 2.95-3.10 (m, 2H), 3.16-3.30 (m, 2H), 3.40-3.60 (m, 2H), 3.62-3.68 (m, 1H), 7.46 (d, J=8.2 Hz, 2H), 7.74 (d, J=8.2 Hz, 2H), 7.80 (d, J=8.2 Hz, 2H), 8.02 (d, J=8.2 Hz, 2H), 9.36 (bs, 1H).

Example 1.45

Preparation of (R)-2-(4'-(2-(2-Methylpyrrolidin-1-yl) ethyl)biphenyl-4-yl)acetic Acid (Compound 2)

From (R)-4-(2-(2-methylpyrrolidin-1-yl)ethyl)phenylboronic acid hydrochloride and 2-(4-bromophenyl)acetic acid, the title compound was obtained as a white solid using a similar method to the one described in Example 1.37. LCMS m/z=324.2 [M+H]$^+$.

Example 1.46

Preparation of (R)-3-(4'-(2-(2-Methylpyrrolidin-1-yl) ethyl)biphenyl-4-yl)propanoic Acid (Compound 3)

In a microwave reaction vial was added (R)-1-(4-bromophenethyl)-2-methylpyrrolidine (200 mg, 0.746 mmol), 3-(4-boronophenyl)propanoic acid (289 mg, 1.491 mmol), Na$_2$CO$_3$ (395 mg, 3.73 mmol), dihydrogen dichlorobis(di-tert-butylphosphinito-kP)palladate (POPd) (11.23 mg, 0.022 mmol) and a mixture of H$_2$O (0.4 mL), MeOH (0.6 mL), and DMF (2.0 mL). The reaction mixture was heated under microwave irradiation at 150° C. for 15 min. To the mixture was added acetonitrile (20 mL) and filtered. The filtrate was concentrated and the residue was purified by HPLC to give the title compound. LCMS m/z=338.2 [M+H]$^+$; $^1$H NMR (400 MHz, CD$_3$CN) δ ppm 1.24 (d, J=14.9 Hz, 0.5H), 1.46 (d, J=6.3 Hz, 2.5H), 1.72-1.84 (m, 1H), 2.01-2.15 (m, 2H), 2.20-2.32 (m, 1H), 2.66 (t, J=7.5 Hz, 2H), 2.96 (t, J=7.5 Hz, 2H), 3.02-3.20 (m, 4H), 3.33-3.46 (m, 1H), 3.48-3.62 (m, 1H), 3.75-3.86 (m, 1H), 7.34 (d, J=8.2 Hz, 2H), 7.39 (d, J=8.2 Hz, 2H), 7.58 (d, J=8.2 Hz, 2H), 7.63 (d, J=8.2 Hz, 2H).

Example 2

[$^3$H]N-Alpha-Methyl-Histamine Competitive Histamine H3 Receptor Binding Assay

The histamine receptor binding assay is conducted using standard laboratory procedures as described below. A crude membrane fraction is prepared from whole rat brain cortex using a polytron to homogenize the tissue followed by differential centrifugation in a HEPES-based buffer containing protease inhibitors. Membranes are frozen at −80° C. until needed. Frozen membranes are thawed and resuspended in ice-cold assay buffer consisting of 50 mM TRIS containing 5 mM EDTA (pH=7.4). 50 µg of membrane protein is added to each well of a 96-well assay plate along with the test compound and [$^3$H]-N-α-methyl-histamine (1 nM final assay concentration). Imetit is used as an assay positive control at varying concentrations. The plate is incubated for 30 min at room temperature. The assay is terminated by rapid filtration through a 96-well glass fiber filtration plate (GF/C) using a cell harvester (Perkin-Elmer). Captured membranes are washed three times with cold assay buffer and the plates are dried at 50° C. 35 µL of scintillation cocktail is added to each well and membrane-bound radioactivity is recorded using a TopCount 96-well plate scintillation counter (Perkin-Elmer).

Example 3

Receptor Binding Assays

Compounds that bind to GPCRs can be identified by their ability to displace a radiolabeled or fluorescently labeled tracer ligand from the receptor. The tracer ligand can be a receptor agonist, inverse agonist or a neutral antagonist. Receptor binding assays can be performed using either whole cells or membrane fractions prepared from such cells.

In a typical radioligand binding assay, cell membranes prepared from cells either endogenously or recombinantly expressing the desired receptor, are prepared and allowed to equilibrate with a mixture of a test ligand and tracer radioligand. Following equilibration, the cell membranes are captured by rapid filtration and washed with cold assay buffer to remove any unbound compounds. A liquid scintillant is typically added to the captured membranes and the samples are then counted on a scintillation counter. Compounds that bind to the receptor and displace the radioligand result in lower counts. For some receptors, the radiolabeled tracer ligand can be replaced by a fluorescently labeled ligand.

Homogeneous binding assays have also been developed for some receptors. These can involve the use of either radioactive tracer ligands (e.g., scintillation proximity assays) or fluorescent tracer ligands (fluorescence polarization binding assays).

Example 3.1

Human Histamine H3 Receptor Binding Assay—MDS Pharma Services (Taiwan)

Compounds of the invention can be tested for their ability to bind to the human histamine H3 receptor using the MDS Pharma Services (Taiwan) assay, Catalogue No. 239810.

Example 3.2

Rat Cortex H3 Receptor Radioligand Binding Assay

Cell membranes prepared from isolated, Sprague-Dawley rat cortex, which are known to abundantly express the rat H3 receptor, are plated into 96-well microtiter plates at a concentration of 50 µg total membrane protein per well. Test compounds, prepared in assay buffer (50 mM Tris-HCl, pH7.4, with 5 mM EDTA) containing the selective H3 receptor agonist radioligand [$^3$H]N-methylhistamine (final assay concentration 1.25 nM), are added to each well on the plate. Test compound concentrations typically begin at 2 or 10 µM (final assay concentration) and 1:5 serial dilutions are prepared in order to generate 10-point dose-response curves for $IC_{50}$ and $K_i$ determinations. After a 1 hour, room temperature incubation, membranes are harvested into a PEI-washed filter plate (Whatman GF/C Unifilter) by rapid filtration (Perkin Elmer harvester) and washed three times with ice cold assay buffer (3×150 µL). Filter plates are then partially dried in a 50° C. oven for 1-2 hours. Finally, the plate bottoms are sealed and BetaScint (Perkin Elmer 1205-440; 25 µL per well) is added to each well. Plates are then read on a TopCount (Packard Instruments). Raw counts are then used to plot dose-response curves for serially diluted test compounds. The resulting $IC_{50}$ values can be converted to $K_i$ values using the Cheng-Prusoff equation and the $K_d$ value for [$^3$H]N-methylhistamine at the rat H3 receptor (0.4 nM).

Example 3.3

Assays for Determination of GPCR Activation or Inhibition

A variety of assays are available for assessment of activation or inhibition of GPCRs. The following are illustrative; those of ordinary skill in the art are credited with the ability to determine those techniques that are preferentially beneficial for the needs of the artisan.

1. Membrane [$^{35}$S]GTPγS Binding Assays.

When a G protein-coupled receptor is in its active state, either as a result of agonist ligand binding or constitutive activation, the receptor couples to G proteins, stimulating the release of GDP and subsequent binding of GTP to the G protein alpha subunit. The activated G protein alpha subunit acts as a GTPase and slowly hydrolyzes the GTP back to GDP. The non-hydrolyzable GTP analog, [$^{35}$S]GTPγS, can be utilized to monitor binding of GTP to membrane-associated G proteins. Typically, test compounds are incubated with receptor-expressing cell membranes in the presence of [$^{35}$S]GTPγS for 30 to 60 minutes. If the test compound is an agonist or an inverse agonist at the receptor of interest, enhanced or diminished uptake of [$^{35}$S]GTPγS into the membrane-associated G-proteins will be detected. A neutral antagonist, with no intrinsic efficacy at the receptor, can be detected by its ability to prevent agonist-stimulated [$^{35}$S]GTPγS exchange. The advantage of using [$^{35}$S]GTPγS binding to measure activation is that: (a) under appropriate assay conditions, it is generically applicable to all G protein-coupled receptors; (b) it is proximal at the membrane surface making it less likely to pick-up molecules which affect the rest of the G protein mediated intracellular signaling cascade.

Human H3 Receptor GTPγS Assay.

In a typical [$^{35}$S]GTPγS assay, recombinant human H3 receptor-expressing CHO-K1 cell membranes (90 µg membrane protein per well) are equilibrated in assay buffer (20 mM HEPES (pH 7.4), 10 mM $MgCl_2$, 100 mM NaCl, 1 mM DTT, 1 mM EDTA) containing test compounds and 10 µM GDP for 20 minutes. SPA beads (scintillation microsphere beads) are then added and incubated for 60 minutes at 30° C. The reaction is then initiated by the addition of 0.3 nM [$^{35}$S]GTPγS for 30 minutes. Plates are then sealed, centrifuged and counted in a scintillation counter (Packard TopCount).

The recombinantly-expressed H3 receptor is known to be constitutively active. In the above example, test compounds that have either positive (agonist) or negative (inverse agonist) efficacy at the H3 receptor would be detected by their ability to increase or decrease basal levels of [$^{35}$S]GTPγS binding, respectively. In an alternate configuration, the assay may be modified to include a low dose (typically an $EC_{80-90}$ concentration) of a selective H3 receptor agonist such as N-methylhistamine. In this approach, the ability to detect agonists is diminished and the ability to detect inverse agonists is increased. Additionally, antagonists (ligands with no intrinsic receptor efficacy) that block binding of the agonist to the receptor will be detected.

2. cAMP Assays.

GPCRs coupled to either Gs or Gi G-proteins modulate levels of intracellular cAMP and cAMP levels can be determined using a variety of commercially available assay kits. Examples of commonly used cAMP detection assays include FlashPlate® (New England Nuclear), HTRF® (Cisbio), cAMP-Screen® (Applied Biosystems), HitHunter® (Applied Biosystems/DiscoveRx), CatchPoint® (Molecular Devices), AlphaScreen® (Perkin Elmer), GloSensor® (Promega) and numerous ELISA products. Most of these assays rely on the use of an anti-cAMP antibody to detect cAMP.

Homogeneous time-resolved fluorescence assays (HTRF®, Cisbio) detect levels of cAMP in lysed cell preparations using a europium or terbium cryptate-labeled anti-cAMP antibody and fluorophore-labeled cAMP (cAMP-d2). In the absence of exogenous cAMP, the anti-cAMP antibody binds to cAMP-d2. Photoexcitation of the cryptate donor results in a combination of cryptate emission at 620 nm and fluorescence resonance energy transfer (FRET) from the cryptate to the acceptor d2 fluorophore, which then fluoresces at 665 nm. The 620/665 nm emission ratio is monitored. In the presence of exogenous cAMP, which competes with cAMP-d2 for binding to the anti-cAMP antibody, FRET is decreased and the 620/665 nm emission ratio therefore increases, providing a sensitive and accurate means to measure cAMP levels in biological assays.

Human H3 Receptor HTRF cAMP Assay.

Compounds of the present invention were evaluated using the human H3 receptor (H3R) HTRF cAMP assay. In this assay, HEK293 cells expressing the human H3 receptor were suspended in PBS containing 100 µM IBMX and plated into 384-well assay plates (Perkin Elmer Proxiplate 384-Plus; 15,000 cells per well; 5 µL plating volume) and allowed to equilibrate for an hour. Test compounds were serially diluted in 100% DMSO and then further diluted in PBS containing forskolin (2 µM). Test compounds (5 µL) were then added to the assay plate and the mixture was incubated for 1 hour. HTRF assay reagents (Cisbio, Dynamic 2 cAMP Kit), cAMP-d2 and cryptate-labeled anti-cAMP antibody, are mixed with cell lysis buffer and added to the assay plate. After 1-hour incubation with these reagents, the assay plate was read on an HTRF-compatible microplate reader (Perkin Elmer EnVision or BMG Pherastar). A cAMP standard curve was included on each assay plate and HTRF emission ratios for test compounds were fit to this curve to generate accurate measures of cAMP levels in each test well. The observed H3R $IC_{50}$ values in the HTRF cAMP assay for several compounds of the present invention are shown in Table B.

TABLE B

| Compound No. | $IC_{50}$ H3R | Compound | $IC_{50}$ H3R |
|---|---|---|---|
| 1 | 3.8 nM | 18 | 0.79 nM |
| 2 | 8.1 nM | 20 | 3.0 nM |
| 3 | 2.5 nM | 24 | 0.99 nM |
| 4 | 0.67 nM | 25 | 3.3 nM |
| 5 | 5.5 nM | 26 | 3.8 nM |
| 7 | 0.93 nM | 27 | 1.9 nM |
| 8 | 1.2 nM | 33 | 2.1 nM |
| 9 | 1.1 nM | 35 | 0.96 nM |
| 10 | 3.1 nM | 37 | 0.78 nM |
| 11 | 1.8 nM | 38 | 1.2 nM |
| 12 | 0.95 nM | 43 | 2.5 nM |
| 13 | 2.1 nM | 44 | 6.9 nM |
| 16 | 1.5 nM | 45 | 0.97 nM |

In addition to the compounds and their corresponding H3R $IC_{50}$ values disclosed in Table B, all other compounds in Table A had observed H3R $IC_{50}$ values in the HTRF cAMP assay ranging from about 0.48 nM to about 35 µM.

In an alternate configuration, designed to detect antagonists (ligands with no intrinsic receptor efficacy) that block binding of the agonist to the receptor the assay is modified to include a low dose of histamine (typically 20 nM) in the test compound buffer. The recombinantly-expressed H3 receptor is known to be constitutively active. In the above example, test compounds that have either positive (agonist) or negative (inverse agonist) efficacies are detected by their ability to decrease or increase forskolin stimulated levels of cAMP, respectively. In this configuration, both inverse agonists and antagonists are efficiently detected.

3. Xenopus Melanophore Assays.

Melanophores are skin cells found in lower vertebrates. They contain pigmented organelles termed melanosomes. Melanophores are able to redistribute these melanosomes along a microtubule network upon G-protein coupled receptor (GPCR) activation. The result of this pigment movement is an apparent lightening or darkening of the cells. In melanophores, the decreased levels of intracellular cAMP that result from activation of a Gi-coupled receptor such as the H3 receptor cause melanosomes to migrate to the center of the cell, resulting in a dramatic lightening in color. If cAMP levels are then raised, following activation of a Gs-coupled receptor or addition of an H3 receptor inverse agonist, the melanosomes are re-dispersed and the cells appear dark again. The response of the melanophores takes place within minutes of receptor activation and results in a simple, robust color change. The response can be easily detected using a conventional absorbance microplate reader or a modest video imaging system.

Since the H3 receptor is a constitutively active Gi-coupled receptor, melanophores expressing the H3 receptor will exhibit partial pigment aggregation in the resting state. Stimulation with an H3 receptor agonist or inverse agonist will cause either further pigment aggregation or dispersion, respectively. A neutral antagonist at the H3 receptor would be detected by its ability to inhibit pigment aggregation stimulated by a selective H3 receptor agonist 4. Intracellular Calcium and Inositol Phosphate Assays.

GPCRs coupled to Gq G-proteins regulate the activity of phospholipase C, resulting in the modulation of intracellular inositol phosphates (IP) and diacylglycerol levels. Increased IP levels result in activation of the IP receptor with consequent release of calcium ions into the cytosol. Levels of intracellular IP can be determined in cells loaded with [$^3$H]-myo-inositol, resulting in the production of tritiated IP, which can be detected using standard radiometric techniques. IP levels can also be determined using an HTRF IP-One assay (Cisbio) which relies on an antibody to inositol monophosphate to detect IP.

Cytosolic calcium can be monitored using membrane-permeable dyes that become fluorescent when bound to calcium. The most widely used instrument for conducting intracellular calcium release assays is the Fluorometric Imaging Plate Reader (FLIPR®, Molecular Devices). The FLIPR instrument is able to simultaneously add test compounds to all wells on appropriate microplates and take real-time measurements of the fluorescence of calcium bound dye, allowing accurate measurement of intracellular calcium levels. Similar experiments can be performed with a number of alternate, commercially available instruments or by the imaging of single cells or small numbers of cells with a fluorescence microscope.

Intracellular calcium levels can also be measured in cells engineered to express calcium sensitive proteins such as aequorin. Aequorin is a photoprotein isolated from jellyfish. While the calcium sensitive dyes used in FLIPR experiments require an excitation source in order to fluoresce, aequorin emits light in the presence of calcium without the need for an excitation source.

Receptors that do not normally couple to Gq G-proteins, such as the H3 receptor, can be artificially coupled to the IP/calcium signaling pathway through the use of promiscuous G-proteins ($G_{15}$ and $G_{16}$). These G-proteins signal through the Gq pathway and therefore regulate intracellular calcium release, but are promiscuous in the sense that they can couple to receptors that do not normally interact with Gq proteins. Alternatively, chimeric G-proteins may be used. These chimeric proteins typically utilize a Gq alpha protein in which approximately 5 amino acids at the carboxy-terminus are replaced with the corresponding amino acids from Gi alpha subunits. The resulting chimeric alpha subunit will recognize and be activated by Gi-coupled receptors but will signal though the Gq pathway to release intracellular calcium In a typical FLIPR assay, cells expressing the H3 receptor and either a promiscuous G-protein ($G_{15}$ or $G_{16}$) or a chimeric G-protein ($G_{qi}$) are suspended in assay buffer and plated into black 384-well assay plates. Calcium dye is then added to the wells and allowed to incubate with the cells for one hour prior to test compound addition on an instrument such as a FLIPR. H3 receptor agonists will stimulate and H3 receptor inverse agonists will inhibit, respectively, calcium release. Antagonists and inverse agonists are typically detected by their ability to block the action of a selective H3 receptor agonist.

5. β-Arrestin Assays.

Activation of a GPCR typically results in receptor phosphorylation via a variety of kinases and then recruitment of β-arrestin from the cytosol. By monitoring the translocation of β-arrestin proteins from the cytosol to GPCRs in the cell membrane or quantitating the amount of receptor-arrestin complex formed in the cell, one can determine the extent of receptor activation. The recruitment of arrestin and the formation of arrestin-GPCR complexes can result from both constitutive receptor activity and the influence of test compounds, with agonists promoting arrestin-receptor complexation.

Arrestin Translocation Assays

In a typical arrestin translocation assay, cells expressing the receptor of interest are plated in transparent assay plates and allowed to fully adhere to the bottom of the wells. Test compounds are then added and incubated with the cells for up to an hour. The intracellular location of arrestin may be monitored by the use of cells recombinantly expressing a modified arrestin protein fused to a fluorescent protein such as green fluorescent protein (GFP). Alternatively, cells can be fixed and permeabilized, then treated with a fluorescently labeled anti-β-arrestin antibody.

Arrestin-Receptor Interaction Assays

The association of β-arrestin with a GPCR can be monitored by tagging both β-arrestin and the receptor of interest with peptides or proteins that can interact to produce a biological readout when the receptor and arrestin are brought into close proximity upon receptor activation. Commercially available examples include Path Hunter® (DiscoveRx), in which the receptor and arrestin are tagged with complementary fragments of β-galactosidase that can combine via enzyme complementation upon receptor activation to produce active luciferase enzyme; and Tango® (Invitrogen), which utilizes an arrestin protein tagged with a protease and the receptor of interest tagged with a transcription factor at the cytoplasmic carboxyl terminus. The transcription factor is linked to the receptor via a protease-sensitive amino acid sequence and upon recruitment of protease-tagged arrestin, the transcription factor is cleaved from the receptor and translocates to the cell nucleus to initiate a transcriptional readout. Another commonly used technique for the measurement of arrestin-GPCR protein-protein interactions is bioluminescence resonance energy transfer (BRET). In this example, both arrestin and the receptor of interest are tagged with fluorescent proteins. One of the proteins is considered a donor while the other is an acceptor. Under conditions of low receptor activation, where arrestin is located primarily in the cytosol and the receptor is located primarily at the cell membrane, photoexcitation of the donor fluorescent protein, tagged to either the receptor or arrestin, results primarily in fluorescence emission from the donor. Upon receptor activation, resulting in close association of the receptor and arrestin, excitation of the donor protein is followed by BRET energy transfer to the acceptor protein and fluorescence emission from the acceptor protein at a longer wavelength that would be expected from the donor protein.

6. Reporter Gene Assays.

Activation of a GPCR typically results in changes in the activities of numerous protein signaling pathways within the cell. Some of these signaling pathways also lead to the modulations of intracellular concentrations of second messenger molecules such as cAMP, inositol phosphates, diacylglycerol and calcium. Many of these signaling pathways can ultimately result in a transcriptional response in the cell nucleus. Reporter gene assays take advantage of this response. Typically, cells are engineered to express a reporter gene product such as β-galactosidase or luciferase with gene expression regulated by a promoter that is sensitive to the type of signaling expected from the receptor of interest. In a typical example, cells expressing a receptor capable of modulating cAMP levels within the cell (Gi or Gs coupled) and a luciferase reporter gene under the control of a cAMP response element (CRE) can be used to determine intracellular cAMP levels. Activation of a Gs-coupled receptor or treatment with forskolin, leading to the production of cAMP, will increase reporter gene expression. Activation of a Gi coupled receptor such as the H3 receptor, leading to reductions in cAMP production, will reduce levels of reporter gene expression. For the constitutively active H3 receptor, agonists or inverse agonists would be detected by their ability to either decrease or increase forskolin-stimulated reporter gene expression, respectively. A neutral antagonist would be detected by its ability to block the actions of a selective H3 agonist.

Example 4

Blockade of RAMH-Induced Drinking Assay

When administered to rodents, H3 receptor agonists, such as (R)-α-methyl-histamine (RAMH), induce a drinking response that is sensitive to reversal with a H3 receptor inhibitor. Blockade of RAMH-induced drinking can therefore be utilized as an in vivo assay for functional H3 receptor inhibition activity. In this assay, male Sprague Dawley rats (250-350 g) are housed three per cage and maintained under a reverse 12 h light cycle (lights off at 1130 h). At 1030 h on the day of test, rats are individually housed in new cages and food is removed. 120 min later, rats are administered test article (vehicle or H3 receptor inhibitor, 0.3 mg/kg PO). 30 min later, water is removed, and RAMH (vehicle or RAMH 3 mg/kg salt SC) is administered. 10 min after administration of RAMH, weighed water bottles are placed in the cages, and drinking is allowed for 20 min. Water consumption is determined for each animal by weighing each bottle to the nearest 0.1 g. Data is expressed as percentage reduction in water intake according to the following formula:

[((VEH/RAMH)−(ANTAGONIST/RAMH))/((VEH/RAMH)−(VEH/VEH))]*100

Example 5

Histamine-Induced Model for Pruritus

Figure 1:
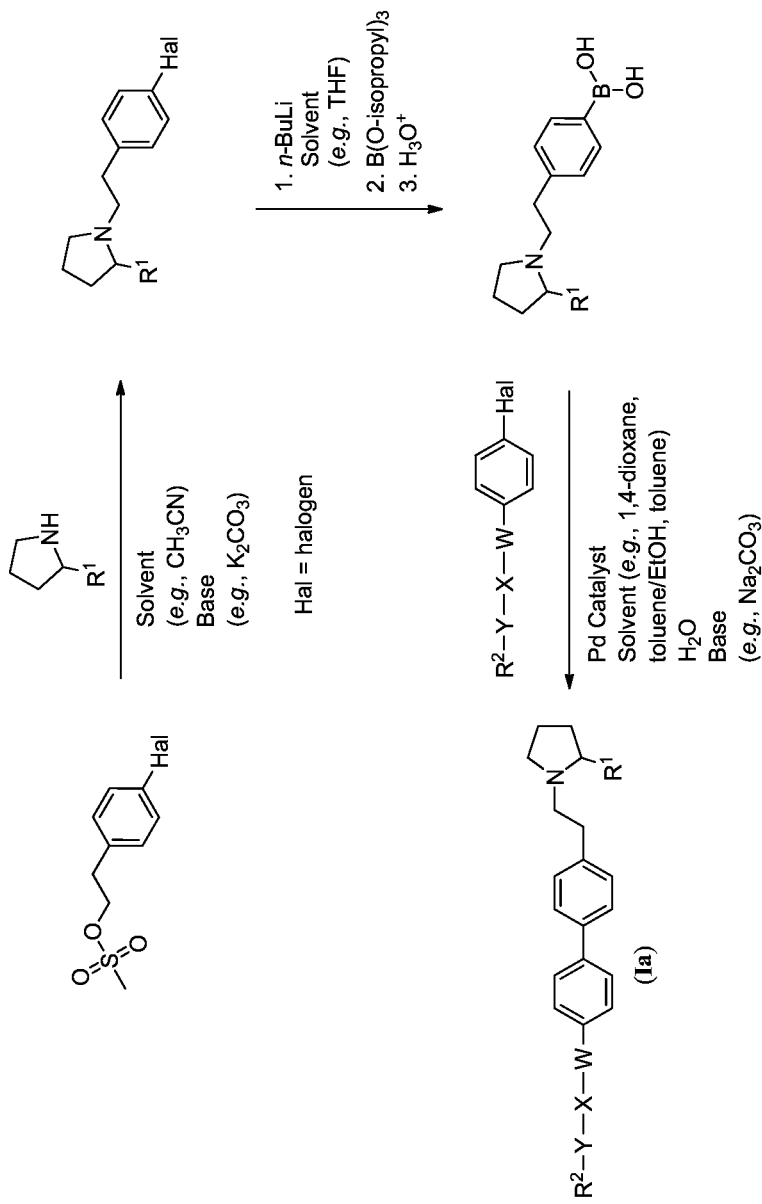
FIG. 1 shows a general synthetic scheme for the preparation of compounds of the present invention. First, a mesylate derivative is coupled with an $R^1$ substituted pyrrolidine and subsequently converted to an aryl boronic acid by treatment of an aryl lithium intermediate with triisopropyl borate followed by hydrolysis. Next the aryl boronic acid is coupled with a substituted haloaryl in the presence of a palladium catalyst to prepare compounds of Formula (Ia).
Figure 2:
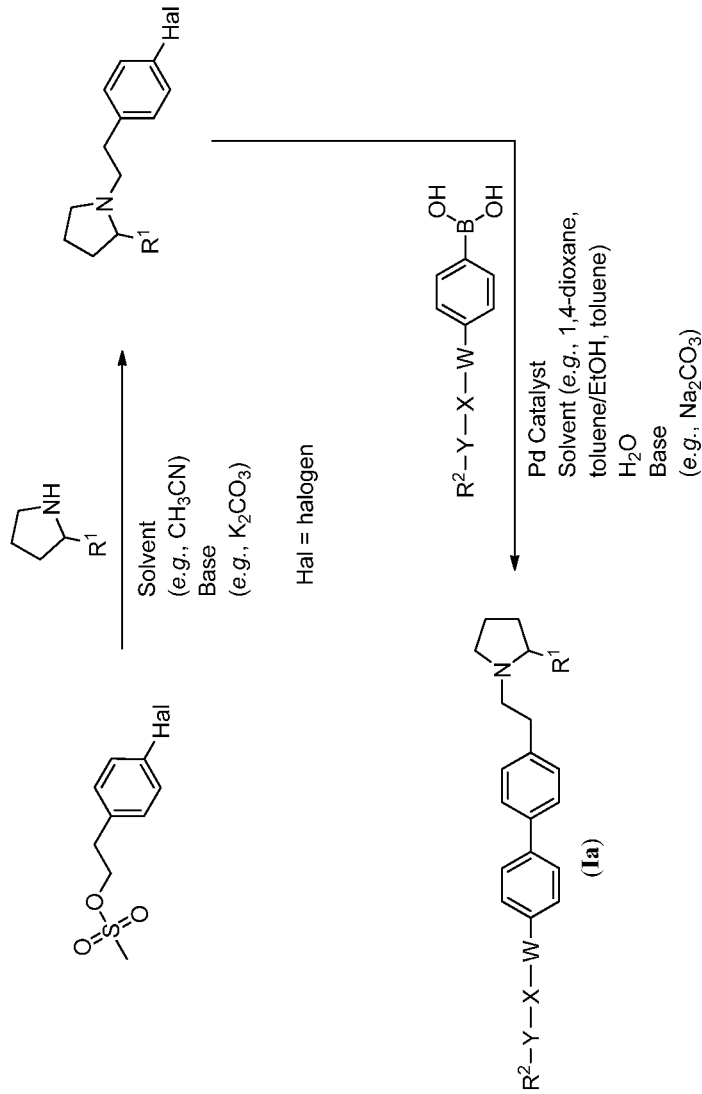
FIG. 2 shows a general synthetic scheme for the preparation of compounds of the present invention. First, a mesylate derivative is coupled with an $R^1$ substituted pyrrolidine to give a haloaryl that is subsequently coupled with an $R^2$—Y—X—W-substituted phenyl boronic acid in the presence of a palladium catalyst to prepare compounds of Formula (Ia).
Figure 3:
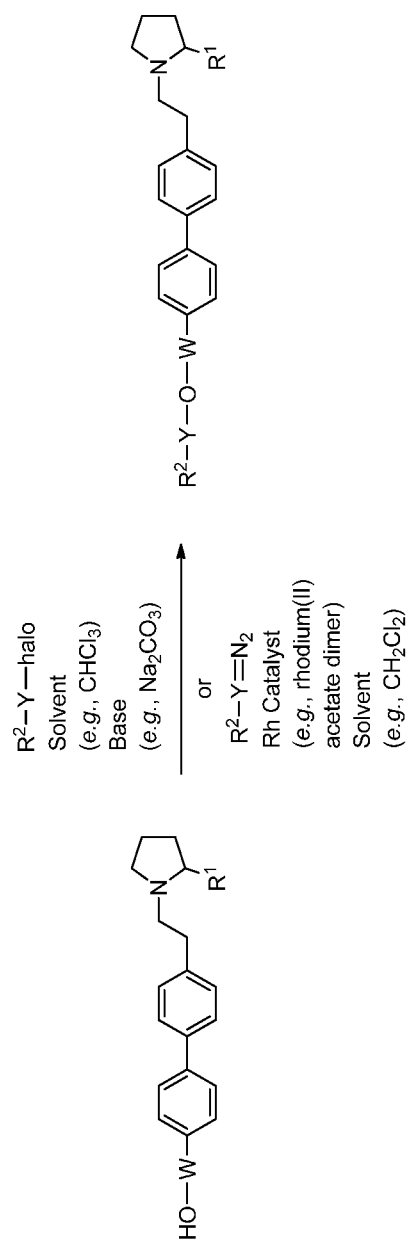
FIG. 3 shows a general method for preparing certain compounds of the present invention where X is O. A variety of methods can be used to prepare compounds where X is O such as displacement of a leaving group (e.g. halo) or reaction with a diazo agent in the presence of a rhodium (II) catalyst as shown in FIG. 3.
Figure 4:
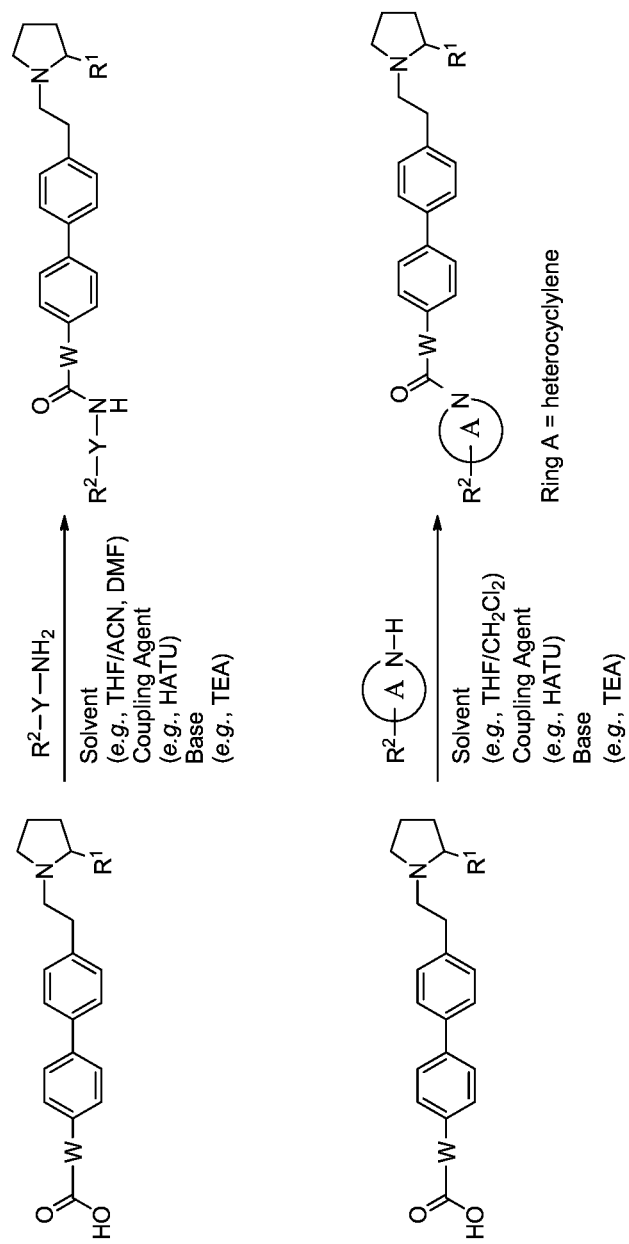
FIG. 4 shows general methods for preparing certain compounds of the present invention where: X is —NHC(=O)—; and X is carbonyl (i.e., —C(=O)—) wherein Y is hetercyclylene. A variety of coupling methods can be used to prepare these compounds, such as those shown in FIG. 4.
Figure 5:
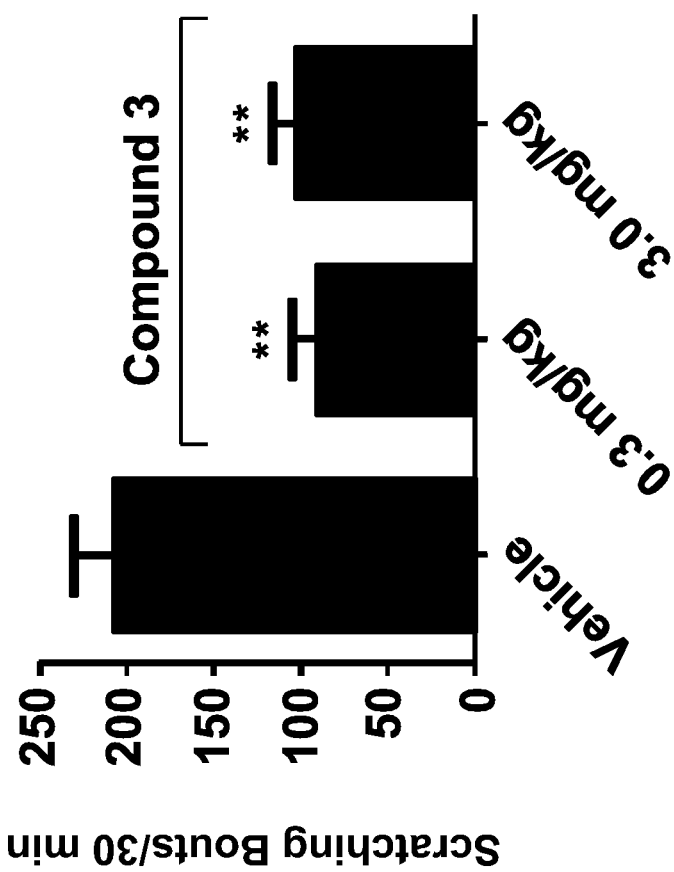
FIG. 5 shows the data from the oral administration of Compound 3 in the histamine-induced pruritus mouse model.

C57BL/6 mice (9 per group) were administered with either vehicle (0.5% Methocellulose) or Compound 3. Thirty minutes post-dosing, the mice were injected with histamine (3 μmol) subcutaneously and placed in a clear observation box. Mice were video recorded and the number of scratching bouts that occurred between 0 and 30 minutes was counted after histamine injection. Compound 3 was found to inhibit histamine-induced scratching behavior in mice, see FIG. 5.

Example 6

Histamine-Induced Model for Pruritus

H3R inhibitors, Compound 3 and Compound 11, were dissolved in 0.5% methylcellulose at the appropriate concentration and 100 μL were administered orally to 8-week-old C57BL/6j male mice. Thirty minutes post-dosing, 25 μL of 40 mg/mL histamine solution was injected subcutaneously at the rostral part of the back. Mice were video recorded and the number of scratching bouts that occurred between 5 and 15 minutes was counted after histamine injection. Both compounds were found to inhibit histamine-induced scratching behavior in mice, see FIG. 6.

Example 7

Pharmacology Study of Compound 3 in male C57BL6 Mouse, Brain to Plasma Ratio Determination Male C57BL6 mice were administered Compound 3 at 3 mg/kg by either intraperitoneal injection (IP) or oral gavage (PO). Plasma and brain samples were collected at 0.5 and 2.0 h post-dose. Blood samples were collected via eye bleed, followed by decapitation and extraction of the brain from the cranial cavity. Blood was treated with 0.5% EDTA; plasma was separated by centrifugation. Brain tissue was placed in ice-cold containers. Plasma and brain samples were frozen at approximately −70° C. until assayed at Arena Pharmaceuticals. Compound 3 plasma and brain concentrations were determined by LC/MS/MS. The lower limit of quantitation (i.e., LLQ) was 25.0 and 3.0 ng/mL for plasma and brain, respectively.

After IP administration, Compound 3 plasma and brain concentrations were 1350±104 ng/mL and 71.7±10.7 ng/g at 0.5 h, respectively and 364±135 ng/mL and 17.2±7.5 ng/g at 2.0 h, respectively. The brain-to-plasma ratio was approximately 0.05 independent of time. These trends were also observed after PO administration where Compound 3 plasma and brain concentration were 1080±487 ng/mL and 39.8±22.7 ng/g at 0.5 h, respectively and 619±185 ng/mL and 29.1±7.0 ng/g at 2.0 h, respectively. The brain-to-plasma ratio was 0.04 and 0.05 at 0.5 and 2.0 h post-dose, respectively.

Example 8

H3R Antagonists in Allergic Models for Pruritus

To perform the DNFB allergic pruritus model, female C57BL/6 mice (5/group) are sensitized two times/week via epicutaneous administration of the allergen DNFB (for example, 0.3% in 4:1 acetone:olive oil) on the rostral back skin. On the 14th day after initial DNFB administration, mice are challenged again with epicutaneous DNFB; at 5 h post-DNFB challenge, mice are dosed with an H3R antagonist at various concentrations, for example, 1, 3, 10, and 30 mg/kg, IP. Scratching bouts are counted from 30-50 minutes post-compound dosing. H3R antagonists that inhibit scratching bouts in this model demonstrate they are able to inhibit pruritus mediated by endogenous pruritogens released from an immune response.

Those skilled in the art will recognize that various modifications, additions, substitutions and variations to the illustrative examples set forth herein can be made without departing from the spirit of the invention and are, therefore, considered within the scope of the invention.

What is claimed is:
1. A compound selected from compounds of Formula (Ia) and pharmaceutically acceptable salts, solvates, and hydrates thereof:

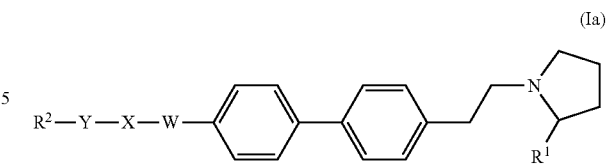

(Ia)

wherein:
R$^1$ is C$_1$-C$_4$ alkyl;
R$^2$ is selected from: C$_1$-C$_4$ alkoxycarbonyl, carboxyl, and tetrazolyl;
W is selected from: C$_1$-C$_4$ alkylene, C$_3$-C$_7$ cycloalkylene, and carbonyl; or
W is absent;
X is selected from: —O—, —NHC═O—, and carbonyl; or
X is absent; and
Y is selected from: C$_1$-C$_4$ alkylene, C$_3$-C$_7$ cycloalkylene, and heterocyclylene; or
Y is absent.

2. A compound according to claim 1, wherein R$^1$ is methyl.
3. A compound according to claim 1, wherein R$^2$ is selected from: methoxycarbonyl, ethoxycarbonyl, tert-butoxycarbonyl, carboxyl, 1H-tetrazol-1-yl, 2H-tetrazol-2-yl, and 1H-tetrazol-5-yl.
4. A compound according to claim 1, wherein R$^2$ is C$_1$-C$_4$ alkoxycarbonyl.
5. A compound according to claim 4, wherein R$^2$ is selected from: methoxycarbonyl, ethoxycarbonyl, and tert-butoxycarbonyl.
6. A compound according to claim 1, wherein R$^2$ is carboxyl.
7. A compound according to claim 1, wherein W is selected from: methylene, ethane-1,2-diyl, propane-2,2-diyl, propane-1,3-diyl, cyclopentane-1,1-diyl, and carbonyl.
8. A compound according to claim 1, wherein W is C$_1$-C$_4$ alkylene.
9. A compound according to claim 8, wherein W is selected from: methylene, ethane-1,2-diyl, propane-1,3-diyl, and propane-2,2-diyl.
10. A compound according to claim 1, wherein W is absent.
11. A compound according to claim 1, wherein X is absent.
12. A compound according to claim 1, wherein Y is selected from: methylene, propane-2,2-diyl, propane-1,3-diyl, ethane-1,1-diyl, ethane-1,2-diyl, cyclohexane-1,2-diyl, pyrrolidine-1,2-diyl, and piperidine-1,4-diyl.
13. A compound according to claim 1, wherein Y is C$_1$-C$_4$ alkylene.
14. A compound according to claim 13, wherein Y is selected from: methylene, propane-2,2-diyl, propane-1,3-diyl, ethane-1,1-diyl, and ethane-1,2-diyl.
15. A compound according to claim 1, wherein Y is absent.
16. The compound according to claim 1, selected from compounds of Formula (Ic) and pharmaceutically acceptable salts, solvates, and hydrates thereof:

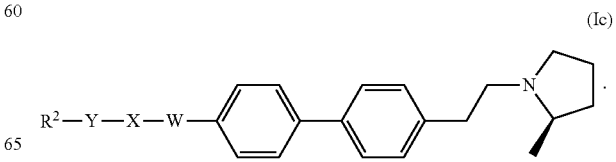

(Ic)

17. The compound according to claim 1, selected from compounds of Formula (Ic) and pharmaceutically acceptable salts, solvates, and hydrates thereof:

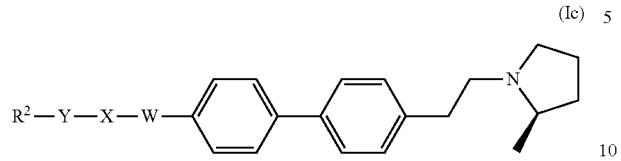

wherein:
- $R^2$ is selected from: methoxycarbonyl, ethoxycarbonyl, tert-butoxycarbonyl, carboxyl, 1H-tetrazol-1-yl, 2H-tetrazol-2-yl, and 1H-tetrazol-5-yl;
- W is selected from: methylene, ethane-1,2-diyl, propane-2,2-diyl, propane-1,3-diyl, cyclopentane-1,1-diyl, and carbonyl; or
- W is absent;
- X is selected from: —O—, —NHC=O—, and carbonyl; or
- X is absent; and
- Y is selected from: methylene, propane-2,2-diyl, propane-1,3-diyl, ethane-1,1-diyl, ethane-1,2-diyl, cyclohexane-1,2-diyl, pyrrolidine-1,2-diyl, and piperidine-1,4-diyl; or
- Y is absent.

18. The compound according to claim 1, selected from compounds of Formula (Ic) and pharmaceutically acceptable salts, solvates, and hydrates thereof:

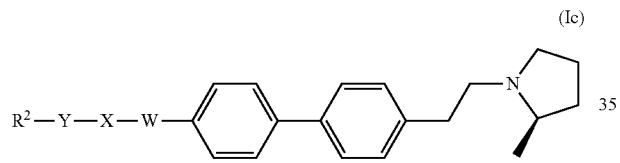

wherein:
- $R^2$ is selected from: $C_1$-$C_4$ alkoxycarbonyl, carboxyl, and tetrazolyl;
- W is selected from: $C_1$-$C_4$ alkylene and $C_3$-$C_7$ cycloalkylene;
- X is selected from: —O—, —NHC=O—, and carbonyl; or
- X is absent; and
- Y is selected from: $C_1$-$C_4$ alkylene, $C_3$-$C_7$ cycloalkylene, and heterocyclylene; or
- Y is absent.

19. The compound according to claim 1, selected from compounds of Formula (Ic) and pharmaceutically acceptable salts, solvates, and hydrates thereof:

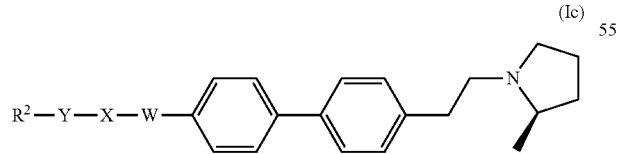

wherein:
- $R^2$ is selected from: methoxycarbonyl, ethoxycarbonyl, tert-butoxycarbonyl, carboxyl, 1H-tetrazol-1-yl, 2H-tetrazol-2-yl, and 1H-tetrazol-5-yl;
- W is selected from: methylene, ethane-1,2-diyl, propane-2,2-diyl, propane-1,3-diyl, and cyclopentane-1,1-diyl;
- X is selected from: —O—, —NHC=O—, and carbonyl; or
- X is absent; and
- Y is selected from: methylene, propane-2,2-diyl, propane-1,3-diyl, ethane-1,1-diyl, ethane-1,2-diyl, cyclohexane-1,2-diyl, pyrrolidine-1,2-diyl, and piperidine-1,4-diyl; or
- Y is absent.

20. The compound according to claim 1, selected from compounds of Formula (Ie) and pharmaceutically acceptable salts, solvates, and hydrates thereof:

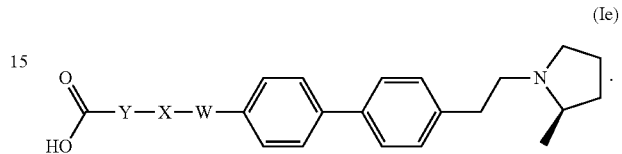

21. The compound according to claim 1, selected from compounds of Formula (Ie) and pharmaceutically acceptable salts, solvates, and hydrates thereof:

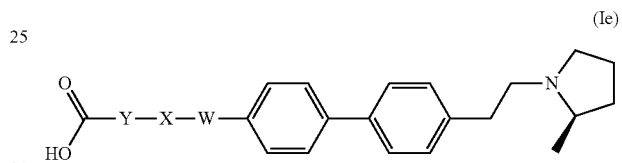

wherein:
- W is selected from: $C_1$-$C_4$ alkylene and $C_3$-$C_7$ cycloalkylene;
- X is selected from: —O—, —NHC=O—, and carbonyl; or
- X is absent; and
- Y is selected from: $C_1$-$C_4$ alkylene, $C_3$-$C_7$ cycloalkylene, and heterocyclylene; or
- Y is absent.

22. The compound according to claim 1, selected from compounds of Formula (Ie) and pharmaceutically acceptable salts, solvates, and hydrates thereof:

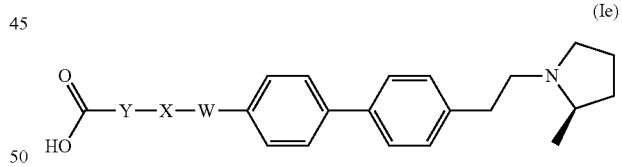

wherein:
- W is selected from: methylene, ethane-1,2-diyl, propane-2,2-diyl, propane-1,3-diyl, and cyclopentane-1,1-diyl;
- X is selected from: —O—, —NHC=O—, and carbonyl; or
- X is absent; and
- Y is selected from: methylene, propane-2,2-diyl, propane-1,3-diyl, ethane-1,1-diyl, ethane-1,2-diyl, cyclohexane-1,2-diyl, and pyrrolidine-1,2-diyl; or
- Y is absent.

23. A compound according to claim 1 selected from the following compounds and pharmaceutically acceptable salts, solvates, and hydrates thereof:
(R)-4'-(2-(2-methylpyrrolidin-1-yl)ethyl)biphenyl-4-carboxylic acid;

(R)-2-(4'-(2-(2-methylpyrrolidin-1-yl)ethyl)biphenyl-4-yl)acetic acid;
(R)-3-(4'-(2-(2-methylpyrrolidin-1-yl)ethyl)biphenyl-4-yl)propanoic acid;
(R)-ethyl 2-((4'-(2-(2-methylpyrrolidin-1-yl)ethyl)biphenyl-4-yl)methoxy)acetate;
(R)-2-((4'-(2-(2-methylpyrrolidin-1-yl)ethyl)biphenyl-4-yl)methoxy)acetic acid;
(R)-2-(2-(4'-(2-(2-methylpyrrolidin-1-yl)ethyl)biphenyl-4-yl)ethoxy)acetic acid;
(R)-1-(2-(4'-(2-(2-methylpyrrolidin-1-yl)ethyl)biphenyl-4-yl)ethyl)-1H-tetrazole;
(R)-2-(2-(4'-(2-(2-methylpyrrolidin-1-yl)ethyl)biphenyl-4-yl)ethyl)-2H-tetrazole;
(R)-methyl 3-(4'-(2-(2-methylpyrrolidin-1-yl)ethyl)biphenyl-4-yl)propanoate;
(R)-2-methyl-2-(4'-(2-(2-methylpyrrolidin-1-yl)ethyl)biphenyl-4-yl)propanoic acid;
(R)-ethyl 3-(4'-(2-(2-methylpyrrolidin-1-yl)ethyl)biphenyl-4-yl)propanoate;
(R)-tert-butyl 2-methyl-2-(3-(4'-(2-(2-methylpyrrolidin-1-yl)ethyl)biphenyl-4-yl)propanamido)propanoate;
(S)-tert-butyl 2-(3-(4'-(2-((R)-2-methylpyrrolidin-1-yl)ethyl)biphenyl-4-yl)propanamido)propanoate;
(1R,2R)-ethyl 2-(1-(4'-(2-((R)-2-methylpyrrolidin-1-yl)ethyl)biphenyl-4-yl)cyclopentanecarboxamido)cyclohexanecarboxylate;
(R)-ethyl 3-(1-(4'-(2-(2-methylpyrrolidin-1-yl)ethyl)biphenyl-4-yl)cyclopentanecarboxamido)propanoate;
(R)-methyl 4-(1-(4'-(2-(2-methylpyrrolidin-1-yl)ethyl)biphenyl-4-yl)cyclopentanecarboxamido)butanoate;
(R)-2-methyl-2-(3-(4'-(2-(2-methylpyrrolidin-1-yl)ethyl)biphenyl-4-yl)propanamido)propanoic acid;
(S)-2-(3-(4'-(2-((R)-2-methylpyrrolidin-1-yl)ethyl)biphenyl-4-yl)propanamido)propanoic acid;
(R)-1-(4'-(2-(2-methylpyrrolidin-1-yl)ethyl)biphenyl-4-yl)cyclopentanecarboxylic acid;
(1R,2S)-ethyl 2-(1-(4'-(2-((R)-2-methylpyrrolidin-1-yl)ethyl)biphenyl-4-yl)cyclopentanecarboxamido)cyclohexanecarboxylate;
(R)-methyl 3-(1-(4'-(2-(2-methylpyrrolidin-1-yl)ethyl)biphenyl-4-yl)cyclopentanecarboxamido)propanoate;
(R)-tert-butyl 3-(1-(4'-(2-(2-methylpyrrolidin-1-yl)ethyl)biphenyl-4-yl)cyclopentanecarboxamido)propanoate;
(R)-tert-butyl 4-(1-(4'-(2-(2-methylpyrrolidin-1-yl)ethyl)biphenyl-4-yl)cyclopentanecarboxamido)butanoate;
(R)-methyl 2-(3-(4'-(2-(2-methylpyrrolidin-1-yl)ethyl)biphenyl-4-yl)propanamido)acetate;
(R)-methyl 1-(4'-(2-(2-methylpyrrolidin-1-yl)ethyl)biphenyl-4-yl)cyclopentanecarboxylate;
(R)-tert-butyl 2-(3-(4'-(2-(2-methylpyrrolidin-1-yl)ethyl)biphenyl-4-yl)propanamido)acetate;
(R)-methyl 2-(1-(4'-(2-(2-methylpyrrolidin-1-yl)ethyl)biphenyl-4-yl)cyclopentanecarboxamido)acetate;
(S)-methyl 2-(1-(4'-(2-((R)-2-methylpyrrolidin-1-yl)ethyl)biphenyl-4-yl)cyclopentanecarboxamido)propanoate;
(R)-2-(3-(4'-(2-(2-methylpyrrolidin-1-yl)ethyl)biphenyl-4-yl)propanamido)acetic acid;
(1R,2R)-2-(1-(4'-(2-((R)-2-methylpyrrolidin-1-yl)ethyl)biphenyl-4-yl)cyclopentanecarboxamido)cyclohexanecarboxylic acid;
(R)-tert-butyl 3-(3-(4'-(2-(2-methylpyrrolidin-1-yl)ethyl)biphenyl-4-yl)propanamido)propanoate;
(S)-1-(3-(4'-(2-((R)-2-methylpyrrolidin-1-yl)ethyl)biphenyl-4-yl)propanoyl)pyrrolidine-2-carboxylic acid;
(R)-4-(1-(4'-(2-(2-methylpyrrolidin-1-yl)ethyl)biphenyl-4-yl)cyclopentanecarboxamido)butanoic acid;
(R)-tert-butyl 4-(3-(4'-(2-(2-methylpyrrolidin-1-yl)ethyl)biphenyl-4-yl)propanamido)butanoate;
(R)-ethyl 1-(3-(4'-(2-(2-methylpyrrolidin-1-yl)ethyl)biphenyl-4-yl)propanoyl)piperidine-4-carboxylate;
(R)-4-(4'-(2-(2-methylpyrrolidin-1-yl)ethyl)biphenyl-4-yl)-4-oxobutanoic acid;
(R)-5-((4'-(2-(2-methylpyrrolidin-1-yl)ethyl)biphenyl-4-yl)methyl)-1H-tetrazole;
(R)-methyl 2-methyl-2-(4'-(2-(2-methylpyrrolidin-1-yl)ethyl)biphenyl-4-ylcarboxamido)propanoate;
(R)-methyl 3-(4'-(2-(2-methylpyrrolidin-1-yl)ethyl)biphenyl-4-ylcarboxamido)propanoate;
(R)-methyl 2-(4'-(2-(2-methylpyrrolidin-1-yl)ethyl)biphenyl-4-ylcarboxamido)acetate;
(R)-2-(4'-(2-(2-methylpyrrolidin-1-yl)ethyl)biphenyl-4-ylcarboxamido)acetic acid;
(R)-2-methyl-2-(4'-(2-(2-methylpyrrolidin-1-yl)ethyl)biphenyl-4-ylcarboxamido)propanoic acid;
(R)-3-(4'-(2-(2-methylpyrrolidin-1-yl)ethyl)biphenyl-4-ylcarboxamido)propanoic acid;
(R)-5-(2-(4'-(2-(2-methylpyrrolidin-1-yl)ethyl)biphenyl-4-yl)ethyl)-1H-tetrazole;
(R)-4-(4'-(2-(2-methylpyrrolidin-1-yl)ethyl)biphenyl-4-yl)butanoic acid; and
(R)-ethyl 4-(4'-(2-(2-methylpyrrolidin-1-yl)ethyl)biphenyl-4-yl)butanoate.

24. A pharmaceutical composition comprising a compound according to claim 1 and a pharmaceutically acceptable carrier.

25. A method of inducing wakefulness in an individual comprising administering to said individual in need thereof a therapeutically effective amount of a compound according to claim 1.

26. A method for treating an H3 receptor-associated disorder selected from the group consisting of: a cognitive disorder, epilepsy, brain trauma, depression, obesity, disorders of sleep and wakefulness, attention deficit hyperactivity disorder (ADHD), schizophrenia, allergic rhinitis, dementia, Alzheimer's disease, pain, and pruritus in an individual comprising administering to said individual having said disorder, a therapeutically effective amount of a compound according to claim 1.

27. A method for treating allergic rhinitis in an individual comprising administering to said individual having allergic rhinitis, a therapeutically effective amount of a compound according to claim 1.

28. A method for treating pruritus in an individual comprising administering to said individual having said pruritus a therapeutically effective amount of a compound according to claim 1, wherein said pruritus is associated with a disorder selected from eczema, atopic eczematous dermatitis, seborrheic dermatitis, atopic dermatitis, contact dermatitis, irritant dermatitis, xerosis (dry skin), itch associated with inflammation, itch associated with allergies, photodematoses, skin blisters, adult acne, chicken pox, dermatitis herpetiformis, histamine-induced pruritus and pruritus mediated by endogenous pruritogens released from an immune response.

* * * * *